(12) United States Patent
Philip

(10) Patent No.: US 10,882,894 B2
(45) Date of Patent: Jan. 5, 2021

(54) PEPTIDIC TGF-BETA ANTAGONISTS

(71) Applicant: Anie Philip, Montréal (CA)

(72) Inventor: Anie Philip, Montréal (CA)

(73) Assignee: Anie Philip, Montréal (CA)

( * ) Notice: Subject to any disclaimer, the term of this patent is extended or adjusted under 35 U.S.C. 154(b) by 0 days.

(21) Appl. No.: 15/751,538

(22) PCT Filed: Aug. 11, 2016

(86) PCT No.: PCT/CA2016/050942
§ 371 (c)(1),
(2) Date: Dec. 7, 2018

(87) PCT Pub. No.: WO2017/024407
PCT Pub. Date: Feb. 16, 2017

(65) Prior Publication Data
US 2019/0112350 A1    Apr. 18, 2019

Related U.S. Application Data

(60) Provisional application No. 62/203,469, filed on Aug. 11, 2015.

(51) Int. Cl.
| | | |
|---|---|---|
| *A61K 38/18* | (2006.01) |
| *A61K 38/10* | (2006.01) |
| *A61K 38/16* | (2006.01) |
| *A61K 38/00* | (2006.01) |
| *A61K 38/04* | (2006.01) |
| *C07K 14/495* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 14/705* | (2006.01) |
| *A61L 17/00* | (2006.01) |
| *A61L 24/00* | (2006.01) |
| *A61K 35/36* | (2015.01) |
| *C12N 15/86* | (2006.01) |
| *C12N 15/87* | (2006.01) |
| *C07K 14/71* | (2006.01) |
| *A61L 31/16* | (2006.01) |
| *A01K 67/027* | (2006.01) |
| *A61L 15/44* | (2006.01) |
| *A61K 38/03* | (2006.01) |
| *C07K 7/08* | (2006.01) |
| *C07K 14/00* | (2006.01) |
| *A61P 1/16* | (2006.01) |
| *A61P 17/02* | (2006.01) |
| *A61P 35/00* | (2006.01) |

(Continued)

(52) U.S. Cl.
CPC .... *C07K 14/70596* (2013.01); *A01K 67/0271* (2013.01); *A61K 9/006* (2013.01); *A61K 9/0019* (2013.01); *A61K 9/0048* (2013.01); *A61K 9/0073* (2013.01); *A61K 9/7038* (2013.01); *A61K 35/36* (2013.01); *A61K 38/00* (2013.01); *A61K 38/03* (2013.01); *A61K 38/10* (2013.01); *A61K 38/16* (2013.01); *A61K 38/1841* (2013.01); *A61L 15/44* (2013.01); *A61L 17/005* (2013.01); *A61L 24/0015* (2013.01); *A61L 31/16* (2013.01); *A61P 1/16* (2018.01); *A61P 17/02* (2018.01); *A61P 35/00* (2018.01); *C07K 7/00* (2013.01); *C07K 7/08* (2013.01); *C07K 14/00* (2013.01); *C07K 14/495* (2013.01); *C07K 14/71* (2013.01); *C12N 15/86* (2013.01); *C12N 15/87* (2013.01); *A61L 2300/432* (2013.01); *Y02A 50/30* (2018.01)

(58) Field of Classification Search
None
See application file for complete search history.

(56) References Cited

U.S. PATENT DOCUMENTS

| 7,173,002 | B2 * | 2/2007 | Philip | C07K 14/71 |
| | | | | 424/185.1 |
| 2012/0079614 | A1 * | 3/2012 | Philip | C12N 15/8509 |
| | | | | 800/18 |

FOREIGN PATENT DOCUMENTS

WO    2010088778 A1    8/2010

OTHER PUBLICATIONS

UniProt Accession No. A0A0D9RNK9, 7 pages (2015) (Year: 2015).*

(Continued)

*Primary Examiner* — James H Alstrum-Acevedo
*Assistant Examiner* — Thea D'Ambrosio
(74) *Attorney, Agent, or Firm* — Carmela De Luca; Amy Dam; Bereskin & Parr LLP

(57) ABSTRACT

The present invention provides peptidic TGF-β antagonists capable of inhibiting TGF-β signaling and disrupting the biochemical events that promote fibrosis and the epithelial-mesenchymal transition. The peptidic TGF-β antagonist may contain from 11 to 28 amino acid residues (for instance, may consist of from 12 to 16 amino acid residues) and may have the following structure (II): $NH_2$'ETWIWLDTNMG-$Xaa_1$-Y'COOH (II) wherein Xaa1 is any amino acid and Y is a peptide having from 0 to 9 amino acids. The peptidic TGF-β antagonists can advantageously be used for the prevention, treatment, and/or alleviation of the symptoms of a condition associated with an increase in TGF-β activity, including fibrosis (such as fibrosis of the skin, liver, lungs, and heart, among others) and cancer (including various carcinomas, such as squamous cell carcinoma, sarcomas, and metastatic cancers).

16 Claims, 49 Drawing Sheets

Specification includes a Sequence Listing.

(51) Int. Cl.
    *A61K 9/00*     (2006.01)
    *A61K 9/70*     (2006.01)

(56) References Cited

OTHER PUBLICATIONS

UniProt Accession No. Q6YHK3, 16 pages (2006) (Year: 2006).*
Man et al.: "CD109, a TGF-[beta] co-receptor, attenuates extracellular matrix production in scleroderma skin fibrobl", Arthritis Research and Therapy, vol. 14, 2012, pp. 1-12.
Massague et al.: "TGF[beta] Signaling in Growth Control, Cancer, and Heritable Disorders", Cell, vol. 103, 2000, pp. 295-309.
Li et al.: "Soluble CD109 binds TGF-[beta] and antagonizes TGF-[beta] signalling and responses", Biochemical Journal, vol. 473, 2016, pp. 537-547.
International Search Report of PCT/CA2016/050942, dated Oct. 24, 2016.
Supplementary European Search Report for EP 16834367.1, dated Apr. 25, 2019.
Bizet et al.: "The TGF-beta co-receptor, CD109, promotes internalization and degradation of TGF-beta receptors", Biochim Biophys Acta: Molecular Cell Research, vol. 1813, 2011, pp. 742-753.
Cash et al.: "Development of a Small-Molecule Screening Method for Inhibitors of Cellular Response to Myostatin and Activin A", Journal of Biomolecular Screening, vol. 18, 2013, pp. 837-844.
Conchillo-Sole et al.: "AGGRESCAN: a server for the prediction and evaluation of "hot spots" of aggregation in polypeptides", BMC Bioinformatics, 2007, 8:65.
Frokjaer et al.: "Protein drug stability: a formulation challenge", Nature Reviews, Dug Discovery, vol. 4, 2005, pp. 298-306.

* cited by examiner

| # | AA | aw | HSA | NBSA | a+cAH/z |
|---|----|----|-----|------|---------|
| 1 | L | -0.273 | 0.000 | 0.000 | 0.000 |
| 2 | G | -0.273 | 0.000 | 0.000 | 0.000 |
| 3 | S | -0.015 | 0.005 | 0.000 | -0.015 |
| 4 | S | -0.498 | 0.000 | 0.000 | 0.000 |
| 5 | P | -0.072 | 0.000 | 0.000 | 0.000 |
| 6 | H | -0.261 | 0.000 | 0.000 | 0.000 |
| 7 | V | -0.389 | 0.000 | 0.000 | 0.000 |
| 8 | R | -0.529 | 0.000 | 0.000 | 0.000 |
| 9 | K | 0.029 | 0.049 | 0.000 | 0.029 |
| 10 | H | -0.357 | 0.000 | 0.000 | 0.000 |
| 11 | F | -0.391 | 0.000 | 0.000 | 0.000 |
| 12 | P | -0.237 | 0.000 | 0.000 | 0.000 |
| 13 | E | 0.177 | 3.113 | 0.519 | 0.499 |
| 14 | T | 0.191 | 3.113 | 0.519 | 0.499 |
| 15 | W | 0.465 | 3.113 | 0.519 | 0.499 |
| 16 | I | 1.023 | 3.113 | 0.519 | 0.499 |
| 17 | W | 0.688 | 3.113 | 0.519 | 0.499 |
| 18 | L | 0.449 | 3.113 | 0.519 | 0.499 |
| 19 | D | -0.176 | 0.000 | 0.000 | 0.000 |
| 20 | T | -0.201 | 0.000 | 0.000 | 0.000 |
| 21 | N | -0.584 | 0.000 | 0.000 | 0.000 |
| 22 | M | -0.276 | 0.000 | 0.000 | 0.000 |
| 23 | G | -0.492 | 0.000 | 0.000 | 0.000 |
| 24 | S | 0.133 | 0.418 | 0.000 | 0.119 |
| 25 | R | 0.182 | 0.418 | 0.000 | 0.119 |
| 26 | I | 0.043 | 0.418 | 0.000 | 0.119 |
| 27 | Y | -0.180 | 0.000 | 0.000 | 0.000 |
| 28 | Q | 0.418 | 0.438 | 0.000 | 0.418 |
| 29 | E | -0.228 | 0.000 | 0.000 | 0.000 |
| 30 | F | -0.141 | 0.000 | 0.000 | 0.000 |
| 31 | E | 0.073 | 1.256 | 0.000 | 0.294 |
| 32 | V | 0.674 | 1.256 | 0.000 | 0.294 |
| 33 | T | 0.257 | 1.256 | 0.000 | 0.294 |
| 34 | V | 0.172 | 1.256 | 0.000 | 0.294 |
| 35 | P | -0.206 | 0.000 | 0.000 | 0.000 |
| 36 | D | 0.190 | 0.210 | 0.000 | 0.190 |
| 37 | S | -0.160 | 0.000 | 0.000 | 0.000 |
| 38 | I | 0.152 | 0.000 | 0.000 | 0.000 |
| 39 | T | -0.002 | 0.056 | 0.000 | -0.002 |
| 40 | S | -0.002 | 0.056 | 0.000 | -0.002 |

B

Small molecular weight CD 109-based peptides

| | | |
|---|---|---|
| X | 680-719 | LGSSPHVRKHFPETWIWLDTNMGSRIYQEFEVTVPDSITS (SEQ ID NO: 1) |
| X-1 | 692-719 | ETWIWLDTNMGSRIYQEFEVTVPDSITS (SEQ ID NO: 2) |
| X-2 | 692-712 | ETWIWLDTNMGSRIYQEFEVT (SEQ ID NO: 6) |
| X-3 | 697-712 | LDTNMGSRIYQEFEVT (SEQ ID NO: 8) |
| X-4 | 702-712 | GSRIYQEFEVT (SEQ ID NO: 9) |
| | | |
| P21 | 692-712 | ETWIWLDTNMGSRIYQEFEVT (SEQ ID NO: 6) |
| P16 | 692-707 | ETWIWLDTNMGSRIYQ (SEQ ID NO: 5) |
| P11 | 692-702 | ETWIWLDTNMG (SEQ ID NO: 4) |
| | | |
| Scrambled P16-1 | | ILNTWMDSTQIGYRWE (SEQ ID NO: 10) |
| Scrambled P16-2 | | WINMDTGWLIEQRYTS (SEQ ID NO: 7) |

Figure 15
A
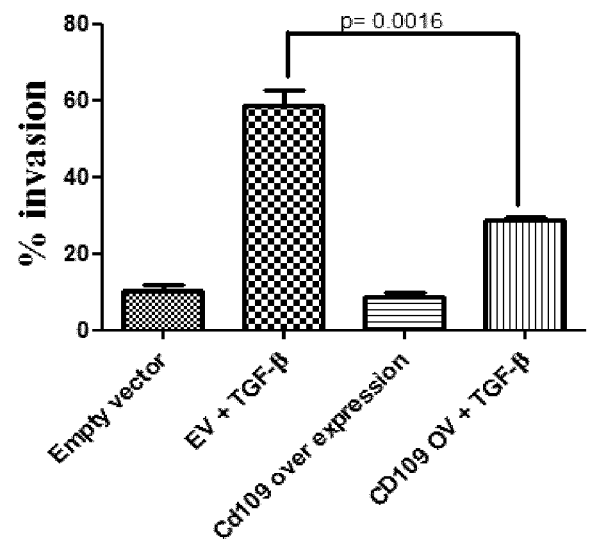
B
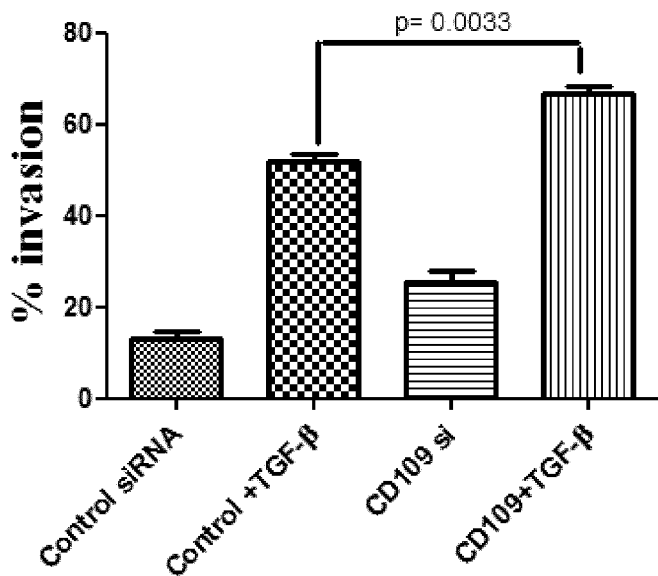

Figure 16
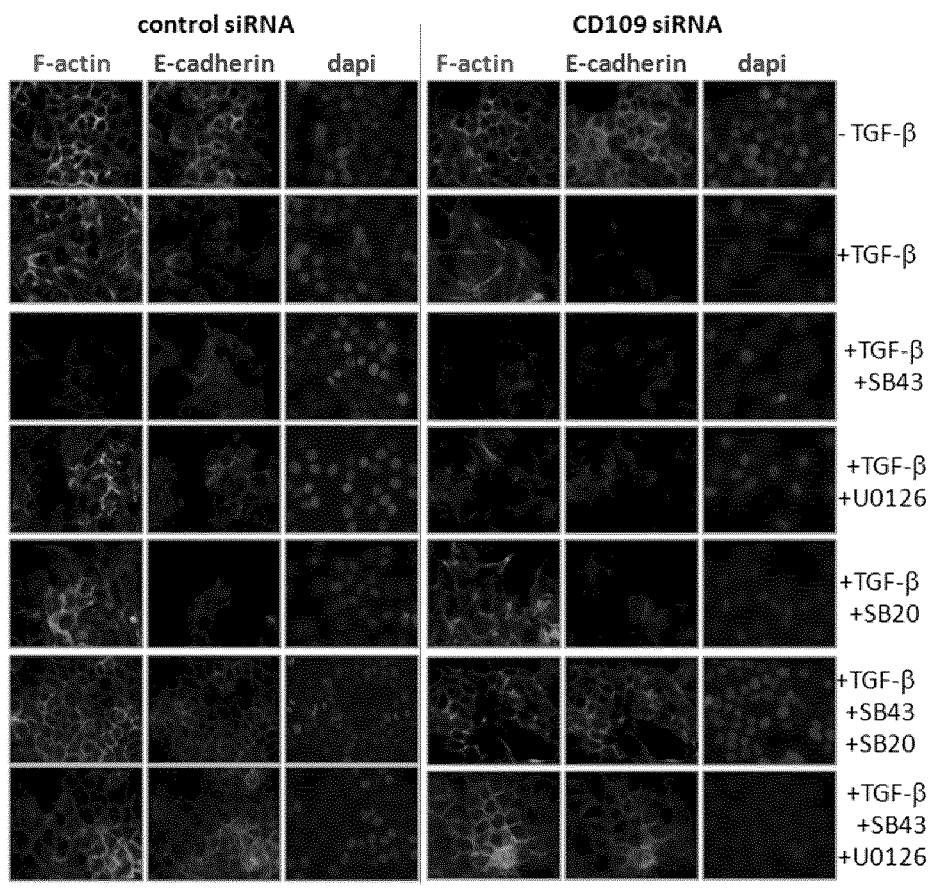
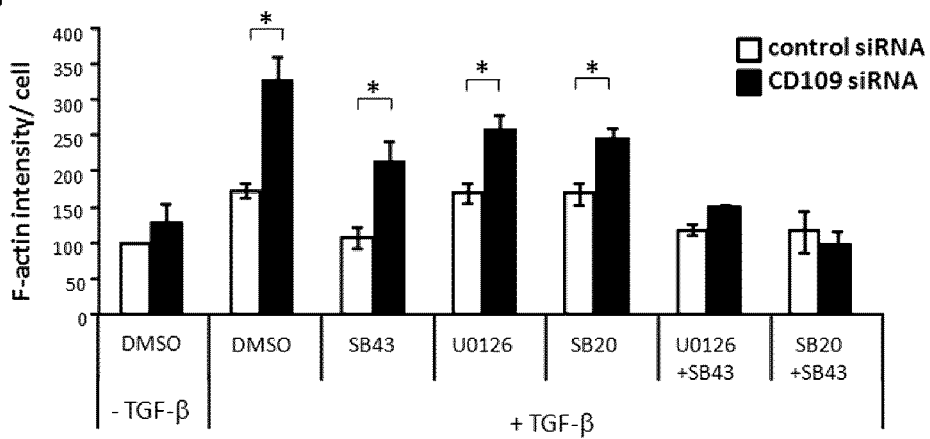

Figure 21
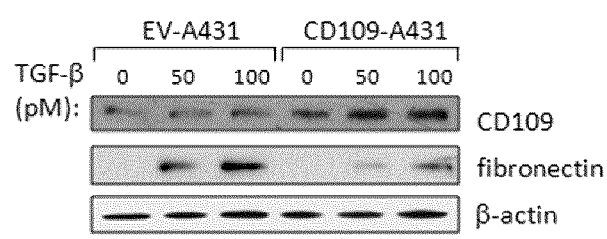 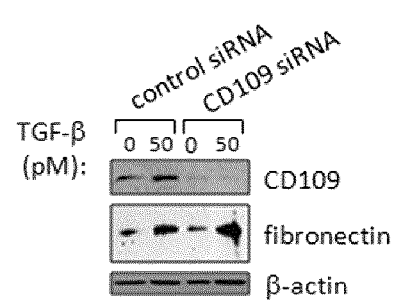

Buffer

TGF-

P16.2/TGF-β

P16/TGF-β

PA/TGF-β

CD109/TGF-β

SEQUENCE LISTING

<160> NUMBER OF SEQ ID NOS: 26

<210> SEQ ID NO 1
<211> LENGTH: 40
<212> TYPE: PRT
<213> ORGANISM: Artificial Sequence
<220> FEATURE:
<223> OTHER INFORMATION: Peptide X

<400> SEQUENCE: 1

Leu Gly Ser Ser Pro His Val Arg Lys His Phe Pro Glu Thr Trp Ile
1               5                   10                  15

Trp Leu Asp Thr Asn Met Gly Ser Arg Ile Tyr Gln Glu Phe Glu Val
                20                  25                  30

Thr Val Pro Asp Ser Ile Thr Ser
            35                  40

<210> SEQ ID NO 2
<211> LENGTH: 28
<212> TYPE: PRT
<213> ORGANISM: Artificial Sequence
<220> FEATURE:
<223> OTHER INFORMATION: Peptide X-1

<400> SEQUENCE: 2

Glu Thr Trp Ile Trp Leu Asp Thr Asn Met Gly Ser Arg Ile Tyr Gln
1               5                   10                  15

Glu Phe Glu Val Thr Val Pro Asp Ser Ile Thr Ser
                20                  25

<210> SEQ ID NO 3
<211> LENGTH: 161
<212> TYPE: PRT
<213> ORGANISM: Artificial Sequence
<220> FEATURE:
<223> OTHER INFORMATION: Peptide A

<400> SEQUENCE: 3

Thr Met Glu Asn Val Val His Glu Leu Glu Leu Tyr Asn Thr Gly Tyr
1               5                   10                  15

Tyr Leu Gly Met Phe Met Asn Ser Phe Ala Val Phe Gln Glu Cys Gly
                20                  25                  30

Leu Trp Val Leu Thr Asp Ala Asn Leu Thr Lys Asp Tyr Ile Asp Gly
            35                  40                  45

Val Tyr Asp Asn Ala Glu Tyr Ala Glu Arg Phe Met Glu Glu Asn Glu
50                  55                  60

Gly His Ile Val Asp Ile His Asp Phe Ser Leu Gly Ser Ser Pro His
65                  70                  75                  80

Val Arg Lys His Phe Pro Glu Thr Trp Ile Trp Leu Asp Thr Asn Met
                85                  90                  95

Gly Ser Arg Ile Tyr Gln Glu Phe Glu Val Thr Val Pro Asp Ser Ile
            100                 105                 110

Thr Ser Trp Val Ala Thr Gly Phe Val Ile Ser Glu Asp Leu Gly Leu
        115                 120                 125

Gly Leu Thr Thr Thr Pro Val Glu Leu Gln Ala Phe Gln Pro Phe Phe
    130                 135                 140

Ile Phe Leu Asn Leu Pro Tyr Ser Val Ile Arg Gly Glu Glu Phe Ala
145                 150                 155                 160

Leu

<210> SEQ ID NO 4
<211> LENGTH: 11
<212> TYPE: PRT
<213> ORGANISM: Artificial Sequence
<220> FEATURE:
<223> OTHER INFORMATION: Peptide P11

<400> SEQUENCE: 4

Glu Thr Trp Ile Trp Leu Asp Thr Asn Met Gly
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Peptide P16

<400> SEQUENCE: 5

Glu Thr Trp Ile Trp Leu Asp Thr Asn Met Gly Ser Arg Ile Tyr Gln
1               5                   10                  15

<210> SEQ ID NO 6
<211> LENGTH: 21
<212> TYPE: PRT
<213> ORGANISM: Artificial Sequence
<220> FEATURE:
<223> OTHER INFORMATION: Peptide P21/X-2

<400> SEQUENCE: 6

Glu Thr Trp Ile Trp Leu Asp Thr Asn Met Gly Ser Arg Ile Tyr Gln
1               5                   10                  15

Glu Phe Glu Val Thr
            20

<210> SEQ ID NO 7
<211> LENGTH: 16
<212> TYPE: PRT
<213> ORGANISM: Artificial Sequence
<220> FEATURE:
<223> OTHER INFORMATION: Peptide P16-2

<400> SEQUENCE: 7

Trp Ile Asn Met Asp Thr Gly Trp Leu Ile Glu Gln Arg Tyr Thr Ser
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Peptide X-3

<400> SEQUENCE: 8

Leu Asp Thr Asn Met Gly Ser Arg Ile Tyr Gln Glu Phe Glu Val Thr
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: Peptide X-4

<400> SEQUENCE: 9

Gly Ser Arg Ile Tyr Gln Glu Phe Glu Val Thr

```
<210> SEQ ID NO 10
<211> LENGTH: 16
<212> TYPE: PRT
<213> ORGANISM: Artificial Sequence
<220> FEATURE:
<223> OTHER INFORMATION: Peptide P16-1

<400> SEQUENCE: 10

Ile Leu Asn Thr Trp Met Asp Ser Thr Gln Ile Gly Tyr Arg Trp Glu
1               5                   10                  15

<210> SEQ ID NO 11
<211> LENGTH: 6
<212> TYPE: PRT
<213> ORGANISM: Artificial Sequence
<220> FEATURE:
<223> OTHER INFORMATION: TGF-beta binding motif

<400> SEQUENCE: 11

Glu Thr Trp Ile Trp Leu
1               5

<210> SEQ ID NO 12
<211> LENGTH: 12
<212> TYPE: PRT
<213> ORGANISM: Artificial Sequence
<220> FEATURE:
<223> OTHER INFORMATION: Peptide P12

<400> SEQUENCE: 12

Glu Thr Trp Ile Trp Leu Asp Thr Asn Met Gly Ser
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Peptide P13

<400> SEQUENCE: 13

Glu Thr Trp Ile Trp Leu Asp Thr Asn Met Gly Ser Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Peptide P14

<400> SEQUENCE: 14

Glu Thr Trp Ile Trp Leu Asp Thr Asn Met Gly Ser Arg Ile
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Peptide P15

<400> SEQUENCE: 15

Glu Thr Trp Ile Trp Leu Asp Thr Asn Met Gly Ser Arg Ile Tyr
1               5                   10                  15
```

```
<210> SEQ ID NO 16
<211> LENGTH: 16
<212> TYPE: PRT
<213> ORGANISM: Artificial Sequence
<220> FEATURE:
<223> OTHER INFORMATION: Peptide of formula I
<220> FEATURE:
<221> NAME/KEY: VARIANT
<222> LOCATION: (12)..(16)
<223> OTHER INFORMATION: Xaa is present or absent and can be any amino
      acid

<400> SEQUENCE: 16

Glu Thr Trp Ile Trp Leu Asp Thr Asn Met Gly Xaa Xaa Xaa Xaa Xaa
1               5                   10                  15

<210> SEQ ID NO 17
<211> LENGTH: 121
<212> TYPE: PRT
<213> ORGANISM: Artificial Sequence
<220> FEATURE:
<223> OTHER INFORMATION: Peptide Y

<400> SEQUENCE: 17

Thr Met Glu Asn Val Val His Glu Leu Glu Leu Tyr Asn Thr Gly Tyr
1               5                   10                  15

Tyr Leu Gly Met Phe Met Asn Ser Phe Ala Val Phe Gln Glu Cys Gly
            20                  25                  30

Leu Trp Val Leu Thr Asp Ala Asn Leu Thr Lys Asp Tyr Ile Asp Gly
        35                  40                  45

Val Tyr Asp Asn Ala Glu Tyr Ala Glu Arg Phe Met Glu Glu Asn Glu
    50                  55                  60

Gly His Ile Val Asp Ile His Asp Phe Ser Leu Gly Ser Ser Pro His
65                  70                  75                  80

Val Arg Lys His Phe Pro Glu Thr Trp Ile Trp Leu Asp Thr Asn Met
                85                  90                  95

Gly Ser Arg Ile Tyr Gln Glu Phe Glu Val Thr Val Pro Asp Ser Ile
            100                 105                 110

Thr Ser Trp Val Ala Thr Gly Phe Val
        115                 120

<210> SEQ ID NO 18
<211> LENGTH: 121
<212> TYPE: PRT
<213> ORGANISM: Artificial Sequence
<220> FEATURE:
<223> OTHER INFORMATION: Peptide Z

<400> SEQUENCE: 18

Leu Thr Lys Asp Tyr Ile Asp Gly Val Tyr Asp Asn Ala Glu Tyr Ala
1               5                   10                  15

Glu Arg Phe Met Glu Glu Asn Glu Gly His Ile Val Asp Ile His Asp
            20                  25                  30

Phe Ser Leu Gly Ser Ser Pro His Val Arg Lys His Phe Pro Glu Thr
        35                  40                  45

Trp Ile Trp Leu Asp Thr Asn Met Gly Ser Arg Ile Tyr Gln Glu Phe
    50                  55                  60

Glu Val Thr Val Pro Asp Ser Ile Thr Ser Trp Val Ala Thr Gly Phe
65                  70                  75                  80

Val Ile Ser Glu Asp Leu Gly Leu Gly Leu Thr Thr Thr Pro Val Glu
```

```
                    85                  90                  95

Leu Gln Ala Phe Gln Pro Phe Phe Ile Phe Leu Asn Leu Pro Tyr Ser
                100                 105                 110

Val Ile Arg Gly Glu Glu Phe Ala Leu
            115                 120

<210> SEQ ID NO 19
<211> LENGTH: 107
<212> TYPE: PRT
<213> ORGANISM: Artificial Sequence
<220> FEATURE:
<223> OTHER INFORMATION: Peptide B

<400> SEQUENCE: 19

Thr Met Glu Asn Val Val His Glu Leu Glu Leu Tyr Asn Thr Gly Tyr
1               5                   10                  15

Tyr Leu Gly Met Phe Met Asn Ser Phe Ala Val Phe Gln Glu Cys Gly
                20                  25                  30

Leu Trp Val Leu Thr Asp Ala Asn Leu Thr Lys Asp Tyr Ile Asp Gly
            35                  40                  45

Val Tyr Asp Asn Ala Glu Tyr Ala Glu Arg Phe Met Glu Glu Asn Glu
    50                  55                  60

Gly His Ile Val Asp Ile His Asp Phe Ser Leu Gly Ser Ser Pro His
65                  70                  75                  80

Val Arg Lys His Phe Pro Glu Thr Trp Ile Trp Leu Asp Thr Asn Met
                85                  90                  95

Gly Ser Arg Ile Tyr Gln Glu Phe Glu Val Thr
                100                 105

<210> SEQ ID NO 20
<211> LENGTH: 68
<212> TYPE: PRT
<213> ORGANISM: Artificial Sequence
<220> FEATURE:
<223> OTHER INFORMATION: Peptide E

<400> SEQUENCE: 20

Leu Thr Lys Asp Tyr Ile Asp Gly Val Tyr Asp Asn Ala Glu Tyr Ala
1               5                   10                  15

Glu Arg Phe Met Glu Glu Asn Glu Gly His Ile Val Asp Ile His Asp
                20                  25                  30

Phe Ser Leu Gly Ser Ser Pro His Val Arg Lys His Phe Pro Glu Thr
            35                  40                  45

Trp Ile Trp Leu Asp Thr Asn Met Gly Ser Arg Ile Tyr Gln Glu Phe
    50                  55                  60

Glu Val Thr Val
65

<210> SEQ ID NO 21
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)..(1)
<223> OTHER INFORMATION: Xaa is Asp or Glu
<220> FEATURE:
<221> NAME/KEY: VARIANT
<222> LOCATION: (2)..(2)
<223> OTHER INFORMATION: Xaa is Ser, Thr, Asn or Gln
```

```
<220> FEATURE:
<221> NAME/KEY: VARIANT
<222> LOCATION: (3)..(3)
<223> OTHER INFORMATION: Xaa is Ala, Ile, Leu, Met, Phe, Trp, or Tyr
<220> FEATURE:
<221> NAME/KEY: VARIANT
<222> LOCATION: (4)..(4)
<223> OTHER INFORMATION: Xaa is Ala, Ile, Leu, Met, Phe, Trp, or Tyr
<220> FEATURE:
<221> NAME/KEY: VARIANT
<222> LOCATION: (5)..(5)
<223> OTHER INFORMATION: Xaa is Ala, Ile, Leu, Met, Phe, Trp, or Tyr
<220> FEATURE:
<221> NAME/KEY: VARIANT
<222> LOCATION: (6)..(6)
<223> OTHER INFORMATION: Xaa is Ala, Ile, Leu, Met, Phe, Trp, or Tyr
<220> FEATURE:
<221> NAME/KEY: VARIANT
<222> LOCATION: (7)..(7)
<223> OTHER INFORMATION: Xaa is Asp or Glu
<220> FEATURE:
<221> NAME/KEY: VARIANT
<222> LOCATION: (8)..(8)
<223> OTHER INFORMATION: Xaa is Ser, Thr, Asn, or Gln
<220> FEATURE:
<221> NAME/KEY: VARIANT
<222> LOCATION: (9)..(9)
<223> OTHER INFORMATION: Xaa is Ser, Thr, Asn or Gln
<220> FEATURE:
<221> NAME/KEY: VARIANT
<222> LOCATION: (10)..(10)
<223> OTHER INFORMATION: Xaa is Ala, Ile, Leu, Met, Phe, Trp, or Tyr
<220> FEATURE:
<221> NAME/KEY: VARIANT
<222> LOCATION: (11)..(11)
<223> OTHER INFORMATION: Xaa is Ala, Val, or Gly

<400> SEQUENCE: 21

Xaa Xaa Xaa Xaa Xaa Xaa Xaa Xaa Xaa Xaa Xaa
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Synthetic construct

<400> SEQUENCE: 22

Glu Thr Trp Ile Trp Leu Asp Thr Asn Met Gly Ser Arg Ile Tyr Gln
1               5                   10                  15

Glu

<210> SEQ ID NO 23
<211> LENGTH: 18
<212> TYPE: PRT
<213> ORGANISM: Artificial Sequence
<220> FEATURE:
<223> OTHER INFORMATION: Synthetic construct

<400> SEQUENCE: 23

Glu Thr Trp Ile Trp Leu Asp Thr Asn Met Gly Ser Arg Ile Tyr Gln
1               5                   10                  15

Glu Phe

<210> SEQ ID NO 24
<211> LENGTH: 19
<212> TYPE: PRT
<213> ORGANISM: Artificial Sequence
<220> FEATURE:
<223> OTHER INFORMATION: Synthetic construct
```

```
<400> SEQUENCE: 24

Glu Thr Trp Ile Trp Leu Asp Thr Asn Met Gly Ser Arg Ile Tyr Gln
1               5                   10                  15
Glu Phe Glu

<210> SEQ ID NO 25
<211> LENGTH: 20
<212> TYPE: PRT
<213> ORGANISM: Artificial Sequence
<220> FEATURE:
<223> OTHER INFORMATION: Synthetic construct

<400> SEQUENCE: 25

Glu Thr Trp Ile Trp Leu Asp Thr Asn Met Gly Ser Arg Ile Tyr Gln
1               5                   10                  15
Glu Phe Glu Val
            20

<210> SEQ ID NO 26
<211> LENGTH: 16
<212> TYPE: PRT
<213> ORGANISM: Artificial Sequence
<220> FEATURE:
<223> OTHER INFORMATION: Peptide of Formula III
<220> FEATURE:
<221> NAME/KEY: misc_feature
<222> LOCATION: (12)..(12)
<223> OTHER INFORMATION: Xaa can be any naturally occurring amino acid

<400> SEQUENCE: 26

Glu Thr Trp Ile Trp Leu Asp Thr Asn Met Gly Xaa Arg Ile Tyr Gln
1               5                   10                  15
```

PEPTIDIC TGF-BETA ANTAGONISTS

INCORPORATION OF SEQUENCE LISTING

A computer readable form of the Sequence Listing "P59621US00_SequenceListing.txt" (12,228 bytes), submitted via EFS-WEB and created on May 25, 2020, is herein incorporated by reference.

FIELD OF THE INVENTION

The present invention relates to peptides capable of antagonizing TGF-β's biological activity as well as their use for preventing or treating fibrosis and cellular transformation/proliferative-associated disorders, such as cancer.

BACKGROUND OF THE INVENTION

Transforming growth factor-β (TGF-β) is a 25 kDa multifunctional growth factor which plays a central role in the wound healing process. It is an important regulator of the immune response, angiogenesis, reepithelialization, extracellular matrix protein synthesis and remodeling. During wound healing, re-epithelialization initiates the repair process, which is characterized by recruitment of epidermal stem cells, keratinocyte proliferation, and the formation of an epithelial tongue of migrating keratinocytes at the wound edge. TGF-β is chemotactic to keratinocytes and induces the expression of integrins on the migrating epithelium. In spite of its pro-migratory effect on keratinocytes, TGF-β is a potent inhibitor of epithelial cell proliferation in vitro and in vivo. In addition, TGF-β is a potent pro-fibrotic factor that stimulates fibroblasts to undergo differentiation into myofibroblasts, which secrete extracellular matrix proteins and regulate wound contraction. TGF-β also plays a significant role in cancer progression by suppressing the immune system and stimulating angiogenesis, as well as by increasing metastasis and enhancing 'stemness' of cancer stem cells (for example, the capacity to self-renew and differentiate). Antagonists of TGF-β could thus be used to mitigate fibrosis in general, and specifically aberrant would healing, or slow down the progression of some forms of cancer.

There remains a need for soluble, low-molecular weight peptide antagonists of TGF-β, and particularly for peptides capable of exhibiting inhibitory activity without aggregating in aqueous solution. Such peptidic antagonists could be used for the prevention, treatment and/or alleviation of symptoms of fibrosis and/or cancer.

SUMMARY OF THE INVENTION

The invention provides TGF-β antagonists containing a low-molecular weight TGF-β-binding peptide. The TGF-β-binding peptide is capable of establishing an inhibitory intermolecular interaction with TGF-β, which can manifest in attenuated TGF-β signaling, for instance, in the form of reduced expression of genes under the control of transcription factors activated by TGF-β signal transduction, such as Smad3. The TGF-β-binding peptide may be capable of attenuating the expression of proteins involved in the fibrotic response, such as fibronectin, plasminogen activator inhibitor-1 (PAI-1), and connective tissue growth factor (CTGF). Due to their capacity for inhibiting TGF-β activity, the TGF-β-binding peptides described herein can be used as TGF-β antagonists for the treatment of a variety of pathological conditions, including fibrosis, autoimmune diseases, and cancers, among others. The TGF-β antagonists described herein may contain a TGF-β-binding peptide and, for instance, one or more additional elements that do not interfere with the ability of the TGF-β-binding peptide to establish intermolecular contacts with TGF-β. In some embodiments, the TGF-β antagonist consists of the TGF-β-binding peptide, which is necessary and sufficient for inhibitory activity, and does not contain any additional elements.

In a first aspect, the invention features a transforming growth factor-β (TGF-β) antagonist comprising a TGF-β-binding peptide comprising the amino acid sequence of formula I:

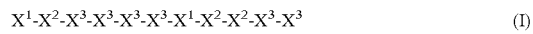
$$X^1\text{-}X^2\text{-}X^3\text{-}X^3\text{-}X^3\text{-}X^3\text{-}X^1\text{-}X^2\text{-}X^2\text{-}X^3\text{-}X^3 \tag{I}$$

wherein each $X^1$ is independently an amino acid comprising an anionic side-chain at physiological pH;

each $X^2$ is independently an amino acid comprising a polar, uncharged side-chain at physiological pH;

each $X^3$ is independently an amino acid comprising a nonpolar side-chain; and

"-" represents a peptide bond between adjacent amino acid residues. In some embodiments, the TGF-β-binding peptide contains fewer than 161 amino acids. In some embodiments, the TGF-β-binding peptide contains fewer than 150 amino acids (e.g., fewer than 145 amino acids, 140 amino acids, 135 amino acids, 130 amino acids, 125 amino acids, 120 amino acids, 115 amino acids, 110 amino acids, 105 amino acids, 100 amino acids, 95 amino acids, 90 amino acids, 85 amino acids, 80 amino acids, 75 amino acids, 70 amino acids, 65 amino acids, 60 amino acids, 55 amino acids, 50 amino acids, 45 amino acids, 40 amino acids, 35 amino acids, 30 amino acids, 25 amino acids, or less). In some embodiments, the TGF-β-binding peptide contains 21 amino acids. In some embodiments, the TGF-β-binding peptide contains fewer than 20 amino acids (e.g., 19 amino acids, 18 amino acids, 17 amino acids, 16 amino acids, 15 amino acids, 14 amino acids, 13 amino acids, 12 amino acids, or 11 amino acids). In some embodiments, the TGF-β-binding peptide contains 16 amino acids. In some embodiments, the TGF-β-binding peptide contains 11 amino acids.

In some embodiments, the TGF-β-binding peptide contains the amino acid sequence of formula II:

$$\text{ETWIWLDTNMG-Xaa}_1\text{-Y} \tag{II}$$

wherein $Xaa_1$ is any naturally-occurring or non-natural amino acid; and

Y is a peptide comprising between 0 and 9 amino acid residues.

In some embodiments, $Xaa_1$ is a naturally-occurring amino acid.

In some embodiments, $Xaa_1$ is an amino acid containing a polar, uncharged side-chain at physiological pH, such as a serine, threonine, glutamine, asparagine, or tyrosine residue. In some embodiments, $Xaa_1$ a serine residue. In some embodiments, $Xaa_1$ is a tyrosine residue.

In some embodiments, the TGF-β-binding peptide contains the amino acid sequence of ETWIWLDTNMGS (SEQ ID NO: 12). In some embodiments, the TGF-β-binding peptide consists of the amino acid sequence of ETWIWLDTNMGS (SEQ ID NO: 12). In some embodiments, the TGF-β antagonist consists of the amino acid sequence of ETWIWLDTNMGS (SEQ ID NO: 12).

In some embodiments, Y contains a peptide of the formula (IIa):

$$\text{-Xaa}_2 \tag{IIa}$$

wherein "-" is as defined; and

Xaa$_2$ is any naturally-occurring or non-natural amino acid.

In some embodiments, Xaa$_2$ is a naturally-occurring amino acid.

In some embodiments, Xaa$_2$ is an amino acid containing a cationic side-chain at physiological pH, such as a lysine, arginine, or histidine residue. In some embodiments, Xaa$_2$ is an arginine residue.

In some embodiments, the TGF-β-binding peptide contains the amino acid sequence of ETWIWLDTNMGSR (SEQ ID NO: 13). In some embodiments, the TGF-β-binding peptide consists of the amino acid sequence of ETWIWLDTNMGSR (SEQ ID NO: 13). In some embodiments, the TGF-β-binding antagonist consists of the amino acid sequence of ETWIWLDTNMGSR (SEQ ID NO: 13).

In some embodiments, Y contains a peptide of the formula (IIb):

-Xaa$_2$-Xaa$_3$   (IIb)

wherein "-" and Xaa$_2$ are as defined; and

Xaa$_3$ is a naturally-occurring or non-natural amino acid.

In some embodiments, Xaa$_3$ is a naturally-occurring amino acid.

In some embodiments, Xaa$_3$ is an amino acid containing a non-polar side-chain, such as a leucine, isoleucine, valine, methionine, tryptophan, or phenylalanine residue. In some embodiments, Xaa$_3$ is an isoleucine residue. In some embodiments, the TGF-β-binding peptide contains the amino acid sequence of ETWIWLDTNMGSRI (SEQ ID NO: 14). In some embodiments, the TGF-β-binding peptide consists of the amino acid sequence of ETWIWLDTNMGSRI (SEQ ID NO: 14). In some embodiments, the TGF-β antagonist consists of the amino acid sequence of ETWIWLDTNMGSRI (SEQ ID NO: 14).

In some embodiments, Y contains a peptide of the formula (IIc):

-Xaa$_2$-Xaa$_3$-Xaa$_4$   (IIc)

wherein "-", Xaa$_2$ and Xaa$_3$ are as defined; and

Xaa$_4$ is a naturally-occurring or non-natural amino acid.

In some embodiments, Xaa$_4$ is a naturally-occurring amino acid.

In some embodiments, Xaa$_4$ is an amino acid containing an aromatic side-chain, such as a tryptophan, tyrosine, or phenylalanine residue. In some embodiments, Xaa$_4$ is a tyrosine residue. In some embodiments, the TGF-β-binding peptide contains the amino acid sequence of ETWIWLDTNMGSRIY (SEQ ID NO: 15). In some embodiments, the TGF-β-binding peptide consists of the amino acid sequence of ETWIWLDTNMGSRIY (SEQ ID NO: 15). In some embodiments, the TGF-β antagonist consists of the amino acid sequence of ETWIWLDTNMGSRIY (SEQ ID NO: 15).

In some embodiments, Y contains a peptide of the formula (IId):

-Xaa$_2$-Xaa$_3$-Xaa$_4$-Xaa$_5$   (IId)

wherein "-", Xaa$_2$, Xaa3, and Xaa$_4$ are as defined; and

Xaa$_5$ is a naturally-occurring or non-natural amino acid.

In some embodiments, Xaa$_5$ is a naturally-occurring amino acid.

In some embodiments, Xaa$_5$ is an amino acid comprising a polar, uncharged side-chain at physiological pH, such as a serine, threonine, glutamine, asparagine, or tyrosine residue. In some embodiments, Xaa$_5$ is a glutamine residue. In some embodiments, the TGF-β-binding peptide contains the amino acid sequence of ETWIWLDTNMGSRIYQ (SEQ ID NO: 5). In some embodiments, the TGF-β-binding peptide consists of the amino acid sequence of ETWIWLDTNMGSRIYQ (SEQ ID NO: 5). In some embodiments, the TGF-β antagonist consists of the amino acid sequence of ETWIWLDTNMGSRIYQ (SEQ ID NO: 5).

In some embodiments, Y contains a peptide of the formula (IIe):

-Xaa$_2$-Xaa$_3$-Xaa$_4$-Xaa$_5$-Xaa$_6$   (IIe)

wherein "-", Xaa$_2$, Xaa$_3$, Xaa$_4$, and Xaa$_5$ are as defined; and

Xaa$_6$ is a naturally-occurring or non-natural amino acid.

In some embodiments, Xaa$_6$ is a naturally-occurring amino acid.

In some embodiments, Xaa$_6$ is an amino acid comprising an anionic side-chain at physiological pH, such as an aspartate or glutamate residue. In some embodiments, Xaa$_6$ is a glutamate residue. In some embodiments, the TGF-β-binding peptide contains the amino acid sequence of ETWIWLDTNMGSRIYQE (SEQ ID NO: 22). In some embodiments, the TGF-β-binding peptide consists of the amino acid sequence of ETWIWLDTNMGSRIYQE (SEQ ID NO: 22). In some embodiments, the TGF-β antagonist consists of the amino acid sequence of ETWIWLDTNMGSRIYQE (SEQ ID NO: 22).

In some embodiments, Y contains a peptide of the formula (IIf):

-Xaa$_2$-Xaa$_3$-Xaa$_4$-Xaa$_5$-Xaa$_6$-Xaa$_7$   (IIf)

wherein "-", Xaa$_2$, Xaa$_3$, Xaa$_4$, Xaa$_5$, and Xaa$_6$ are as defined; and Xaa$_7$ is a naturally-occurring or non-natural amino acid.

In some embodiments, Xaa$_7$ is a naturally-occurring amino acid.

In some embodiments, Xaa$_7$ is an amino acid comprising an aromatic side-chain, such as a tryptophan, tyrosine, or phenylalanine residue. In some embodiments, Xaa$_7$ is a phenylalanine residue. In some embodiments, the TGF-β-binding peptide contains the amino acid sequence of ETWIWLDTNMGSRIYQEF (SEQ ID NO: 23). In some embodiments, the TGF-β-binding peptide consists of the amino acid sequence of ETWIWLDTNMGSRIYQEF (SEQ ID NO: 23). In some embodiments, the TGF-β antagonist consists of the amino acid sequence of (SEQ ID NO: 23)
ETWIWLDTNMGSRIYQEF.

In some embodiments, Y contains a peptide of the formula (IIg):

-Xaa$_2$-Xaa$_3$-Xaa$_4$-Xaa$_5$-Xaa$_6$-Xaa$_7$-Xaa$_8$   (IIg)

wherein "-", Xaa$_2$, Xaa$_3$, Xaa$_4$, Xaa$_5$, Xaa$_6$, and Xaa$_7$ are as defined; and Xaa$_8$ is a naturally-occurring or non-natural amino acid.

In some embodiments, Xaa$_8$ is a naturally-occurring amino acid.

In some embodiments, Xaa$_8$ is an amino acid comprising an anionic side-chain at physiological pH, such as an aspartate or glutamate residue. In some embodiments, Xaa$_8$ is a glutamate residue. In some embodiments, the TGF-β-binding peptide contains the amino acid sequence of ETWIWLDTNMGSRIYQEFE (SEQ ID NO: 24). In some embodiments, the TGF-β-binding peptide consists of the amino acid sequence of ETWIWLDTNMGSRIYQEFE (SEQ ID NO:

24). In some embodiments, the TGF-β antagonist consists of the amino acid sequence of

ETWIWLDTNMGSRIYQEFE. (SEQ ID NO: 24)

In some embodiments, Y contains a peptide of the formula (IIh):

-Xaa$_2$-Xaa$_3$-Xaa$_4$-Xaa$_5$-Xaa$_6$-Xaa$_7$-Xaa$_8$-Xaa$_9$ (IIh)

wherein "-", Xaa$_2$, Xaa$_3$, Xaa$_4$, Xaa$_5$, Xaa$_6$, Xaa$_7$, and Xaa$_8$ are as defined; and Xaa$_9$ is a naturally-occurring or non-natural amino acid.

In some embodiments, Xaa$_9$ is a naturally-occurring amino acid.

In some embodiments, Xaa$_9$ is an amino acid containing a nonpolar side-chain at physiological pH, such as a leucine, isoleucine, valine, methionine, tryptophan, or phenylalanine residue. In some embodiments, Xaa$_9$ is a valine residue. In some embodiments, the TGF-β-binding peptide contains the amino acid sequence of ETWIWLDTNMGSRIYQEFEV (SEQ ID NO: 25). In some embodiments, the TGF-β-binding peptide consists of the amino acid sequence of ETWIWLDTNMGSRIYQEFEV (SEQ ID NO: 25). In some embodiments, the TGF-β antagonist consists of the amino acid sequence of ETWIWLDTNMGSRIYQEFEV (SEQ ID NO: 25).

In some embodiments, Y contains a peptide of the formula (IIi):

-Xaa$_2$-Xaa$_3$-Xaa$_4$-Xaa$_5$-Xaa$_6$-Xaa$_7$-Xaa$_8$-Xaa$_9$-Xaa$_{10}$ (IIi)

wherein "-", Xaa$_2$, Xaa$_3$, Xaa$_4$, Xaa$_5$, Xaa$_6$, Xaa$_7$, Xaa$_8$, and Xaa$_9$ are as defined; and Xaa$_{10}$ is a naturally-occurring or non-natural amino acid.

In some embodiments, Xaa$_{10}$ is a naturally-occurring amino acid.

In some embodiments, Xaa$_{10}$ is an amino acid comprising a polar, uncharged side-chain at physiological pH, such as a serine, threonine, glutamine, asparagine, or tyrosine residue. In some embodiments, Xaa$_{10}$ is a threonine residue. In some embodiments, the TGF-β-binding peptide contains the amino acid sequence of ETWIWLDTNMGSRIYQEFEVT (SEQ ID NO: 6). In some embodiments, the TGF-β-binding peptide consists of the amino acid sequence of ETWIWLDTNMGSRIYQEFEVT (SEQ ID NO: 6). In some embodiments, the TGF-β antagonist consists of the amino acid sequence of ETWIWLDTNMGSRIYQEFEVT (SEQ ID NO: 6).

In some embodiments, the TGF-β-binding peptide is a linear peptide, for instance, containing amine and carboxyl substituents at the N- and C-termini of the peptide, respectively, or containing acyl (e.g., acetyl) and carboxamide substituents at the N- and C-termini of the peptide, respectively. In some embodiments, the TGF-β-binding peptide is a cyclic peptide. For instance, the TGF-β-binding peptide may be covalently bound to a cysteine residue at each of the N-terminus and the C-terminus of the TGF-β-binding peptide. The cysteine residues can be covalently bound to one another, for example, by a disulfide bond. In some embodiments, the cysteine residues are covalently bound to one another by way of a linker, for instance, through thioether bonds. In some embodiments, the linker contains an alkyl, aryl, heteroaryl, cycloalkyl, or heterocycloalkyl moiety. In some embodiments, the TGF-β-binding peptide is a head-to-tail cyclic peptide.

In some embodiments, the TGF-β antagonist contains a multimer, such as a dimer that includes two copies of the TGF-β-binding peptide. Each of the copies of the TGF-β-binding peptide cab be covalently bound to one another, for instance, by a disulfide bond or thioether bond.

In some embodiments, the TGF-β-binding peptide does not aggregate in aqueous solution. Aggregation of the TGF-β-binding peptide can be determined, for example, by gel electrophoresis or by size-exclusion chromatography as described herein. In some embodiments, the aqueous solution contains less than 5% dimethylsulfoxide (DMSO). For instance, the aqueous solution may contain less than 4%, 3%, 2%, or 1% DMSO. In some embodiments, the aqueous solution is substantially free of DMSO (for example, DMSO cannot be detected in the aqueous solution by conventional spectroscopic or mass spectrometry methods known in the art, such as by nuclear magnetic resonance (NMR) spectroscopy, infrared spectroscopy, UV-Vis spectroscopy, or electrospray ionization mass spectrometry, among others).

In some embodiments, the TGF-β antagonist inhibits binding of TGF-β to the surface of a keratinocyte. In some embodiments, the TGF-β antagonist inhibits TGF-β induced, Smad3-driven transcription, for instance, as measured using an in vitro reporter expression assay, such as an in vitro luciferase expression assay described herein. In some embodiments, the TGF-β antagonist inhibits TGF-β induced, Smad3-driven expression of the reporter gene (e.g., luciferase) by from about 10% to about 75%, or more, e.g., relative to an untreated sample, such as from about 15% to about 70%, 20% to about 65%, 25% to about 60%, 30% to about 55%, or 35% to about 50%, for instance, as assessed by measuring the decrease in activity of a protein encoded by the reporter gene (e.g., luciferase activity in a luciferase reporter assay as known in the art or described herein). In some embodiments, the TGF-β antagonist inhibits TGF-β-induced expression of fibronectin, α-smooth muscle actin (α-SMA), Snail, and/or Slug, for example, as measured using a cell-based immunoblot assay (e.g., as measured in squamous cell carcinoma A431 cells, for instance, as described herein). In some embodiments, the TGF-β antagonist inhibits TGF-β-induced expression of fibronectin, α-SMA. Snail, and/or Slug by about 25% to about 75%, or more, e.g., relative to an untreated sample, such as about 25%, 30%, 35%, 40%, 45%, 50%, 55%, 60%, 65%, 70%, 75%, or more, for instance, as measured by densitometry analysis of a developed immunoblot as known in the art or described herein. In some embodiments, the TGF-β antagonist is present in the assay at a concentration of from about 1 nM to about 50 nM (e.g., at a concentration of from about 10 nM to about 25 nM, such as about 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, or 25 nM).

In some embodiments, the TGF-β antagonist inhibits TGF-β-induced cancer cell invasion and metastasis (e.g., TGF-β-induced invasion of carcinoma cells, such as human squamous cell carcinoma cells), for instance, as assessed by a cancer cell invasion assay described herein. In some embodiments, the TGF-β antagonist inhibits TGF-β-induced cancer cell proliferation, for instance, as assessed by analysis of tumorigenicity and stem cell marker expression using techniques known in the art or described herein. In some embodiments, the TGF-β antagonist inhibits TGF-β-induced cancer cell migration (e.g., squamous cell carcinoma A431 cell migration, for instance, as measured using an in vitro wound closure assay). In some embodiments, the TGF-β antagonist inhibits TGF-β-induced cancer cell migration (e.g., squamous cell carcinoma A431 cell migration) such that from about 20% to about 40%, or less, of a wound inflicted upon the cultured cancer cells has closed, for instance, after about 24 hours of co-incubation of the cancer cells in the presence of TGF-β and the TGF-β antagonist. For instance, in some embodiments, the TGF-β antagonist inhibits TGF-β-induced cancer cell migration (e.g., squamous cell carcinoma A431 cell migration) such that about 40%, 45%, 40%, 35%, 30%, 25%, 20%, 15%, 10%, 5%, 4%, 3%, 2%, 1%, or less, of a wound inflicted upon the cultured cancer cells has closed, for instance, after about 24 hours of co-incubation of the cancer cells in the presence of TGF-β and the TGF-β antagonist. In some embodiments, the TGF-β antagonist is present in the in vitro wound closure assay at a concentration of from about 5 nM to about 10 nM, such as about 5 nM, 6 nM, 7 nM, 8 nM, 9 nM, or 10 nM.

In some embodiments, the TGF-β antagonist inhibits TGF-β induced fibrosis, for instance, as measured by assessing expression of fibronectin, plasminogen activator inhibitor-1 (PAI-1), and/or connective tissue growth factor (CTGF) in a cell-based immunoblot assay. In some embodiments, the TGF-β antagonist inhibits the expression (e.g., the TGF-β-induced expression) of one or more proteins involved in the epithelial-mesenchymal transition (EMT), such as E-cadherin, Twist, Snail, Slug, and α-smooth muscle actin (SMA). In some embodiments, the TGF-β antagonist inhibits TGF-β-induced fibrosis and/or EMT such that expression of fibronectin, PAI-1, and/or GTGF is reduced by from about 15% to about 50%, or more, e.g., relative to an untreated sample, such as by about 15%, 20%, 25%, 30%, 35%, 40%, 45%, 50%, or more, e.g., relative to an untreated sample, for example, as measured by densitometry analysis of a developed immunoblot as known in the art or described herein. In some embodiments, the expression of fibronectin, PAI-1, and/or CTGF is measured in human primary fibroblasts, such as wild type human primary fibroblasts or human primary fibroblasts derived from a subject suffering from scleroderma. In some embodiments, the TGF-β antagonist is present in the cell-based immunoblot assay at a concentration of from about 1 nM to about 25 nM, such as about 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, or 25 nM. In some embodiments, the TGF-β antagonist is present in the cell-based immunoblot assay at a concentration of from about 5 nM to about 10 nM, such as about 5 nM, 6 nM, 7 nM, 8 nM, 9 nM, or 10 nM.

In some embodiments, the TGF-β antagonist decreases bleomycin-induced induced expression of collagen 1, fibronectin, α-SMA. CTGF, or TGF-β, for instance, in a mouse treated with bleomycin in an amount sufficient to stimulate fibrosis. In some embodiments, the TGF-β antagonist inhibits dermal collagen content, for instance, as assessed using a trichrome staining assay known in the art or described herein. For example, in some embodiments, the TGF-β antagonist inhibits dermal collagen content such that the ratio of trichrome stain to total skin area is reduced, for instance, by from about 15% to about 50%, or more, e.g., relative to an untreated sample, (for example, by about 15%, 20%, 25%, 30%, 35%, 40%, 45%, 50%, or more) upon treatment with the TGF-β antagonist. In some embodiments, the TGF-β antagonist decreases bleomycin-induced phosphorylation of Smad2, for instance, in a mouse treated with bleomycin in an amount sufficient to stimulate fibrosis. In some embodiments, the mouse is treated with bleomycin to induce fibrosis and is subsequently treated with the TGF-β antagonist by subcutaneous injection, e.g., every other day for 28 days for a total of 14 injections.

In another aspect, the invention provides a pharmaceutical composition containing the TGF-β antagonist of any of the above-described aspects or embodiments and a pharmaceutically acceptable carrier.

In some embodiments, the TGF-β antagonist is formulated for oral administration, intravenous administration, intraocular administration, subcutaneous administration, intratumoral administration, transdermal administration, sublingual administration, transmucosal administration, or administration by inhalation. In some embodiments, the TGF-β antagonist is formulated as a patch, for instance, for transdermal administration. In some embodiments, the TGF-β antagonist is formulated with a surgical glue or co-formulated within a surgical suture or surgical staple.

In another aspect, the invention features the TGF-β antagonist or pharmaceutical composition of any of the above aspects or embodiments for use as a medicament, for instance, in the treatment, prevention, or alleviation of a symptom of a condition associated with a pathological increase in TGF-β activity. In another aspect, the invention features a method of treating a condition associated with a pathological increase in TGF-β activity in a subject in need thereof by administering to the subject a therapeutically effective amount of the TGF-β antagonist or pharmaceutical composition of any of the above aspects or embodiments. In another aspect, the invention features a method of preventing a condition associated with a pathological increase in TGF-β activity in a subject by administering to the subject a therapeutically effective amount of the TGF-β antagonist or pharmaceutical composition of any of the above aspects or embodiments. In another aspect, the invention features a method of alleviating a symptom of a condition associated with a pathological increase in TGF-β activity in a subject in need thereof by administering to the subject a therapeutically effective amount of the TGF-β antagonist or pharmaceutical composition of any of the above aspects or embodiments.

In some embodiments, the subject is a mammal, such as a human.

In some embodiments, the condition associated with a pathological increase in TGF-β activity is fibrosis, such as skin fibrosis, liver fibrosis, pulmonary fibrosis, or cardiac fibrosis. In some embodiments, the condition associated with a pathological increase in TGF-β activity is non-alcoholic steatohepatitis.

In some embodiments, the condition associated with a pathological increase in TGF-β activity is a pathological skin fibrotic condition, such as a wound or delayed wound healing. In some embodiments, the method includes contacting the wound with a topical formulation containing a therapeutically effective amount of the TGF-β antagonist for a time sufficient to promote healing of the wound. In some embodiments, the method includes surgically administering a skin graft to the subject at the site of the wound. The skin graft can contain one or more cells (e.g., fibroblasts, keratinocytes, Merkel cells, melanocytes, or Langerhans cells) that have been genetically modified so as to express the TGF-β-binding peptide. The skin graft may be, for instance, an autologous, allogeneic, syngeneic, or prosthetic skin graft. In some embodiments, the skin graft is a split-thickness skin graft or a full-thickness skin graft. In some embodiments, the method includes introducing a polynucleotide encoding the TGF-β-binding peptide into the one or more cells. For instance, the polynucleotide can be introduced into the one or more cells by contacting the one or more cells with a viral vector, such as a retrovirus, adenovirus, adenoassociated virus, parvovirus, coronavirus, rhabdovirus, paramyxovirus, picornavirus, alphavirus, herpes virus, or poxvirus, containing a nucleic acid encoding the TGF-β-binding peptide. In some embodiments, the polynucleotide is introduced into the one or more cells by contacting the one or more cells with a transposable element containing a nucleic acid encoding the TGF-β-binding peptide, such as a piggybac transposon or a sleeping beauty transposon. In some embodiments, the polynucleotide is introduced into the one or more cells by electroporation, Nucleofection™, or squeeze-poration. In some embodiments, the polynucleotide is introduced into the one or more cells by contacting the one or more cells with a transformation agent selected from the group consisting of a cationic polymer, a cationic lipid, calcium phosphate, an activated dendrimer, and a magnetic bead. In some embodiments, the method includes surgically administering a skin graft to the subject at the site of the wound, wherein the skin graft is contacted with a solution comprising the TGF-β antagonist at a concentration and for a time sufficient to permit absorption of a therapeutically effective amount of the TGF-β antagonist into the skin graft prior to surgically administering the skin graft to the subject.

In some embodiments, the pathological skin fibrotic condition is scarring, such as hypertrophic scarring or keloid scarring. In some embodiments, the scarring is present on an internal tissue or organ.

In some embodiments, the method includes contacting a wound or a scar on the subject with a topical formulation containing a therapeutically effective amount of the TGF-β antagonist for a time sufficient to reduce or prevent the formation of scar tissue. In some embodiments, the topical formulation is a patch or a cream.

In some embodiments, the condition associated with a pathological increase in TGF-β activity is an external wound, such as a wound caused by a surgical procedure. In some embodiments, the condition associated with a pathological increase in TGF-β activity is an internal wound present in an internal organ or tissue, such as an internal wound caused by a surgical procedure. In some embodiments, the method includes contacting the wound with a surgical glue, surgical staple, or surgical suture containing a therapeutically effective amount of the TGF-β antagonist for a time sufficient to reduce or prevent the formation of scar tissue.

In some embodiments, the condition associated with a pathological increase in TGF-β activity is a burn, such as an epidermal burn, superficial dermal burn, mid-dermal burn, deep dermal burn, or full thickness burn. In some embodiments, the method includes contacting the burn with a topical formulation containing a therapeutically effective amount of the TGF-β antagonist for a time sufficient to reduce or prevent the formation of scar tissue. In some embodiments, the topical formulation is a patch or a cream.

In some embodiments, the method includes surgically administering a skin graft to the subject at the site of the burn. The skin graft can contain one or more cells (e.g., fibroblasts, keratinocytes, Merkel cells, melanocytes, or Langerhans cells) that have been genetically modified so as to express the TGF-β-binding peptide. The skin graft may be, for instance, an autologous, allogeneic, syngeneic, or prosthetic skin graft. In some embodiments, the skin graft is a split-thickness skin graft or a full-thickness skin graft. In some embodiments, the method includes introducing a polynucleotide encoding the TGF-β-binding peptide into the one or more cells. For instance, the polynucleotide can be introduced into the one or more cells by contacting the one or more cells with a viral vector, such as a retrovirus, adenovirus, adenoassociated virus, parvovirus, coronavirus, rhabdovirus, paramyxovirus, picornavirus, alphavirus, herpes virus, or poxvirus, containing a nucleic acid encoding the TGF-β-binding peptide. In some embodiments, the polynucleotide is introduced into the one or more cells by contacting the one or more cells with a transposable element containing a nucleic acid encoding the TGF-β-binding peptide, such as a piggybac transposon or a sleeping beauty transposon. In some embodiments, the polynucleotide is introduced into the one or more cells by electroporation, Nucleofection™, or squeeze-poration. In some embodiments, the polynucleotide is introduced into the one or more cells by contacting the one or more cells with a transformation agent selected from the group consisting of a cationic polymer, a cationic lipid, calcium phosphate, an activated dendrimer, and a magnetic bead. In some embodiments, the method includes surgically administering a skin graft to the subject at the site of the wound, wherein the skin graft is contacted with a solution comprising the TGF-β antagonist at a concentration and for a time sufficient to permit absorption of a therapeutically effective amount of the TGF-β antagonist into the skin graft prior to surgically administering the skin graft to the subject.

In some embodiments, the pathological skin fibrotic condition is an autoimmune condition. In some embodiments, the autoimmune condition is psoriasis. In some embodiments, the autoimmune condition is scleroderma. In some embodiments, the method includes contacting the skin of the subject with a topical formulation containing a therapeutically effective amount of the TGF-β antagonist for a time sufficient to treat the condition. In some embodiments, the topical formulation is a patch or a cream.

In some embodiments, the condition associated with a pathological increase in TGF-β activity is cancer. In some embodiments, the cancer is a carcinoma, sarcoma, pancreatic cancer, glioblastoma, myeloid leukemia (e.g., drug resistant myeloid leukemia), head and neck cancer, melanoma, breast cancer, or colorectal cancer. In some embodiments, the carcinoma is selected from the group consisting squamous cell carcinoma, epidermoid carcinoma, urothelial carcinoma, adenocarcinoma, adrenocortical carcinoma, basal cell carcinoma, ductal carcinoma in situ (DCIS), invasive ductal carcinoma, merkel cell carcinoma, midline tract carcinoma, thymic carcinoma, and renal cell carcinoma.

In some embodiments, the carcinoma is squamous cell carcinoma. In some embodiments, the squamous cell carcinoma is vulvar squamous cell carcinoma, epidermal squamous cell carcinoma, oral squamous cell carcinoma, pulmonary squamous cell carcinoma, or head and neck squamous cell carcinoma.

In some embodiments, the method includes administering the TGF-β antagonist to the subject orally, intravenously, intratumorally, transdermally, subcutaneously, or topically to the subject. In some embodiments, the method includes contacting cancerous tissue (e.g., cancerous skin tissue) of the subject with a topical formulation containing a therapeutically effective amount of the TGF-β antagonist for a time sufficient to treat the cancer. In some embodiments, the topical formulation is a patch or a cream.

In some embodiments, the condition associated with a pathological increase in TGF-β activity condition is a pulmonary disease, such as asthma, chronic obstructive pulmonary disease, or fibroproliferative lung disease.

In some embodiments, the condition associated with a pathological increase in TGF-β activity is a renal disease, such as a renal disease associated with tubular atrophy, glomerulosclerosis, or tubulointerstitial fibrosis. In some embodiments, the renal disease is diabetic nephropathy. In some embodiments, the method includes administering the TGF-β antagonist to the subject by inhalation, for instance, as an aerosolized formulation. In some embodiments, the method includes administering the TGF-β antagonist orally or intravenously to the subject.

In another aspect, the invention features a method of synthesizing the TGF-β antagonist of any of the above aspects or embodiments by preparing the TGF-β-binding peptide by solid-phase peptide synthesis. In another aspect, the invention features a method of producing the TGF-β antagonist of any of the above aspects or embodiments by expressing the TGF-β-binding peptide in a cell and purifying the TGF-β-binding peptide from a mixture comprising the cell. In some embodiments, the cell is a prokaryotic cell, such as an *E. coli* cell. In some embodiments, the cell is a eukaryotic cell, such as a mammalian cell (e.g., a human cell). In some embodiments, the method includes purifying the TGF-β-binding peptide by a chromatographic technique. For instance, the TGF-β-binding peptide may be purified by high-performance liquid chromatography (HPLC), affinity chromatography, ion-exchange chromatography, or size-exclusion chromatography. The TGF-β-binding peptide can be purified, for instance, to 85%, 90%, 95%, 97%, 98%, 99%, 99.8%, or 99.9% purity, or greater.

In another aspect, the invention provides a kit containing the TGF-β antagonist or the pharmaceutical composition of any of the above aspects or embodiments, as well as a package insert that instructs a user of the kit to perform a method of the invention. For instance, in some embodiments, the kit contains the TGF-β antagonist or the pharmaceutical composition of any of the above aspects or embodiments, as well as a package insert that instructs a user of the kit to administer a therapeutically effective amount of the TGF-β antagonist or the pharmaceutical composition to a subject to treat a condition associated with a pathological increase in TGF-β activity, such as a condition described herein. In some embodiments, the kit contains the TGF-β antagonist or the pharmaceutical composition of any of the above aspects or embodiments, as well as a package insert that instructs a user of the kit to administer a therapeutically effective amount of the TGF-β antagonist or the pharmaceutical composition to a subject to prevent a condition associated with a pathological increase in TGF-β activity, such as a condition described herein. In some embodiments, the kit contains the TGF-β antagonist or the pharmaceutical composition of any of the above aspects or embodiments, as well as a package insert that instructs a user of the kit to administer a therapeutically effective amount of the TGF-β antagonist or the pharmaceutical composition to a subject to alleviate a symptom of a condition associated with a pathological increase in TGF-β activity, such as a condition described herein.

Definitions

As used herein, the term "about" refers to a value that is within 10% above or below the value being described. For instance, the phrase "about 50 nM" refers to a value between and including 45 nM and 55 nM.

As used herein, the term "affinity" refers to the strength of a binding interaction between two molecules, such as a ligand and a receptor. The term "$K_d$", as used herein, is intended to refer to the dissociation constant, which can be obtained, for example, from the ratio of the rate constant for the dissociation of the two molecules ($k_d$) to the rate constant for the association of the two molecules ($k_a$) and is expressed as a molar concentration (M). $K_d$ values for peptide-protein interactions can be determined, e.g., using methods established in the art. Methods that can be used to determine the $K_d$ of a peptide-protein interaction include surface plasmon resonance, e.g., through the use of a biosensor system such as a BIACORE® system, as well as fluorescence anisotropy and polarization methods and calorimetry techniques known in the art, such as isothermal titration calorimetry (ITC). As used herein, the term "burn" refers to a form of skin trauma caused by exposure to intense heat or cold. A burn may be classified based on the depth with which the burn extends to the epidermal and underlying dermal tissue. Epidermal burns are also referred to as first-degree burns, and are characterized by injury to the epidermis without trauma to the underlying dermal tissue. Common causes of this type of burn include sun and minor flash injuries from small explosions. The stratified layers of the epidermis are burnt away and healing occurs by regeneration of the epidermis from the basal layer. These burns are hyperemic and therefore are red in color and maybe quite painful. Small blister development and skin desquamation are delayed, sometimes for some days (e.g., from about 1 to about 7 days). Superficial dermal burns are characterized by trauma that extends just beyond the epidermis, and may terminate at the junction of sensory receptors with the epidermal tissue. These burns involve the epidermis and the superficial part of the dermis, referred to as the papillary dermis. These types of burns are very painful due to the exposure of sensory nerves. Capillary return will often be brisk as vasculature is intact. Blisters are common characteristics of superficial dermal burns. The skin covering the blister is dead and is separated from the base by inflammatory edema fluid. This fluid tents up the necrotic roof, thus forming the blister. When the blister ruptures the underlying papillary dermis is exposed. Desiccation of the exposed dermis may affect the depth of tissue loss. Mid dermal burns have a zone of damaged, non-viable tissue extending into the dermis, with damaged but viable dermal tissue at the base. As some of the nerve endings remain viable, pain is often experienced, though it tends to be less severe than the pain of superficial burns. Similarly, as some of the capillaries remain viable, capillary return is present, albeit delayed. Deep dermal burns are characterized by the early (e.g., within hours) development of extensive blisters, which usually rupture early to expose deep damage within the dermis. The exposed reticular dermis may be pale in color due to damage to dermal blood vessels, or red due to extravasation of red blood cells from damaged vessels. A characteristic of these types of burns is greatly diminished capillary return, with no or sluggish blanching when pressure is applied to the wound bed. This is a result of the extensive destruction of the dermal vascular plexus. The dermal nerve endings are also damaged and so sensation is reduced. These deeper burns tend to be dry, with diminished fluid exudates compared with more superficial burns. Full thickness burns destroy both the epidermis and dermis, and may penetrate more deeply into underlying structures. These burns have a dense white, waxy, or even charred appearance. The sensory nerves in the dermis are destroyed in a full thickness burn.

As used herein, the term "derived from" in the context of a cell derived from a subject refers to a cell, such as a fibroblast derived from a human patient (e.g., a human scleroderma patient), that is either isolated directly from the subject or obtained from expansion, division, maturation, or manipulation (e.g., ex vivo expansion, division, maturation, or manipulation) of one or more cells isolated directly from the subject. For instance, a cell (such as a fibroblast) is derived from a subject (e.g., a human subject, such as a human subject suffering from scleroderma or a disease or condition associated with elevated TGF-β activity described herein) if the cell is isolated from the subject or obtained from the ex vivo culture and/or expansion, division, maturation, or manipulation of one or more cells isolated directly from the subject.

As used herein, the term "dimer" refers to a multimeric form of a compound, such as a peptide. For instance, in the context of a TGF-β antagonist described herein, a peptidic TGF-β antagonist or a variant thereof can be dimerized, e.g., such that two peptidic TGF-β antagonist (or their variants) are covalently bound to one another. Dimeric TGF-β antagonists may contain two copies of a TGF-β-binding peptide (e.g., a peptide containing the amino acid sequence of any one of SEQ ID NOs: 5, 6, 12-15, and 22-25) bound to one another by a direct disulfide bridge between cysteine residues within the peptides or by way of a linker, such as by way of thioether or amide bonds between a cysteine or lysine residue within each copy of the peptide an a bivalent linking moiety. Exemplary linking moieties include, for instance, succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, for instance, Liu et al., 18:690-697, 1979, the disclosure of which is incorporated herein by reference as it pertains to linkers for chemical conjugation. Additional linkers include the non-cleavable maleimidocaproyl linkers, which are particularly useful for the conjugation of microtubule-disrupting agents such as auristatins, are described by Doronina et al., Bioconjugate Chem. 17:14-24, 2006, the disclosure of which is incorporated herein by reference as it pertains to linkers for chemical conjugation.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted therefrom.

As used herein, the term "fibrosis" refers to any pathological condition resulting from an accumulation of excess fibrous tissue through either overproduction or insufficient degradation of extracellular matrix. The term "fibrotic disease" or "fibrotic condition" as used herein refers to any disease, condition, or disorder that is associated with fibrosis. The disease, condition, or disorder may be characterised by, caused by, or otherwise associated with fibrosis, either directly or indirectly. Exemplary fibrotic conditions include scarring, such as scarring of the skin (e.g., hypertrophic scarring and keloid scarring, among others) and internal tissues or organs.

As used herein, the term "low-molecular weight" in the context of a peptide refers to a peptide that has a molecular weight of less than 10 kDa, such as a peptide that has a molecular weight of 9,000 Da, 8,000 Da, 7,000 Da, 6,000 Da, 5,000 Da, 4,000 Da, 3,000 Da, or less.

As used herein, the term "pharmaceutical composition" refers to a mixture containing a therapeutic compound, such as a TGF-β antagonist described herein, to be administered to a subject, such as a mammal, e.g., a human, in order to prevent, treat or control a particular disease or condition (such as a disease or condition associated with elevated TGF-β activity described herein) affecting or that may affect the mammal.

As used herein, the term "pharmaceutically acceptable" refers to the suitability of a carrier or vehicle for use in mammals, including humans, without undue toxicity, incompatibility, instability, irritation, allergic response, and the like, commensurate with a reasonable benefit/risk ratio.

As used herein, the term "pharmaceutically acceptable carrier or vehicle" refers to a diluent, adjuvant, excipient, or carrier with which the peptidic TGF-β antagonists described herein and/or their variants can be co-formulated for administration.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject (e.g., a human subject, such as a human subject suffering from a disease or condition associated with elevated TGF-β activity as described herein).

As used herein, the terms "scar tissue" and "scar tissue formation" refer to any pathological condition resulting from fibrosis, including keloidosis, fibrocystic conditions, and joint stiffness. The terms also include post-surgical adhesions or contractures, keloids, hyperplastic, or hypertrophic masses formed following trauma, depressed scars from inflammatory responses including acne, wrinkling, cellulite formation, neoplastic fibrosis, and other fibrotic conditions involving fibroblast proliferation and metabolism at a localized area in the body. Such localized areas may also be referred to herein as a "site" or "biological tissue."

As used herein, the term "skin graft" refers to skin tissue that is transplanted to a subject, such as a human subject suffering from a burn, wound (e.g., a wound due to injury or a surgical procedure, such as a surgical procedure in which cancerous tissue (e.g., skin cancer, such as a skin cancer described herein) is removed. Exemplary skin grafts for use with the compositions and methods described herein include autologous skin grafts, in which skin from another area of the subject's body is removed and transplanted to the affected site, as well as syngeneic skin grafts obtained from a genetically identical or major histocompatability complex (MHC)-matched donor of the same species and allogeneic skin grafts obtained from a genetically distinct donor of the same species. Skin grafts may be prosthetic, such as skin grafts produced from artificial materials, for instance, as described in U.S. Pat. No. 5,196,190, the disclosure of which is incorporated herein by reference. Skin grafts may be split-thickness skin grafts, which include epidermal tissue and a portion of the dermal tissue, depending on the severity of the trauma being treated. Skin grafts may be full-thickness skin grafts, which include epidermal tissue and the entirety of the dermis. Composite grafts may also be used with the compositions and methods described herein, as these skin grafts include the epidermis, dermis, and underlying cartilage tissue.

As used herein, the phrases "specifically binds" and "binds" refer to a binding reaction which is determinative of the presence of a particular protein in a heterogeneous population of proteins and other biological molecules that is recognized, e.g., by a ligand with particularity. A ligand (e.g., a protein, peptide, or small molecule) that specifically binds to a protein will bind to the protein, e.g., with a $K_D$ of less than 100 µM. For example, a peptide (e.g., a TGF-β-binding peptide) that specifically binds to a protein (e.g., TGF-β) may bind to the protein with a $K_{ID}$ of up to 1 µM (e.g., between 1 pM and 1 µM). A variety of assay formats may be used to determine the affinity of a ligand (e.g., a peptide, such as a TGF-β-binding peptide) for a specific protein (e.g., TGF-β). For example, solid-phase ELISA assays are routinely used to identify ligands that specifically bind a particular protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject" and "patient" are interchangeable and refer to an organism that receives treatment for a particular disease or condition as described herein. Examples of subjects and patients include mammals, such as humans, receiving treatment for diseases or conditions, such as conditions associated with elevated TGF-β activity.

As used herein, the term "TGF-β antagonist" refers to a compound (e.g., a protein, such as a fusion protein, or a low-molecular weight peptide) capable of inhibiting TGF-β signaling. A TGF-β antagonist may contain a peptide and, optionally, one or more non-peptidic molecules. A TGF-β antagonist may contain, consist of, or consist essentially of a "TGF-β-binding peptide," which refers to a peptide (e.g., a peptide containing the amino acid sequence of any one of SEQ ID NOs: 5, 6, 12-15, and 22-25, capable of binding TGF-β. Binding of a peptide to TGF-β can be assessed, for instance, using a protein binding assay known in the art, such as ELISA, fluorescence anisotropy or fluorescence polarization, and calorimetry, such as isothermal titration calorimetry (ITC). Binding of a peptide to TGF-β can also be assessed by observing a decrease in TGF-β signaling, for instance, due to binding of TGF-β to a TGF-β-binding peptide that is competitive with binding of TGF-β to a TGF-β receptor. Binding of a peptide, for instance, a peptide having the amino acid sequence of any one of SEQ ID NOs: 5, 6, 12-15, and 22-25, to TGF-β can be determined, for example, by observing peptide-mediated inhibition of TGF-β induced, Smad3-driven transcription. This can be measured, for example, using an in vitro reporter expression assay, such as an in vitro luciferase expression assay described herein. Binding of a peptide to TGF-β can be determined by measuring, for example, peptide-mediated inhibition of TGF-β induced, Smad3-driven expression of the reporter gene (e.g., luciferase) by from about 10% to about 75%, or more, such as from about 15% to about 70%, 20% to about 65%, 25% to about 60%, 30% to about 55%, or 35% to about 50%, e.g., relative to an untreated sample, for instance, as assessed by measuring the decrease in activity of a protein encoded by the reporter gene (e.g., luciferase activity in a luciferase reporter assay as known in the art or described herein). Binding of a peptide, such as a peptide having the amino acid sequence of any one of SEQ ID NOs: 5, 6, 12-15, and 22-25, to TGF-β can be determined, for example, by observing peptide-mediated inhibition of inhibits TGF-β-induced expression of a protein that is normally expressed as a result of TGF-β signal transduction, such as fibronectin, α-smooth muscle actin (α-SMA), Snail, and/or Slug. This can be measured, for example, using a cell-based immunoblot assay (e.g., as measured in squamous cell carcinoma A431 cells, for instance, as described herein). Binding of a peptide to TGF-13 can be determined by measuring, for example, peptide-mediated inhibition of TGF-β-induced expression of fibronectin, α-SMA. Snail, and/or Slug by about 25% to about 75%, or more, e.g., relative to an untreated sample, such as about 25%, 30%, 35%, 40%, 45%, 50%, 55%, 60%, 65%, 70%, 75%, or more, for instance, as measured by densitometry analysis of a developed immunoblot as known in the art or described herein. Binding of a peptide, for instance, a peptide having the amino acid sequence of any one of SEQ ID NOs: 5, 6, 12-15, and 22-25, to TGF-β can also be determined, for example, by observing peptide-mediated inhibition of TGF-β-induced cancer cell invasion and metastasis (e.g., TGF-β-induced invasion of carcinoma cells, such as human squamous cell carcinoma cells), for instance, as assessed by a cancer cell invasion assay described herein. For instance, binding of a peptide to TGF-β can be measured by observing peptide-mediated reduction in cancer cell proliferation, for instance, as assessed by analysis of tumorigenicity and stem cell marker expression using techniques known in the art or described herein, and/or cancer cell migration (e.g., squamous cell carcinoma A431 cell migration, for instance, as measured using an in vitro wound closure assay). Binding of a peptide to TGF-β can be determined by measuring, for example, peptide-mediated attenuation of cancer cell migration (e.g., squamous cell carcinoma A431 cell migration) such that from about 20% to about 40%, or less, of a wound inflicted upon the cultured cancer cells has closed, for instance, after about 24 hours of co-incubation of the cancer cells in the presence of TGF-β and the TGF-β antagonist. For instance, binding of a peptide, such as a peptide having the amino acid sequence of any one of SEQ ID NOs: 5, 6, 12-15, and 22-25, to a TGF-β can be observed by detecting a reduction in TGF-β-induced cancer cell migration (e.g., squamous cell carcinoma A431 cell migration) such that about 40%, 45%, 40%, 35%, 30%, 25%, 20%, 15%, 10%, 5%, 4%, 3%, 2%, 1%, or less, of a wound inflicted upon the cultured cancer cells has closed, for instance, after about 24 hours of co-incubation of the cancer cells in the presence of TGF-β and the TGF-β antagonist. Binding of a peptide, such as a peptide having the amino acid sequence of any one of SEQ ID NOs: 5, 6, 12-15, and 22-25, to a TGF-β can also be observed, for instance, by detecting a peptide-mediated decrease in the expression of fibronectin, plasminogen activator inhibitor-1 (PAI-1), and/or connective tissue growth factor (CTGF) in a cell-based immunoblot assay. For example, binding of a peptide, such as a peptide having the amino acid sequence of any one of SEQ ID NOs: 5, 6, 12-15, and 22-25, to TGF-β can be observed by detecting peptide-mediated inhibition of the expression (e.g., the TGF-β-induced expression) of one or more proteins involved in the epithelial-mesenchymal transition (EMT), such as E-cadherin, Twist, Snail, Slug, and α-smooth muscle actin (SMA). For instance, binding of a peptide, such as a peptide having the amino acid sequence of any one of SEQ ID NOs: 5, 6, 12-15, and 22-25, to a TGF-β can be observed by detecting peptide-mediated inhibition of TGF-β-induced fibrosis and/or EMT such that expression of fibronectin, PAI-1, and/or GTGF is reduced by from about 15% to about 50%, or more, e.g., relative to an untreated sample, such as by about 15%, 20%, 25%, 30%, 35%, 40%, 45%, 50%, or more, for example, as measured by densitometry analysis of a developed immunoblot as known in the art or described herein. As used herein, the terms "TGF-β-binding peptide" and "TGF-β antagonist peptide" are used interchangeably.

As used herein, the term "TGF-β signaling" refers to the endogenous signal transduction cascade by which TGF-β potentiates the intracellular activity of the TGF-β receptor so as to effect one or more biological responses. TGF-β signaling encompasses the TGF-β-mediated stimulation of a TGF-β receptor and concomitant phosphorylation and activation of receptor-associated Smad proteins. TGF-β signaling includes the translocation of one or more Smad transcription factors to the nucleus, for example, by way of an interaction between a Smad protein and nucleoporins. TGF-β signaling encompasses the release of one or more Smad protein from Smad Anchor for Receptor Activation (SARA), which sequesters Smad proteins in the cytoplasm and prevents their translocation into the nucleus.

As used herein, the term "therapeutically effective amount" of a therapeutic agent, such as a TGF-β antagonist described herein, refers to an amount that is sufficient, when administered to a subject suffering from or susceptible to a disease, disorder, and/or condition, (e.g., a disease, disorder, and/or condition associated with a pathological increase in TGF-β activity as described herein) to treat, prevent, and/or delay the onset of one or more symptom(s) of the disease, disorder, and/or condition.

As used herein, the terms "treat" or "treatment" in the context of a subject suffering from a disease or condition associated with a pathological increase in TGF-β activity refer to treatment, for instance, by administration of a TGF-β antagonist, with the intention of alleviating a phenotype associated with the disease or condition. For instance, exemplary forms of treatment include administration of a TGF-β antagonist, such as a TGF-β antagonist described herein, to a subject suffering from a cancer (e.g., a carcinoma, such as a squamous cell carcinoma described herein, or a sarcoma, such as a sarcoma described herein) or a fibrotic disease (e.g., a fibrotic condition of the skin, lungs, liver, heart, or other organ as described herein) so as to reduce the progression of the disease or attenuate the severity of one or more symptoms associated with the disease. For instance, treatment of a patient suffering from a cancer, such as a cancer described herein, may include administration of, for example, a TGF-β antagonist so as to reduce cancer cell metastasis, cancer cell number, and/or cancer cell migration, in the patient. Treatment of a patient suffering from a fibrotic condition, such as a fibrotic condition described herein, may include administration of, for example, a TGF-β antagonist so as to reduce or prevent the formation of scar tissue. Treatment can be assessed by detecting a decrease in the expression of one or more proteins involved in the epithelial-mesenchymal transition (EMT), such as E-cadherin, Twist, Snail, Slug, and α-smooth muscle actin (SMA) in a sample isolated from a subject following administration of a TGF-β antagonist. Treatment of a cancer patient can be assessed, for instance, by detecting a decrease in the proliferation, metastasis, migration, or cell count of a population of cancer cells isolated from a subject (for instance, in a tumor biopsy isolated from a subject) following administration of a TGF-β antagonist. Treatment of a fibrosis patient can be assessed, for instance, by detecting a reduction in the rate of formation of scar tissue, for example, by visual inspection of the subject following administration of a TGF-β antagonist.

As used herein, the term "variant" in the context of a TGF-β antagonist peptide refers to a TGF-β antagonist peptide that is cyclic, dimeric, or exhibits sequence identity (e.g., up to 85% sequence identity, such as 85%, 90%, 95%, 97%, or 99%, or greater) to the TGF-β antagonist peptide.

As used herein, the term "alkyl" refers to an optionally branched alkyl moiety having, for instance, from one or more carbon atoms, such as from 1 to 6 carbon atoms, such as methyl, ethyl, propyl, isopropyl, butyl, isobutyl, sec-butyl, tert-butyl, pentyl, isopentyl, neopentyl, tert-pentyl, hexyl, and the like.

As used herein, the term "aryl" refers to an unsaturated aromatic carbocyclic group of from 6 to 14 carbon atoms having a single ring (e.g., optionally substituted phenyl) or multiple condensed rings (e.g., optionally substituted naphthyl). Exemplary aryl groups include phenyl, naphthyl, phenanthrenyl, and the like. As used herein, the term "aryl" includes substituted aryl substituents, such as an aryl moiety containing a $C_1$-$C_6$ alkyl, $C_2$-$C_6$ alkenyl, $C_2$-$C_6$ alkynyl, cycloalkyl, heterocycloalkyl, $C_1$-$C_6$ alkyl aryl, $C_1$-$C_6$ alkyl heteroaryl, $C_1$-$C_6$ alkyl cycloalkyl, $C_1$-$C_6$-alkyl heterocycloalkyl, amino, ammonium, acyl, acyloxy, acylamino, aminocarbonyl, alkoxycarbonyl, ureido, carbamate, aryl, heteroaryl, sulfinyl, sulfonyl, alkoxy, sulfanyl, halogen, carboxy, trihalomethyl, cyano, hydroxy, mercapto, or nitro substituent, or the like.

As used herein, the term "cycloalkyl" refers to a monocyclic cycloalkyl group having, for instance, from 3 to 8 carbon atoms, such as cyclopropyl, cyclobutyl, cyclopentyl, cyclohexyl, cycloheptyl, cyclooctyl, and the like.

As used herein, the term "heteroaryl" refers to a monocyclic heteroaromatic, or a bicyclic or a tricyclic fused-ring heteroaromatic group. Exemplary heteroaryl groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, phthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heterocycloalkyl" refers to a 3 to 8-membered heterocycloalkyl group having one or more heteroatoms, such as a nitrogen atom, an oxygen atom, a sulfur atom, and the like, and optionally having one or more oxo groups. Exemplary heterocycloalkyl substituents include pyrrolidinyl, piperidinyl, oxopiperidinyl, morpholinyl, piperazinyl, 1-methylpiperazinyl, oxopiperazinyl, thiomorpholinyl, azepanyl, diazepanyl, oxazepanyl, thiazepanyl, dioxothiazepanyl, azokanyl, tetrahydrofuranyl, tetrahydropyranyl, and the like.

Unless otherwise constrained by the definition of the individual substituent, the foregoing chemical moieties, such as "alkyl", "alkenyl", "alkynyl", "aryl," and "heteroaryl" groups can optionally be substituted with, for example, from 1 to 5 substituents selected from the group consisting of $C_1$-$C_6$ alkyl, $C_2$-$C_6$ alkenyl, $C_2$-$C_6$ alkynyl, cycloalkyl, heterocycloalkyl, $C_1$-$C_6$ alkyl aryl, $C_1$-$C_6$ alkyl heteroaryl, $C_1$-$C_6$ alkyl cycloalkyl, $C_1$-$C_6$-alkyl heterocycloalkyl, amino, ammonium, acyl, acyloxy, acylamino, aminocarbonyl, alkoxycarbonyl, ureido, carbamate, aryl, heteroaryl, sulfinyl, sulfonyl, alkoxy, sulfanyl, halogen, carboxy, trihalomethyl, cyano, hydroxy, mercapto, nitro, and the like. The substitution may include situations in which neighboring substituents have undergone ring closure, such as ring closure of vicinal functional substituents, to form, for instance, lactams, lactones, cyclic anhydrides, acetals, hemiacetals, thioacetals, aminals, and hemiaminals, formed by ring closure, for example, to furnish a protecting group.

BRIEF DESCRIPTION OF THE FIGURES

FIGS. 2A and 2B illustrate the in silico analysis of peptide X aggregation propensity and the design of aggregation-free small molecular weight CD109-based peptides. (FIG. 2A) Aggrescan analysis of peptide X identified amino acids at position 13-18 (ETWIWL, SEQ ID NO: 11) as an aggregation-prone sequence in the 40 amino acid peptide. (FIG. 2B) Amino acid sequence of small molecular weight CD109-based peptides that were designed and tested.

(FIGS. 3A and 3B) The data is plotted with relative absorbance (Y-axis) against elution volume (X-axis). Peptides 1-9 are color coded (A peptides (1) to (5); B (peptides (6) to (9)). As shown on panel A, peptide X (peptide 1, black line) elution profile indicated two major peaks at approximately 8 mL and 11 mL which correspond to molecular weights greater than 12.4 kDa. The theoretical molecular weight of peptide X is 4.7 kDa which is expected to elute from the column at approximately 15 mL. Under the conditions tested, peptide X existed as high molecular weight aggregates with minimal soluble (monomeric) form. On the other hand, P16 (peptide 5, green line) elution profile indicated a broad peak between 14-22 mL which is expected to contain peptides of between 0.1 and 6 kDa and is consistent with its theoretical molecular weight of 2.01 kDa. A standard curve used to determine molecular weights of peptides analyzed by size exclusion chromatography is indicated in FIG. 4.

(FIG. 12A) CD109 mRNA expression is decreased in 5 out of 5 tumors (T) of vulvar squamous cell carcinoma as compared to the adjacent normal tissue (N). (FIG. 12B) Densitometry was performed using Image J™ software and data are expressed as relative expression. P=0.08.

(FIG. 13A) HaCaT stably transfected with CD109 or EV were treated with 100 pM TGF-β1 for 48 hrs, fixed and stained with Rhodamin-Phalloidin (stain for F-actin, $1^{st}$ line), E-cadherin ($2^{nd}$ line) and DAPI ($3^{rd}$ line). (FIG. 13B) HaCaT cells transfected with control or CD109 siRNA were treated with 100 pM TGF-β1 for 36 hrs and stained as in (A). (FIG. 13C) A431 stably transfected with CD109 or EV were treated and stained as in (A). (FIG. 13D) A431 transfected with CD109 siRNA or a control siRNA were treated with 50 pM TGF-β1 for 48 hrs and stained as in (A). (A-D) Left: representative panels of cells are shown. Right panel: Densitometry of actin staining (mean of 3 experiments±SEM; *: p<0.05). (FIG. 13E) HaCaT cells transfected with control or CD109 siRNA were treated with 100 pM TGF-β1 for 4 hrs. Cell lysates were subjected to western blot using the indicated antibodies. (FIG. 13F) A431 cells stably transfected with CD109 or EV were treated with or without 100 pM TGF-β1 for 3 hrs. Cell lysates were analyzed by western blot for Slug expression. The actin panel demonstrates equal protein loading. All western blots are representative of n=3 experiments.

(FIG. 14A) HaCaT cells stably transfected with CD109 or EV were scratched and treated with or without 100 pM TGF-β1 for 24 hrs. (FIG. 14B) HaCaT cells transfected with control or CD109 siRNA were scratched and treated as in (A). (FIG. 14C) A431 cells stably transfected with CD109 or EV were scratched and treated as in (A). (FIG. 14D) A431 cells transfected with CD109 siRNA or control siRNA were scratched and treated as in (A). Pictures of the wounded area were taken at 0 and 24 hrs and the percentage of the original wound area filled with keratinocytes were calculated. The graphs shows the mean of n≥13 independent experiments±SEM; *: p<0.05. Dotted line: wound margin at 0 hr, regular line: wound margin at 24 hr.

FIGS. 15A and 15B illustrate that CD109 inhibits TGF-β induced cell invasion. (FIG. 15A) 431 cells stably transfected with CD109 or EV were used. (FIG. 15B) A431 cells transfected with CD109 siRNA or control siRNA were used.

Cells were left untreated or treated with 100 pM of TGF-β and were plated in the Matrigel®-coated Boyden chambers. Percent-invaded cells in the lower chambers were determined as per the manufacturer's instructions. Each bar represents mean±standard error of the mean. All results are representative of three separate experiments and analyzed by t-test. **P<0.01.

FIGS. 16A and 16B illustrate that CD109 inhibits TGF-β-induced EMT via the SMAD2/3 and MAPK pathways. HaCaT cells transfected with control or CD109 siRNA were treated for 36 hrs with 100 pM TGF-β1, in the presence or absence of 0.5 μM SB431542, 1 μM SB203580 and/or 10 μM U0126. Cells were fixed and stained for F-actin, E-cadherin and with DAPI. (FIG. 16A) Representative panels of cells are shown. (FIG. 16B) Densitometry of F-actin staining (mean of n=3 independent experiments±SEM; *P<0.05).

Figure 17:
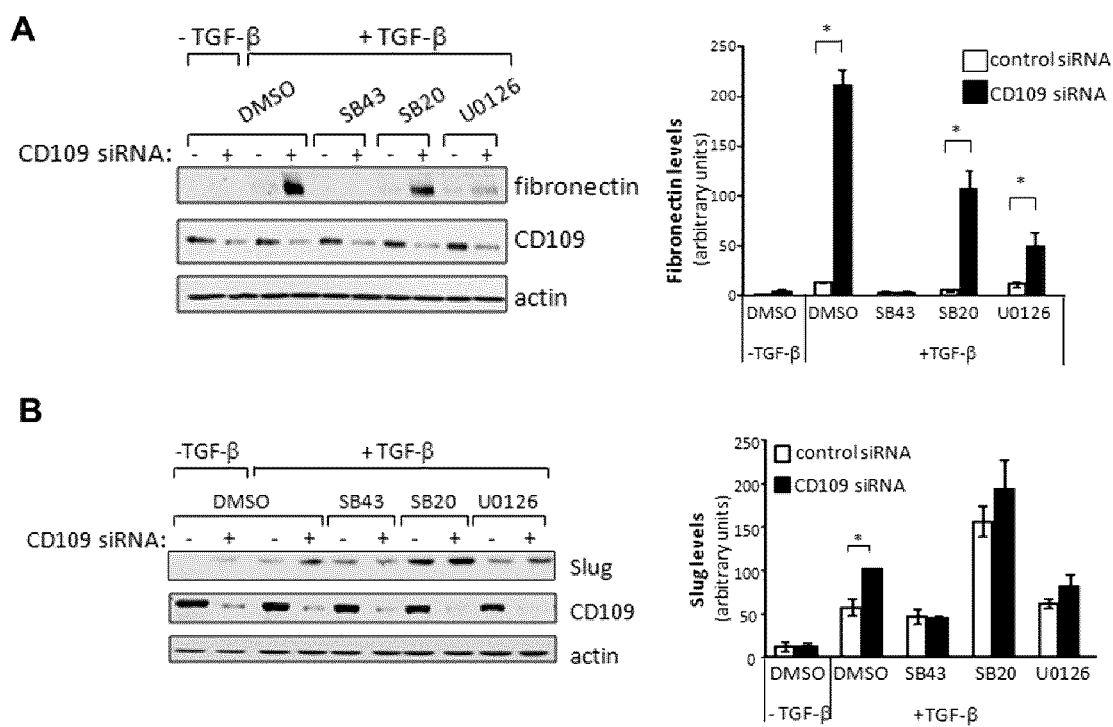

FIGS. 17A and 17B illustrate that CD109 inhibits TGF-β-induced fibronectin and Slug expression via the SMAD2/3 and MAPK pathways. (FIG. 17A) HaCaT cells transfected with control or CD109 siRNA were treated for 16 hrs with or without 100 pM TGF-β1, in the presence or absence of 0.5 μM SB431542, 1 μM SB203580 or 10 μM U0126. Cell lysates were analyzed by western blot using the indicated antibodies. Right panel: Densitometry of fibronectin (mean of n=3 independent experiments, ±SEM; *: p<0.05). (FIG. 17B) HaCaT cells transfected with control or CD109 siRNA were treated with 100 pM TGF-β1 for 4 hrs, in the presence of absence of 0.5 μM SB431542, 1 μM SB203580 or 10 μM U0126 and analyzed by western blot for Slug expression. Right panel: Densitometry of n=4 independent experiments, ±SEM; *: p<0.05.

Figure 18:
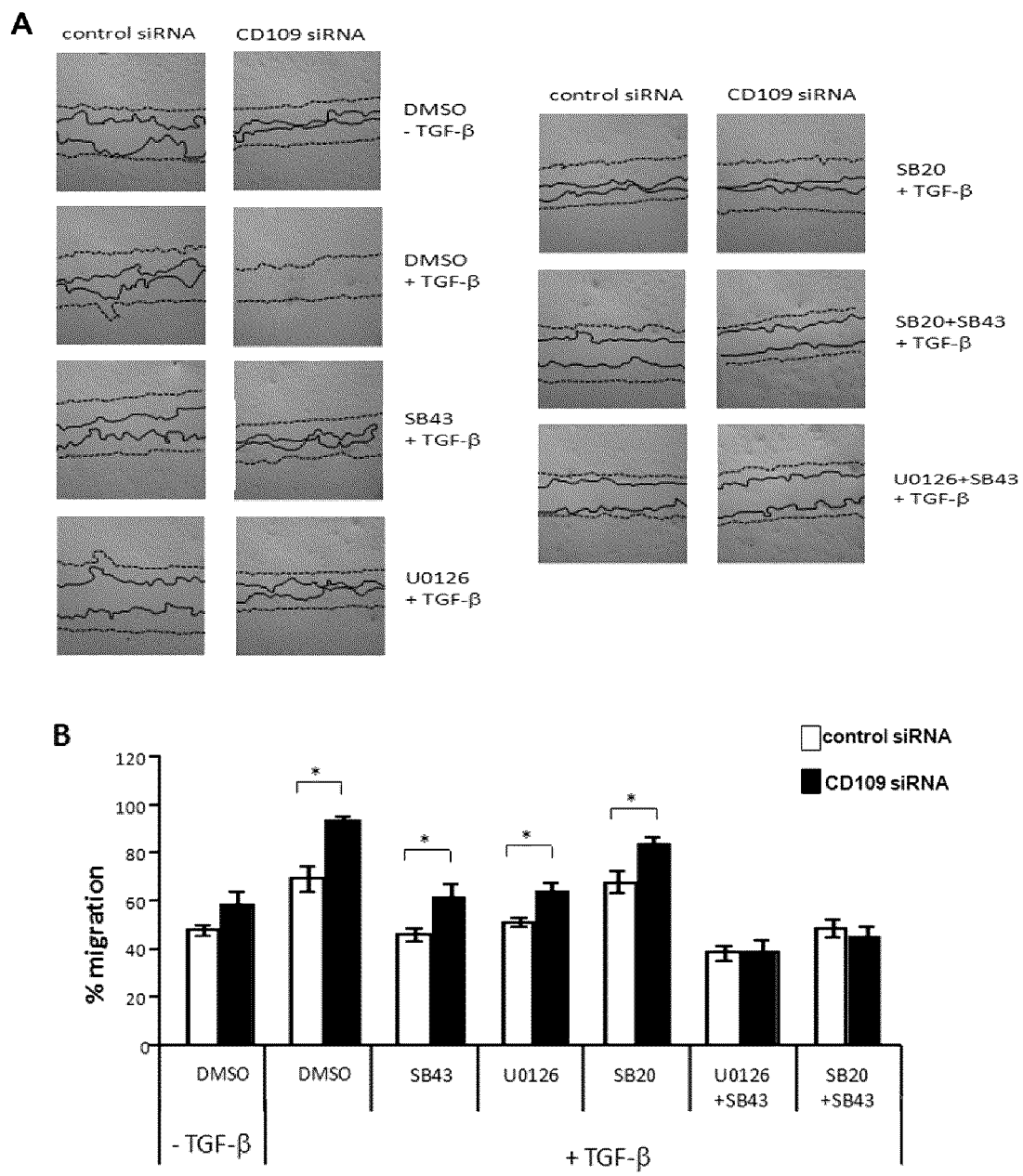

FIGS. 18A and B illustrate that CD109 regulates TGF-β-induced migration via the SMAD2/3 and MAPK pathways. (FIG. 18A) HaCaT cells transfected with control or CD109 siRNA were scratched and treated with or without 100 pM TGF-β1, 0.5 μM SB431542, 1 μM SB203580 and/or 10 μM U0126 for 36 hrs. Dotted line: wound margin at 0 hr, regular line: wound margin at 36 hrs. (FIG. 18B) The graph shows the percentage of migration (compared to wound at 0 hr), *: p<0.05, n=5 independent experiments.

FIGS. 19A-19F illustrate that CD109 modulates TGF-β-induced p38 and ERK1/2 phosphorylation. (FIG. 19A) HaCaT cells transfected with CD109 siRNA or control siRNA were treated with 15 pM TGF-β1 for the indicated time. (FIGS. 19B and 19C) HaCaT cells transfected with CD109 siRNA or control siRNA were treated with 0-60 pM TGF-β1 for 10 min. (FIGS. 19D and 19E) A431 cells transfected with control or CD109 siRNA were treated with 15 pM TGF-β1 for the indicated times (D) or with 0-50 pM TGF-β for 10 min (E). (FIG. 19F) HaCaT cells stably transfected with CD109 or its EV were transiently transfected with caveolin-1 siRNA or negative control siRNA. The cells were then treated with 15 pM TGF-β1 for 0-10 min. Cell lysates were then analyzed by western blot.

FIGS. 20A and 20B illustrate that CD109 inhibits TGF-β-induced EMT in SCC-13 cells. (FIG. 20A) SCC-13 transfected with CD109 siRNA or a control siRNA were treated and stained for F-actin ($1^{st}$ line), E-cadherin ($2^{nd}$ line) and DAPI ($3^{rd}$ line). Left: representative panels of cells are shown. Right: densitometry of actin-staining (mean of n=3 experiments±SEM; *: p<0.05). (FIG. 20B) SCC-13 cells transfected with CD109 siRNA or a control siRNA were treated with 100 pM TGF-β1 for 2 hrs. Cell lysates were analyzed by western blotting for Slug expression. The actin panel demonstrates equal protein loading.

FIGS. 21A and 21B illustrate that CD109 inhibits TGF-β-induced fibronectin expression in SCC-derived cells. (FIG. 21A) A431 cells stably transfected with CD109 or EV were treated with 0-100 pM TGF-β1 for 16 hrs. (FIG. 21B) SCC-13 cells transfected with control or CD109 siRNA were treated with 50 μM TGF-β1 for 5 hrs. (A-B) Cell lysates were analyzed by western blot for fibronectin expression. The actin blot demonstrates equal protein loading.

Figure 22:
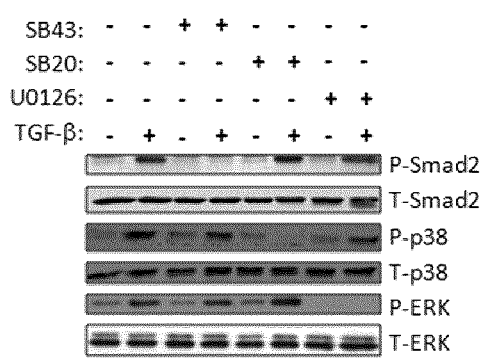

FIG. 22 illustrates the specificity of SMAD2/3 and MAPK inhibitors. HaCaT cells were pre-treated for 1 hr with 0.5 μM SB431542 (SMAD inhibitor), 1 μM SB203580 (p38 inhibitor) or 10 μM U0126 (ERK inhibitor) and treated with 15 pM TGF-β1 for 15 min. Cell lysates were analyzed for phospho-SMAD2 (P-SMAD2), phospho-p38 (P-p38) and phospho-ERK (P-ERK) by western blot. The membranes were then stripped and reprobed for total levels of the above-proteins (T-SMAD2, T-p38 and T-ERK, respectively).

Figure 23:
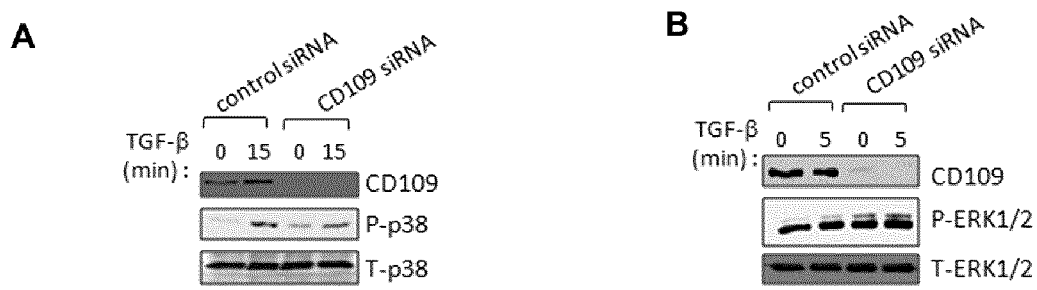
Figure 24A:
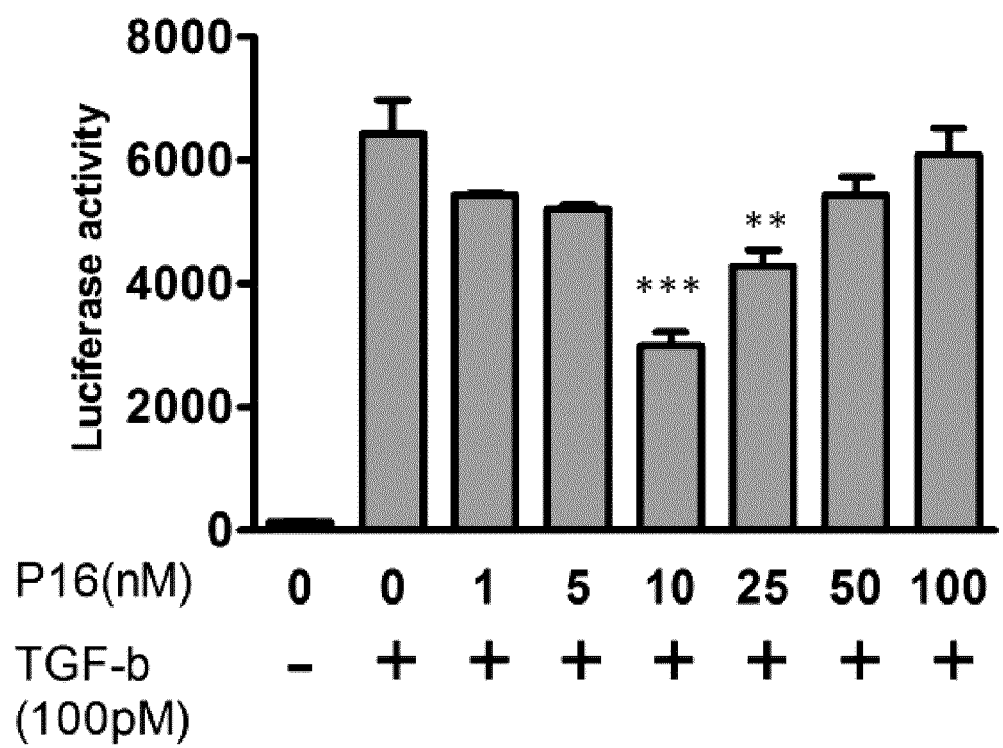
Figure 24B:
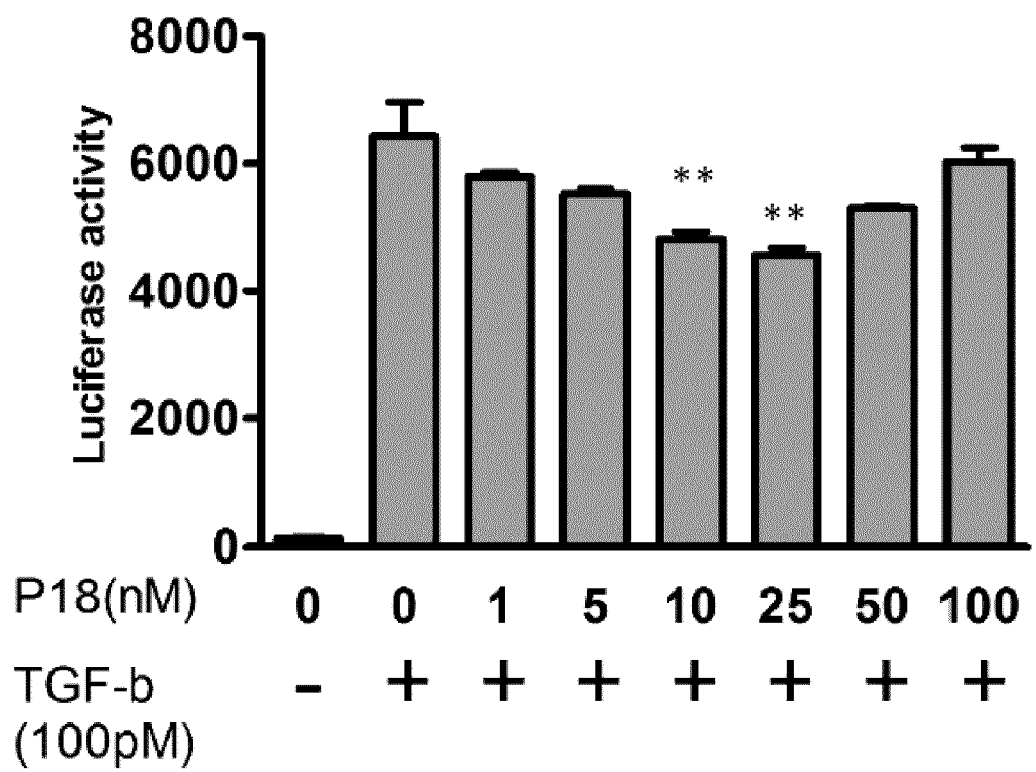
Figure 24C:
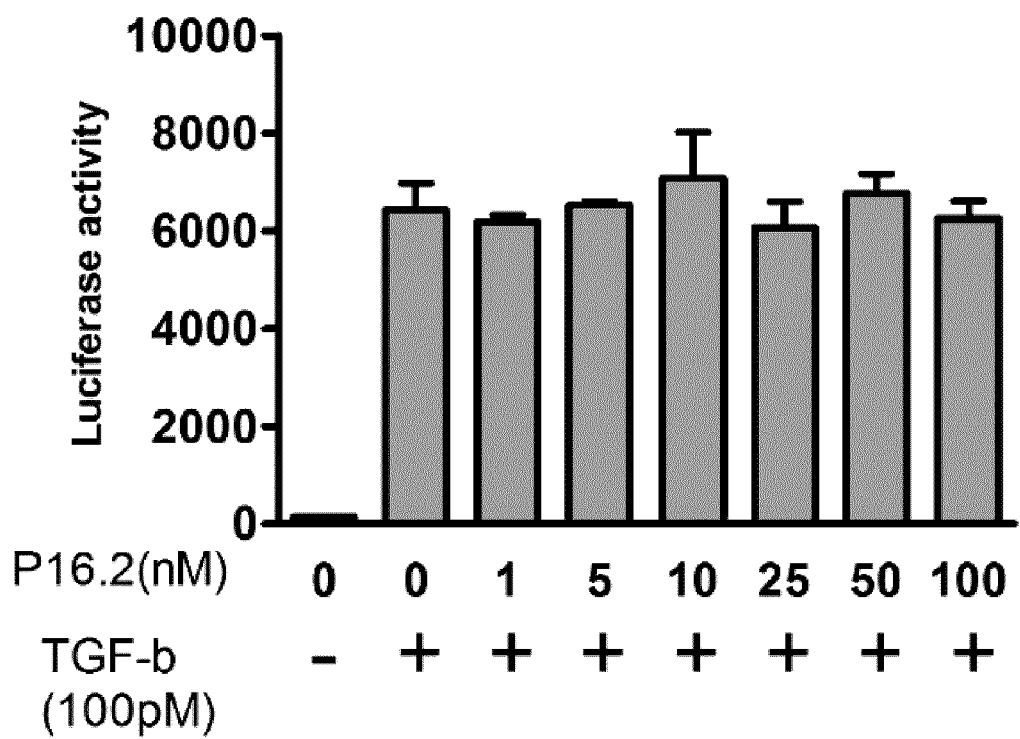
Figure 24D:
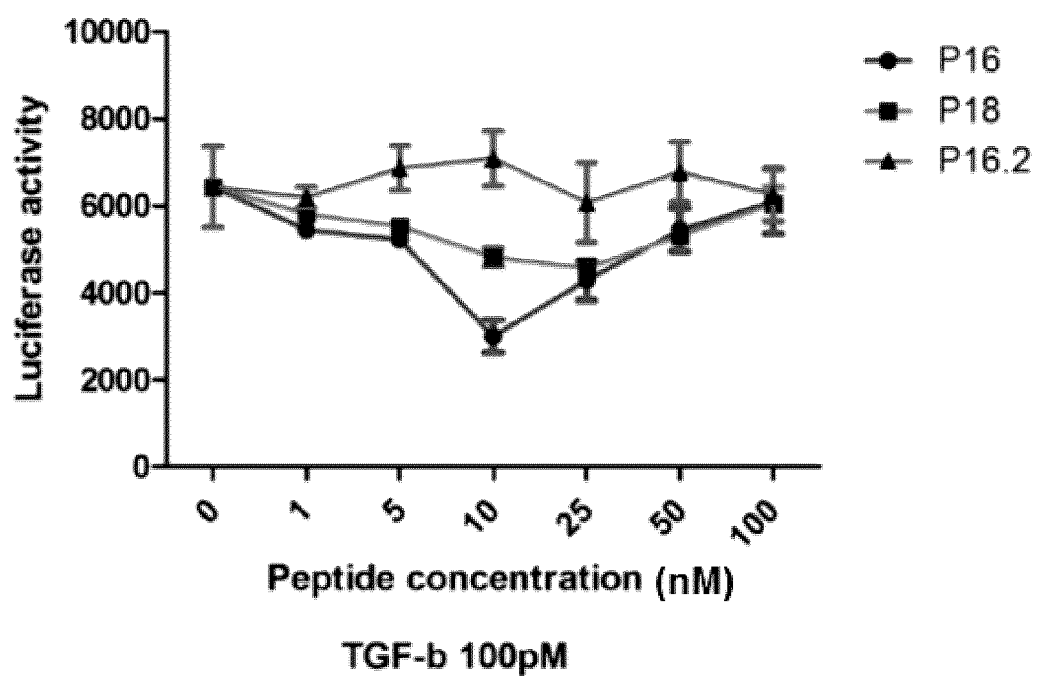
Figure 24E:
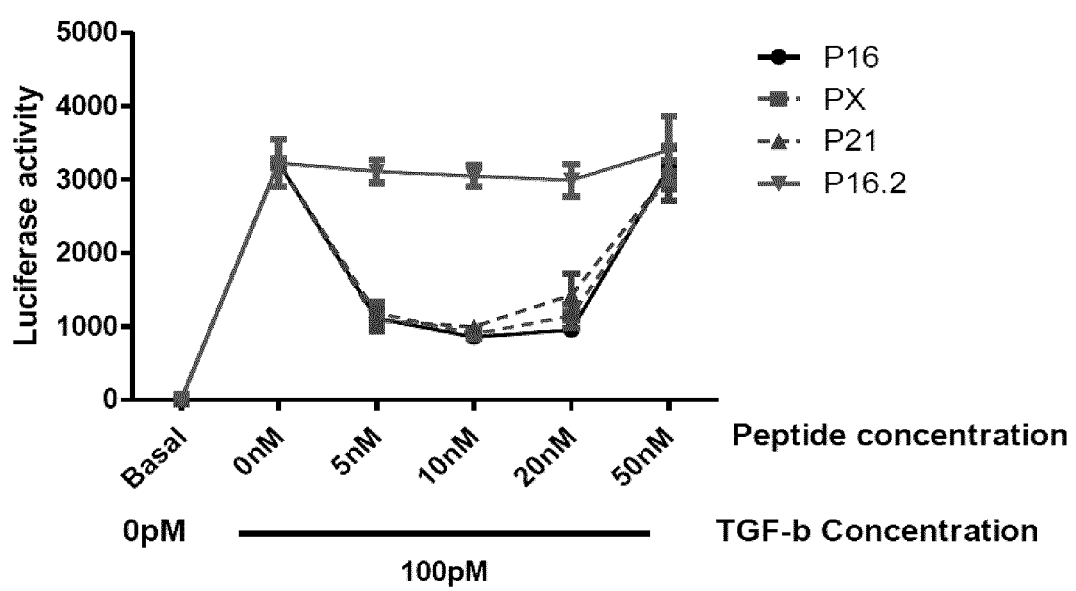

FIGS. 23A and 23B illustrate that CD109 modulates TGF-β-induced p38 and ERK MAPK activation in SCC-13 cells. SCC-13 cells transfected with control or CD-109 siRNA were treated with 15 pM TGF-β1. Cell lysates were analyzed by western blot for CD109, phospho-p38 (P-p38) and total p38 (T-p38) (FIG. 23A) or for phospho-ERK1/2 (P-ERK1/2) and total ERK1/2 (T-ERK1/2) (FIG. 23B).

FIGS. 24A-24E are graphs demonstrating the ability of CD109-based peptides to inhibit Smad3-driven transcriptional activity in a dose-dependent manner. HEK293 cells stably transfected with the Smad3-responsive $CAGA_{12}$-lux luciferase reporter were treated for 18 hours without (−) or with (+) 100 pM TGF-β1 in the presence or absence of various concentrations of P16 (FIGS. 24A and 24D), P18 (FIGS. 24B and 24D), P16.2 (FIGS. 24C and 24D), or PX (FIG. 24E) as indicated. Cell lysates were analyzed for luciferase activity and data are expressed as mean±standard deviation of relative light units (RLU).

Figure 25:
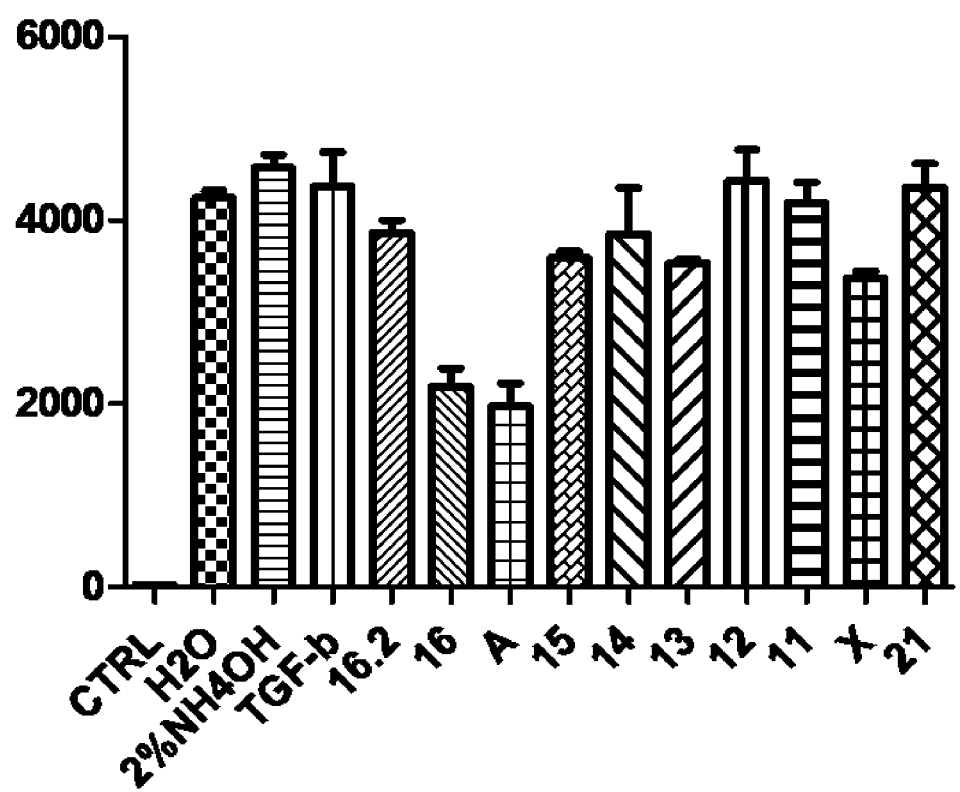

FIG. 25 is a graph showing the ability of CD109-based peptides to inhibit TGF-β-induced, Smad3-driven transcriptional activity. HEK293 cells stably transfected with the Smad3-responsive $CAGA_{12}$-lux luciferase reporter were treated for 18 hours without (−) or with (+) 100 pM TGF-b1 in the presence or absence of 10 nM of P16, P16.2, peptide A, P15, P14, P13, P12, P11, peptide X, P21, or 2% $NH_4OH$ buffer (buffer control) as indicated. Cell lysates were analyzed for luciferase activity and data are expressed as mean±standard deviation of luciferase activity. Asterisks (*) indicate that the values are significantly different from values obtained using TGF-β treatment alone (P<0.05).

Figure 26A:
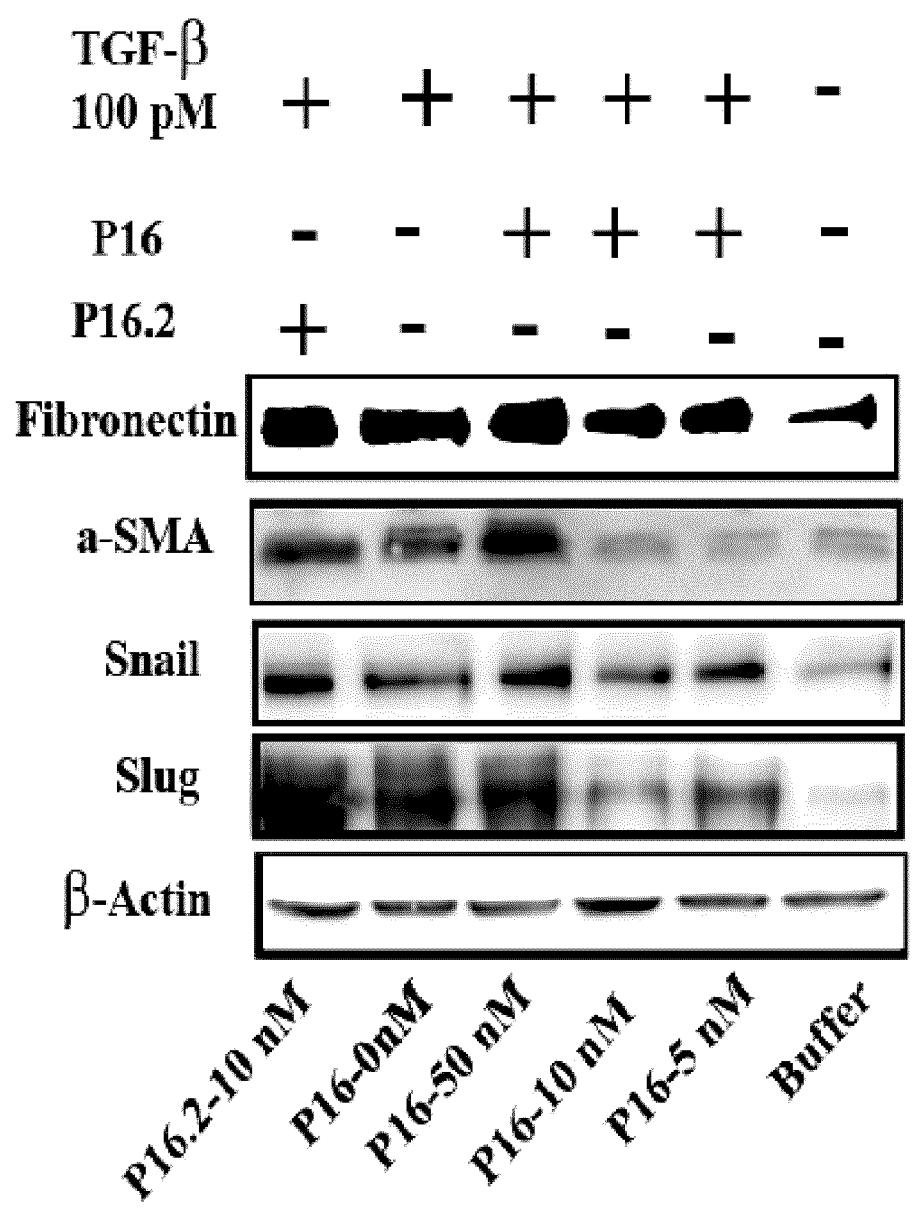
Figure 26B:
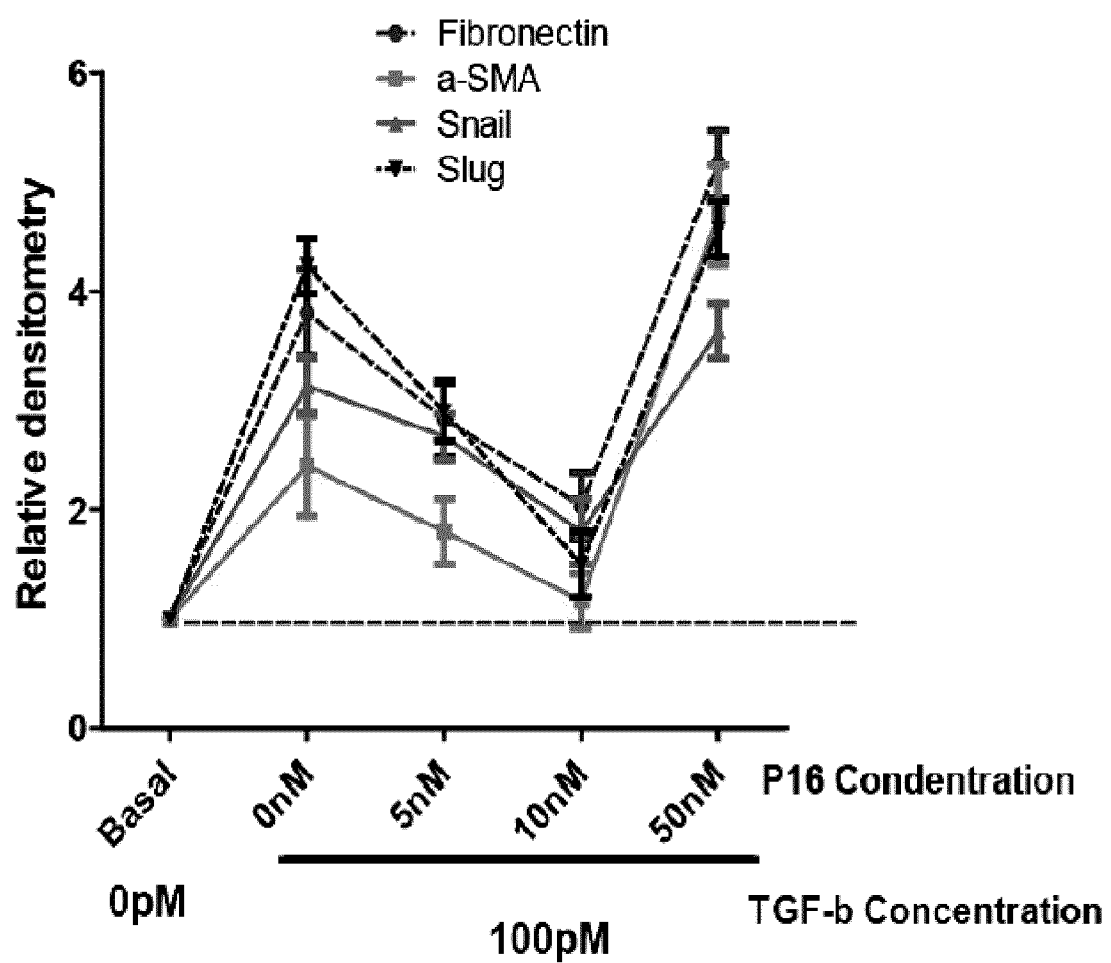

FIGS. 26A and 26B show the results of immunoblot assays demonstrating the ability of CD109-based peptide P16 to inhibit a TGF-β-induced epithelial-mesenchymal transition (EMT) response in squamous cell carcinoma (A431) cells in a dose-dependent manner. (FIG. 26A) Immunoblot analysis was carried out using cell lysates of A431 cells following incubation with TGF-β, P16, or scrambled control (P16.2) as indicated to determine expression of proteins involved in the EMT response. (FIG. 26B) Densitometry analysis was subsequently performed using the developed immunoblot to illustrate the relative expression of each protein as a function as P16 concentration as indicated.

Figure 27A:
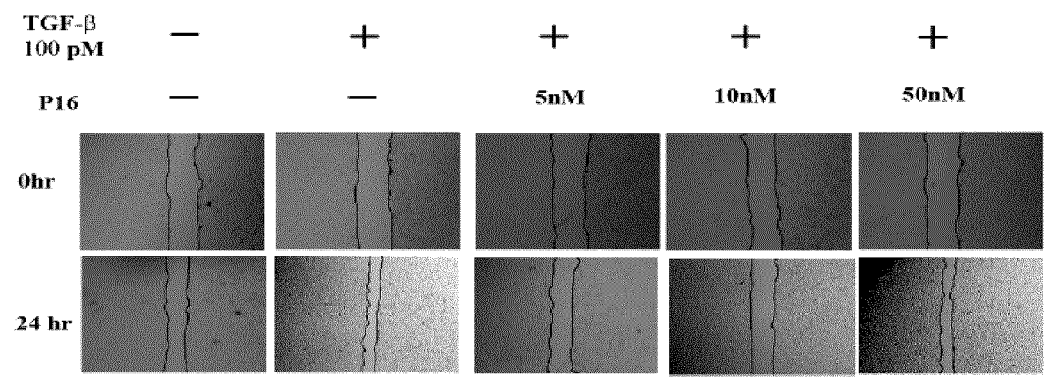
Figure 27B:
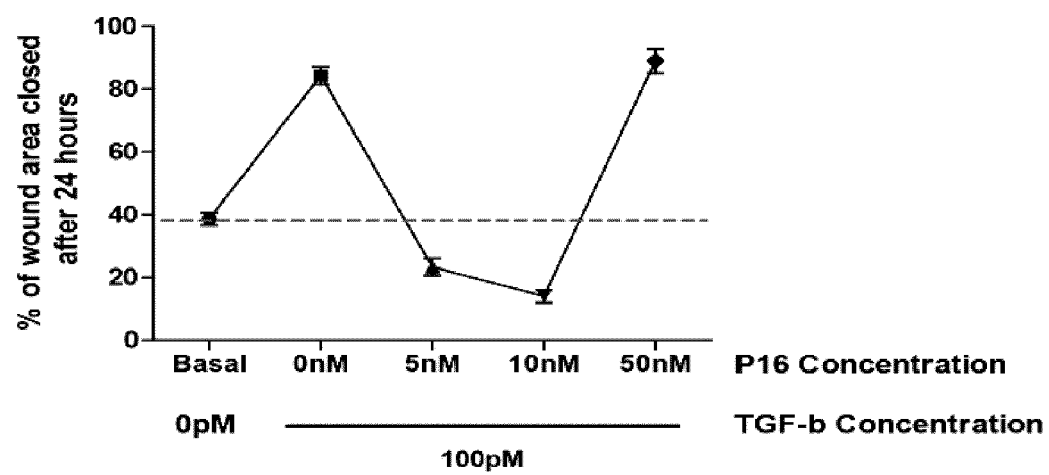

FIGS. 27A and 27B demonstrate the ability of CD109-based peptide P16 to inhibit squamous cell carcinoma (A431) cell migration in a dose-dependent manner. A431 cells were grown to 80-90% confluence and serum-starved overnight. The next day, cells were scratched with a plastic pipette tip (time 0 hour) and then left untreated or treated for 24 hours with 100 pM TGF-β1 alone or in the presence of P16 as indicated. (FIG. 27A) Digital images were captured at 0 h and 24 h using an EVOS XL Core microscope. (FIG.

27B) Micrographs were subsequently quantitated to determine the percentage of the wound area that had closed following 24 hours in the presence or absence of P16, as indicated.

Figure 28A:
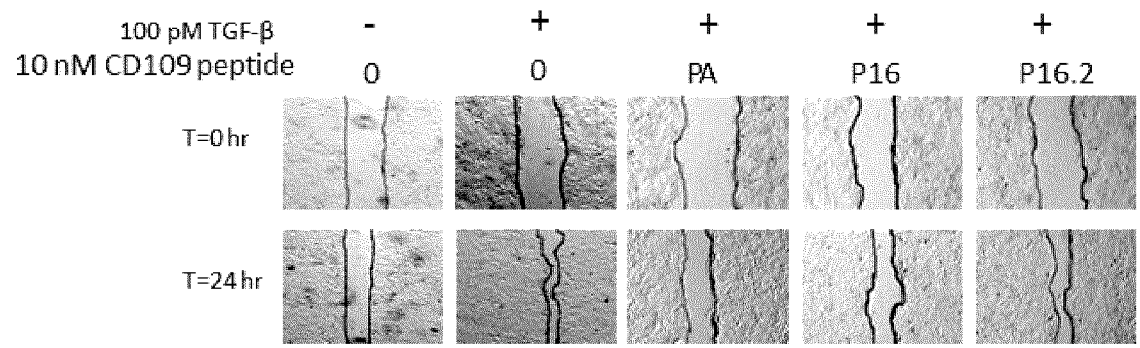
Figure 28B:
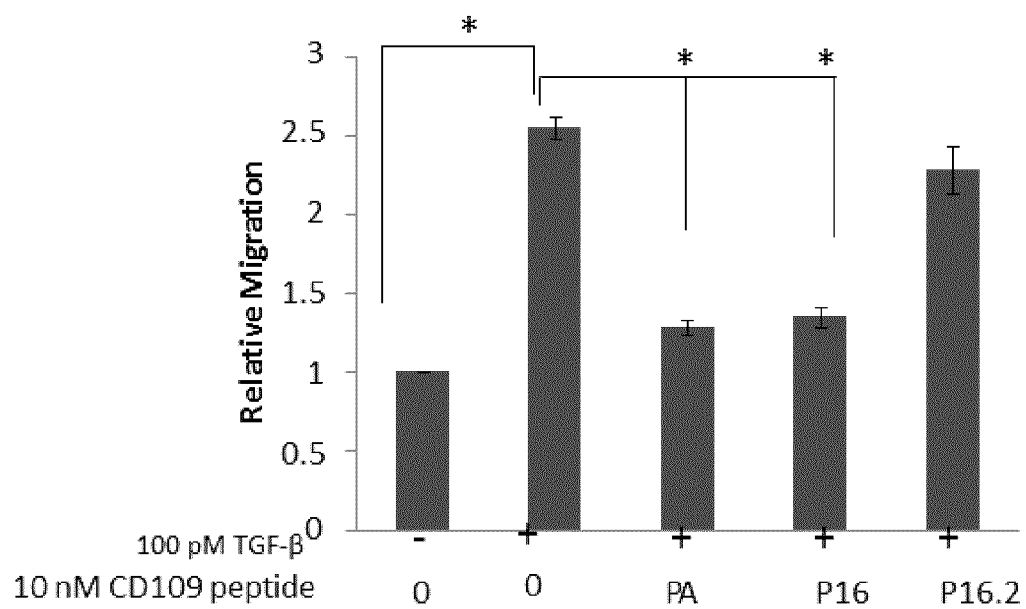

FIGS. 28A and 28B show the results of wound closure assays performed using human keratinocyte HaCat cells. These data demonstrate the ability of CD109-based peptide P16 to suppress HaCat cell migration in a sequence-dependent manner. (FIG. 28A) Human Keratinocyte HaCat cells were starved for 24 hours, scratched with pipette tips, and then treated with 100 pM TGF-β and 10 nM CD109-based peptides as indicated for 24 hours. Microscopy images were taken at time 0 and 24 hours of treatment. (FIG. 28B) Migration distances were measured using the Image J software platform. Error bars represent mean+/−standard deviation, asterisk designates a P value of <0.05.

Figure 29A:
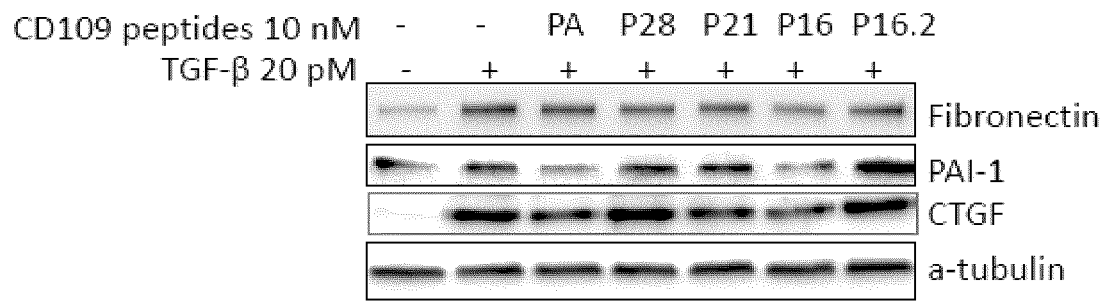
Figure 29B:
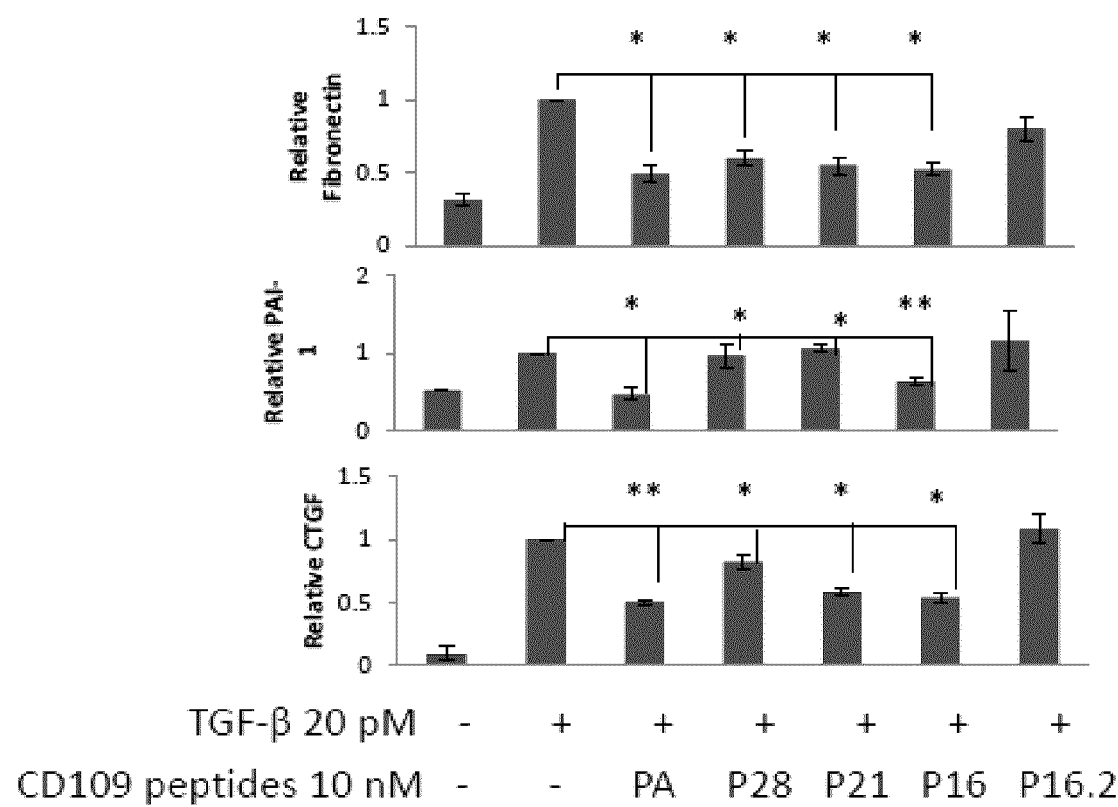

FIGS. 29A and 29B demonstrate the ability of CD109-based peptides to inhibit a TGF-β-induced fibrotic response in human fibroblasts. Human primary fibroblasts were starved for 36 hours, then treated with 20 pM TGF-β and 10 nM CD109-based peptide as indicated for 24 hours. (FIG. 29A) Cell lysates were separated by gel electrophoresis, transferred to a membrane, and immunoblotted with antibodies against fibronectin, PAI-1, CTGF, and α-tubulin. (FIG. 29B) The data shown represent the mean expression levels of 3 different biological replicates calculated by densitometry of fibronectin, PAI-1, and CTGF intensity levels normalized to α-tubulin. Error bars represent the standard deviation of the replicate experiments. A single asterisk designates a t test P value of less than 0.05, and a double asterisk indicates a P value of less than 0.01.

Figure 30A:
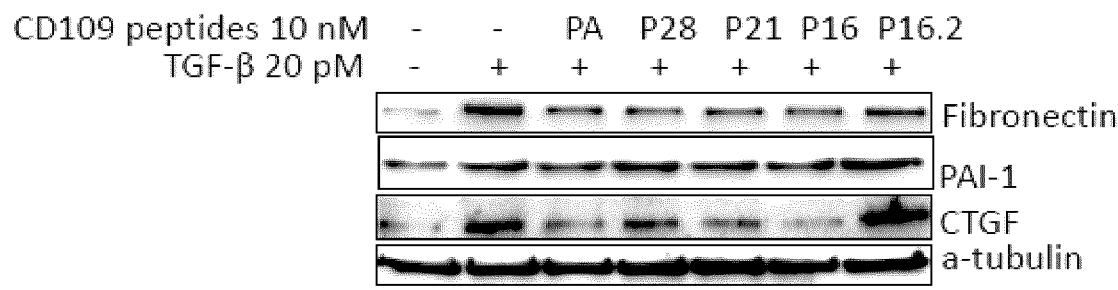
Figure 30B:
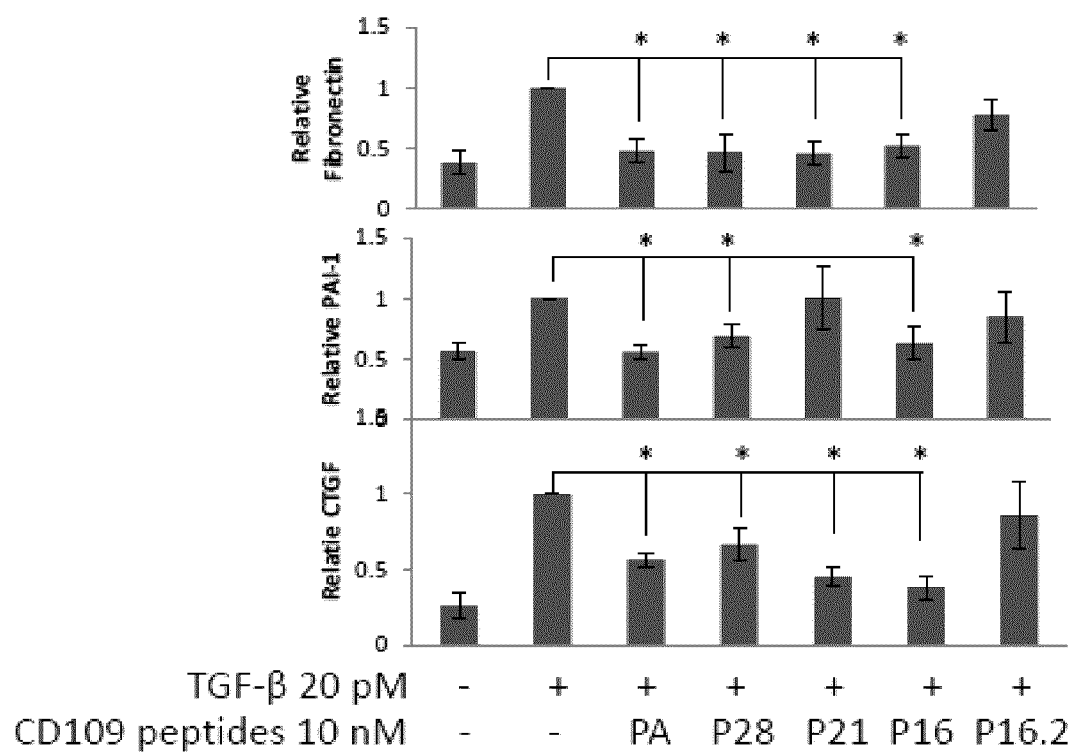

FIGS. 30A and 30B demonstrate the ability of CD109-based peptides to inhibit a TGF-β-induced fibrotic response in primary human fibroblasts isolated from scleroderma patients. Fibroblasts were starved for 36 hours, then treated with 20 pM TGF-β and 10 nM CD109-based peptide as indicated for 24 hours. (FIG. 30A) Cell lysates were separated by gel electrophoresis, transferred to a membrane, and immunoblotted with antibodies against the indicated proteins. (FIG. 30B) The data shown represent the mean expression levels of 3 different biological replicates calculated by densitometry of fibronectin, PAI-1, and CTGF intensity levels normalized to α-tubulin. Error bars represent the standard deviation of the replicate experiments. A single asterisk designates a t test P value of less than 0.05.

Figure 31A:
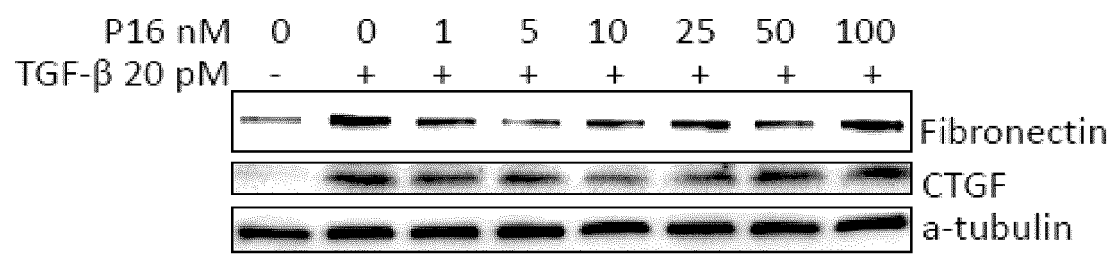
Figure 31B:
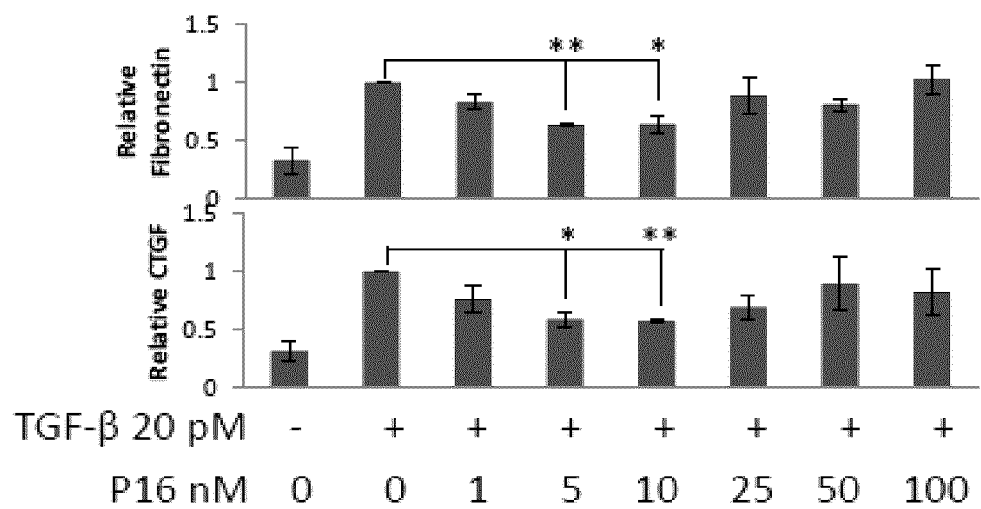

FIGS. 31A and 31B demonstrate the ability of CD109-based peptide P16 to inhibit a TGF-β-induced fibrotic response in primary human fibroblasts isolated from scleroderma patients in a dose-dependent manner. Fibroblasts were starved for 36 hours, then treated with 20 pM TGF-β and various concentrations of P16 as indicated for 24 hours. (FIG. 31A) Cell lysates were separated by gel electrophoresis, transferred to a membrane, and immunoblotted with antibodies against the indicated proteins. (FIG. 31B) The data shown represent the mean expression levels of 3 different biological replicates calculated by densitometry of fibronectin, PAI-1, and CTGF intensity levels normalized to α-tubulin. Error bars represent the standard deviation of the replicate experiments. A single asterisk designates a t test P value of less than 0.05, and a double asterisk indicates a P value of less than 0.01.

Figure 32A:
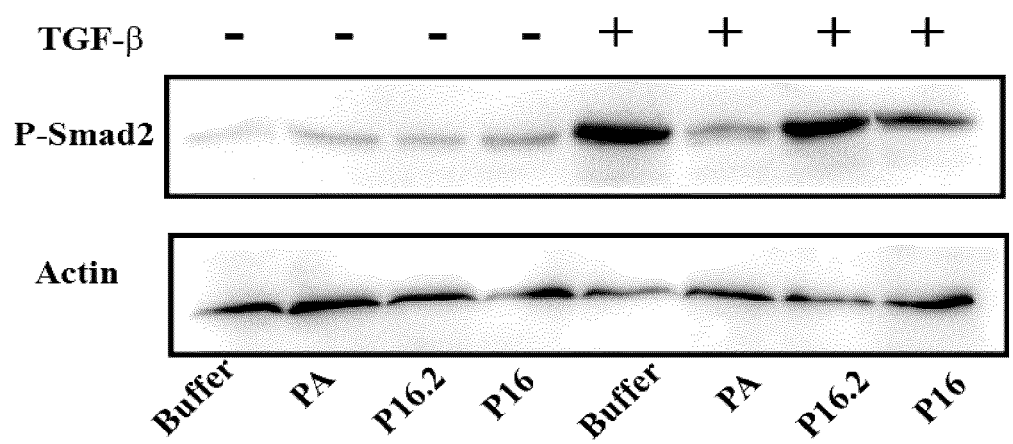
Figure 32B:
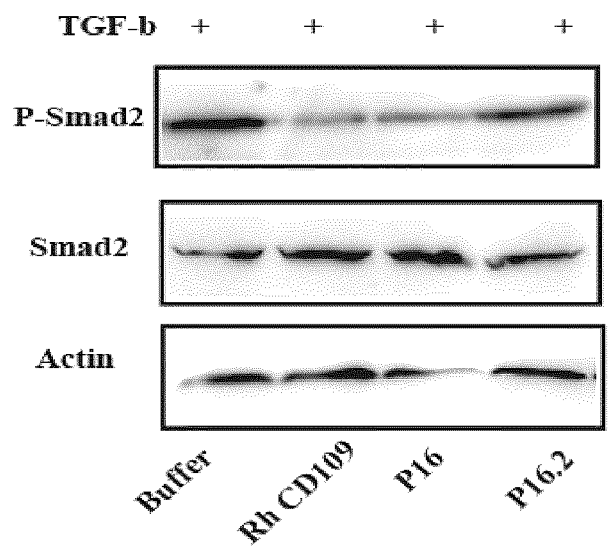

FIGS. 32A and 32B show that CD109 derived peptide P16 and PA inhibit TGF-b-induced phosphorylation of Smad2 in squamous cell carcinoma (A431) cells. A431 cancer cells treated with 10 nM of P16.2 (negative peptide control), P16 or PA in the absence or presence of 100 pM TGF-b, followed by 45 min of incubation at 4 C. Cells lysates were analyzed by Western blot using an anti-phosphoSmad2 antibody. Actin expression was used as loading control.

Figure 33:
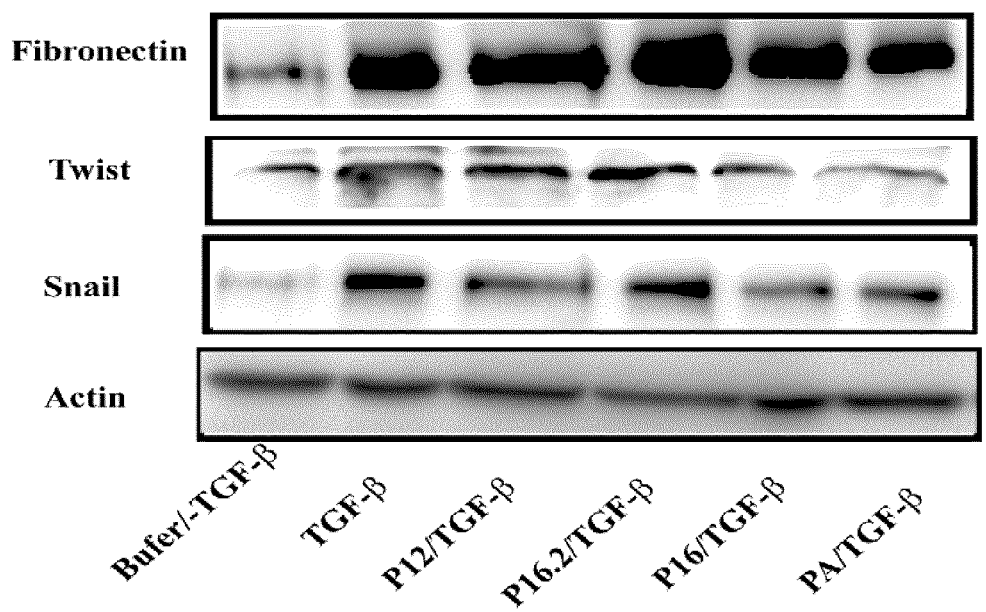

FIG. 33 shows that CD109 derived peptide P16 and PA (but not P12) inhibit TGF-b induced EMT response in squamous cell carcinoma (A431) cells. A431 cancer cells treated with 10 nM of P16.2 (negative peptide control), P12, P16 or PA in the absence or presence of 100 pM TGF-b, followed by 24 hrs of incubation. Cells lysates were analyzed by Western blot for the expression of Fibronectin (mesenchymal marker), Snail and Twist (EMT markers). Actin expression was used as loading control.

Figure 34A:
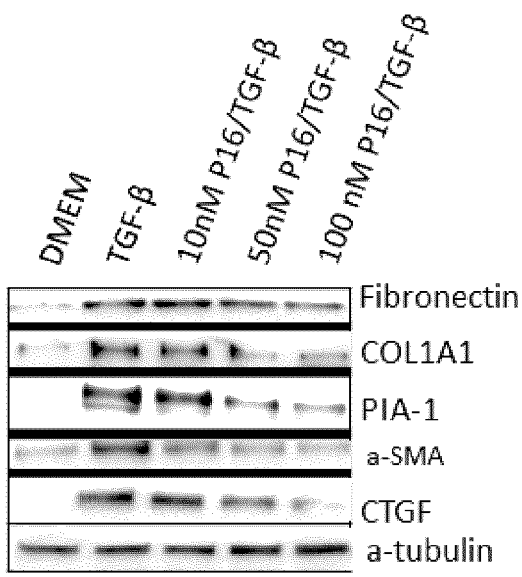
Figure 34B:
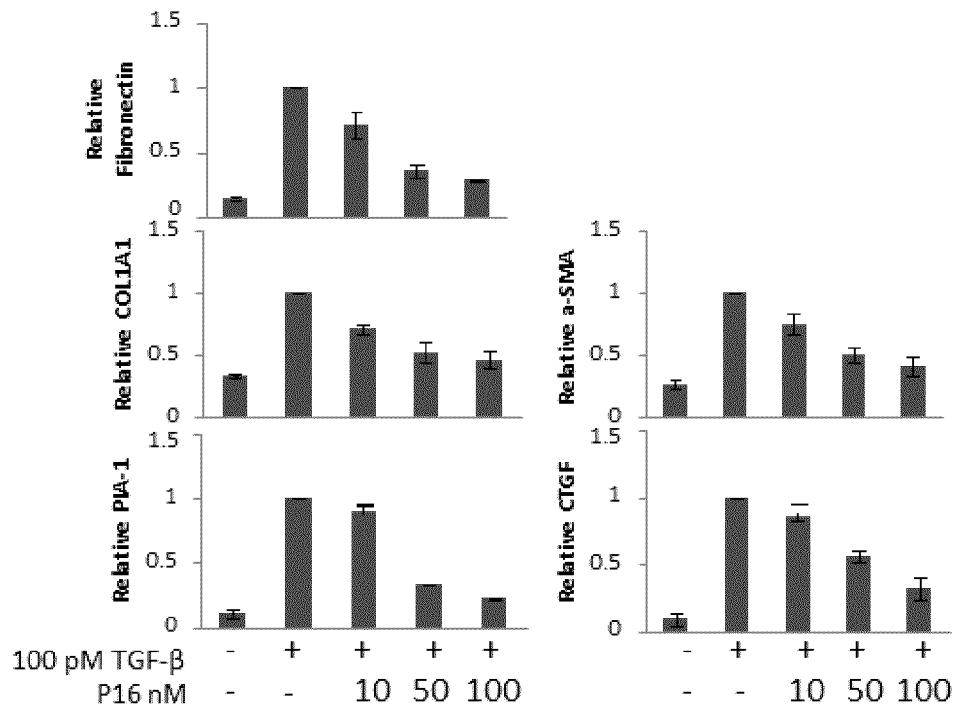

FIGS. 34A and 34B demonstrate the ability of CD109-based peptide P16 to attenuate the TGF-β-induced expression of fibronectin, collagen (COL1A1), plasminogen activator inhibitor-1 (PAI-1), α-smooth muscle actin (α-SMA), and connective tissue growth factor (CTGF). Human fibroblasts were starved for 36 hours, then treated with 100 pM TGF-β and different dosage of P16 for 24 hrs. (FIG. 34A) Cell lysates were separated by gel electrophoresis, transferred to a membrane, and immunoblotted with antibodies against each of the indicated proteins. (FIG. 34B) Densitometry analysis was subsequently carried out to quantitate the expression of each of the indicated proteins as a function of P16 concentration.

Figure 35A:
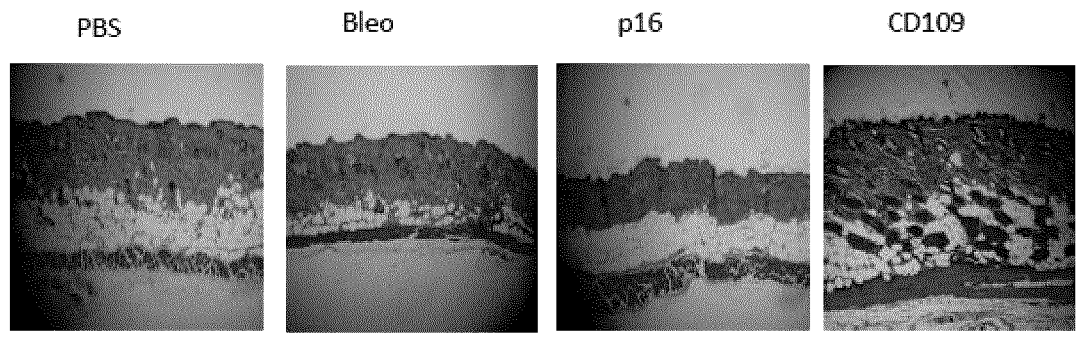
Figure 35B:
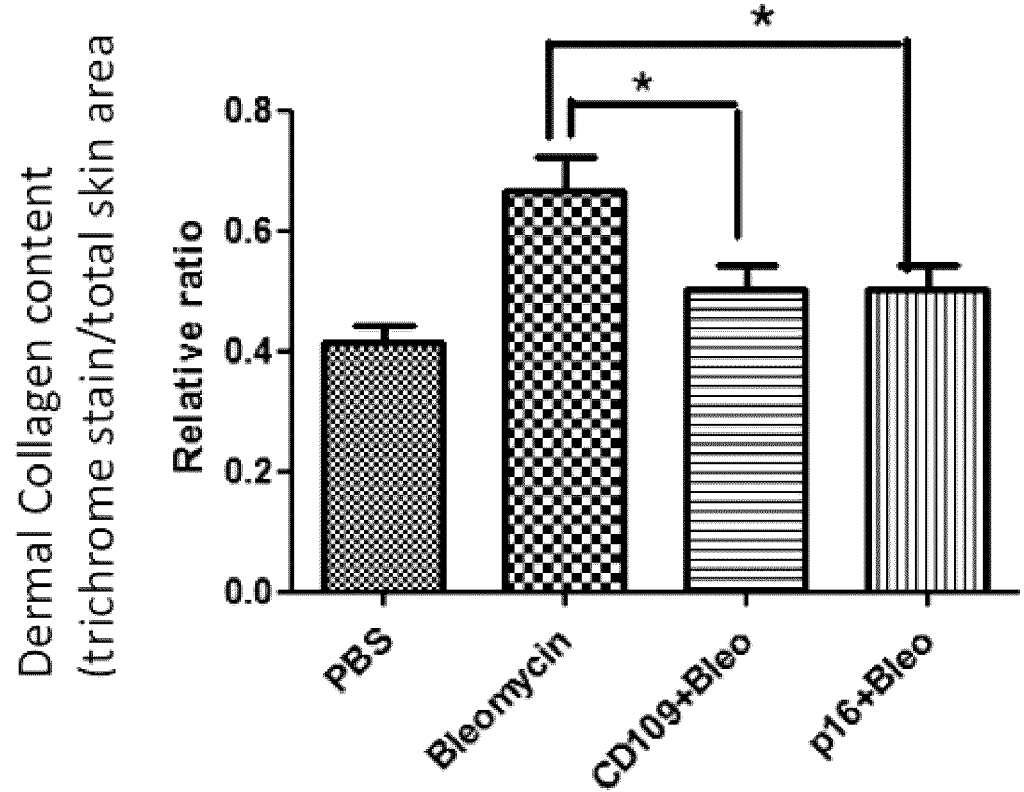

FIGS. 35A and 35B demonstrate the ability of CD109-based peptide P16 to inhibit dermal collagen content in bleomycin-induced mouse models of scleroderma. Wild type mice were treated with bleomycin (5 μg) to induce skin fibrosis or PBS (negative control). Mice were treated with CD109 (1 μg), P16 (1 μg), or PBS by 100 μL subcutaneous injection every other day for 28 days for a total of 14 injections. (FIG. 35A) P16 was found to be capable of reducing dermal thickness and collagen content as assessed by trichrome staining. (FIG. 35B) P16 was found to be capable of reducing dermal collagen content as assessed by measuring the ratio of trichrome stain to total skin area.

Figure 36:
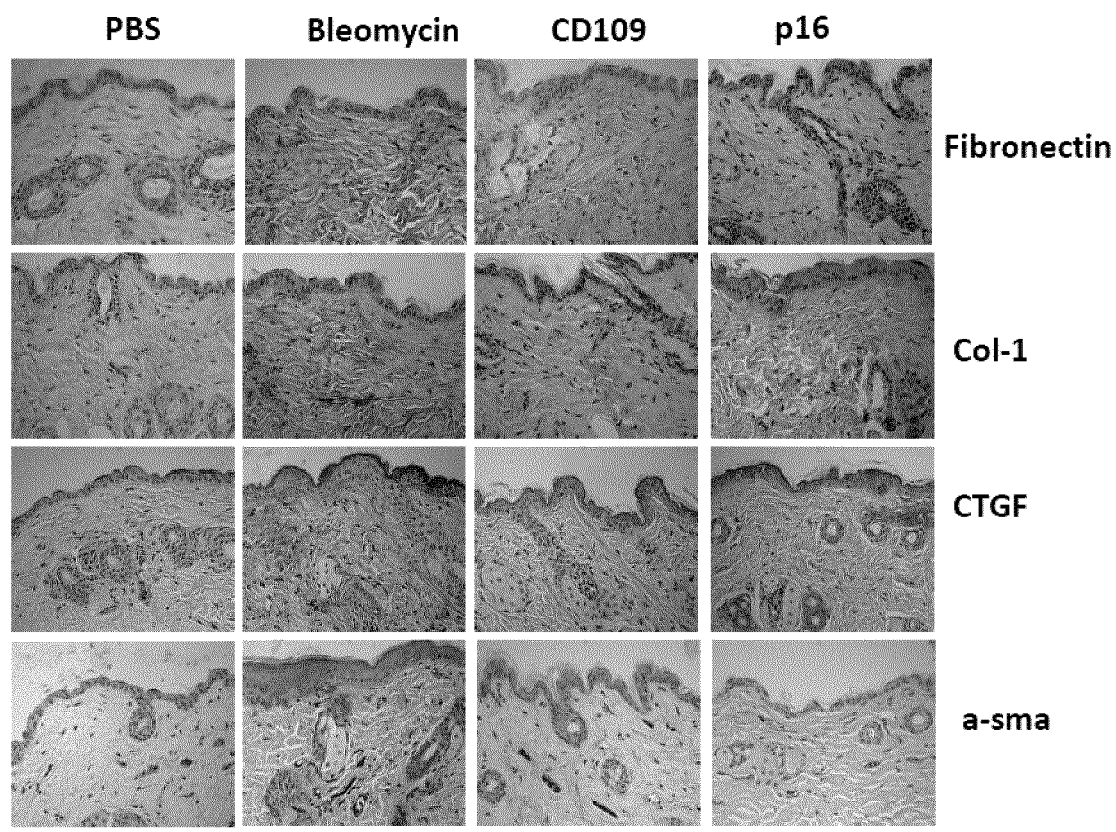

FIG. 36 shows that Recombinant CD109 or P16 peptide reduces extracellular matrix production in a bleomycin (bleo)induced skin fibrosis model (scleroderma model) in vivo. Mice were injected intradermally with bleomycin (5 mg) in 100 ml PBS or PBS alone every second day for 28 days. Mice were co-injected without or with 1.0 mg recombinant CD109 protein or P16 peptide every second day for 28 days (14 mg total). Skin tissue was harvested and immunohistochemical analysis was performed for the detection of Fibronectin, α-sma, CTGF and Type-1 Collagen. Representative images of sections of skin derived from CD109 and p16 treated mice on day 28 after initial bleomycin or PBS treatment are shown. A total of 4-6 different mice per treatment group were analyzed. Original magnification ×20.

Figure 37:
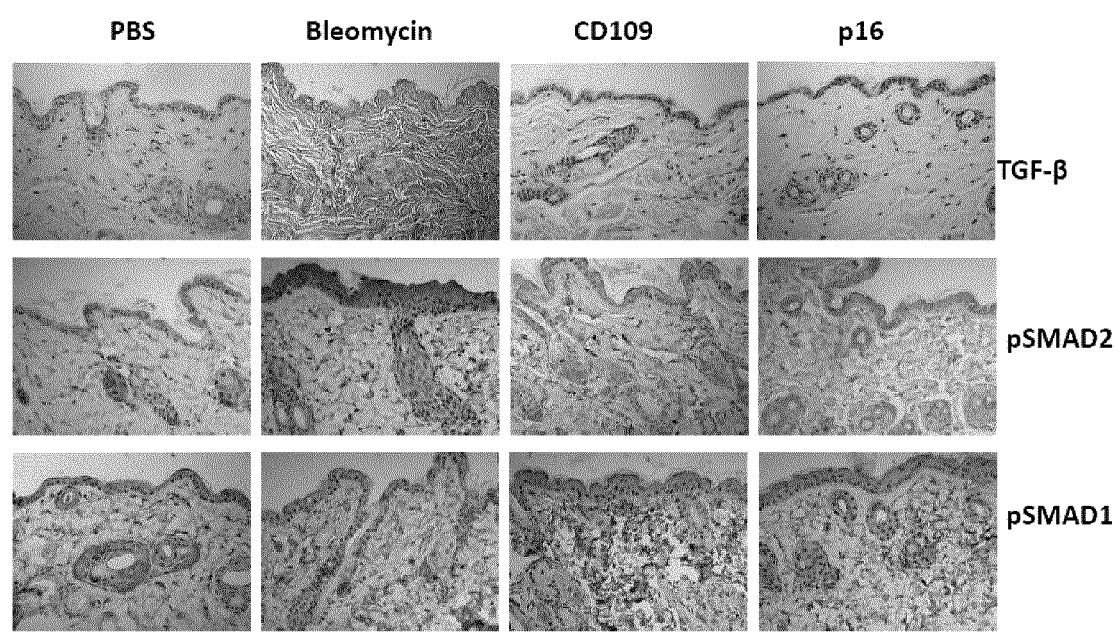

FIG. 37 shows that Recombinant CD109 or P16 peptide reduces TGF-β expression and SMAD2 phosphorylation while enhancing SMAD1 phosphorylation in a bleomycin (bleo)induced skin fibrosis model (scleroderma model) in vivo. Mice were injected intradermally with bleomycin (5 mg) in 100 ml PBS or PBS alone every second day for 28 days. Mice were co-injected without or with 1.0 mg recombinant CD109 protein or P16 peptide every second day for 28 days (14 mg total). Skin tissue was harvested and immunohistochemical analysis was performed for the detection of phospho-Smad2, phospho-Smad1 and TGF-β levels. Representative images of sections of skin derived from CD109 and p16 treated mice on day 28 after initial bleomycin or PBS treatment are shown. A total of 4-6 different mice per treatment group were analyzed. Original magnification ×20.

Figure 38A:
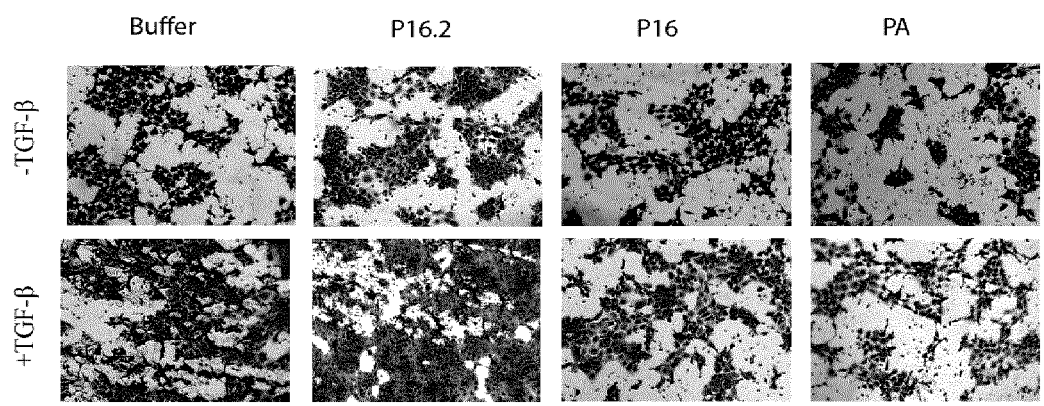
Figure 38B:
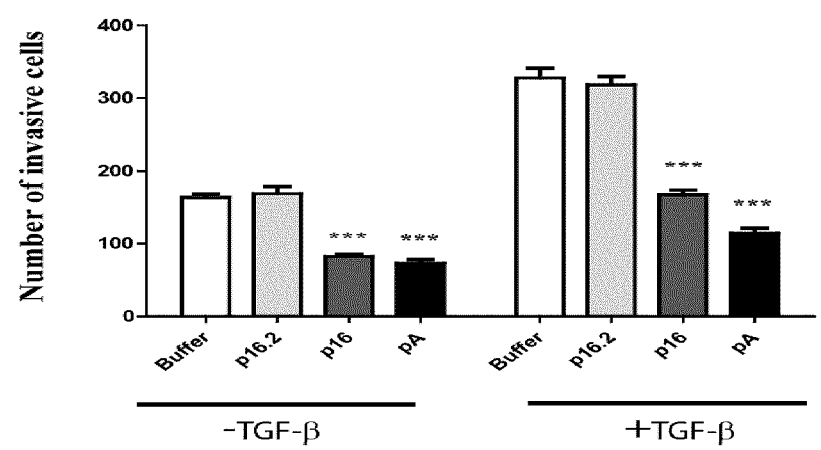
Figure 39A:
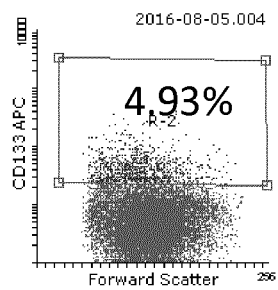
Figure 39B:
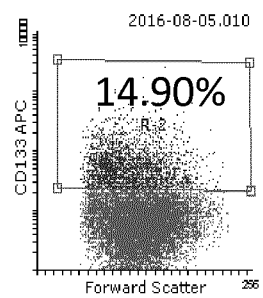
Figure 39C:
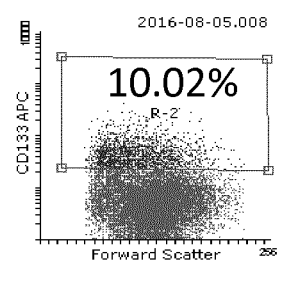
Figure 39D:
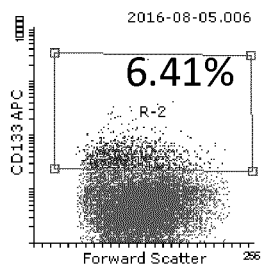
Figure 39E:
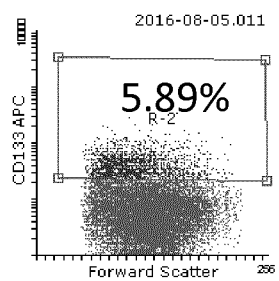
Figure 39F:
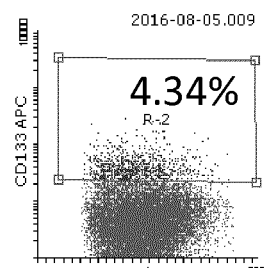
Figure 39G:
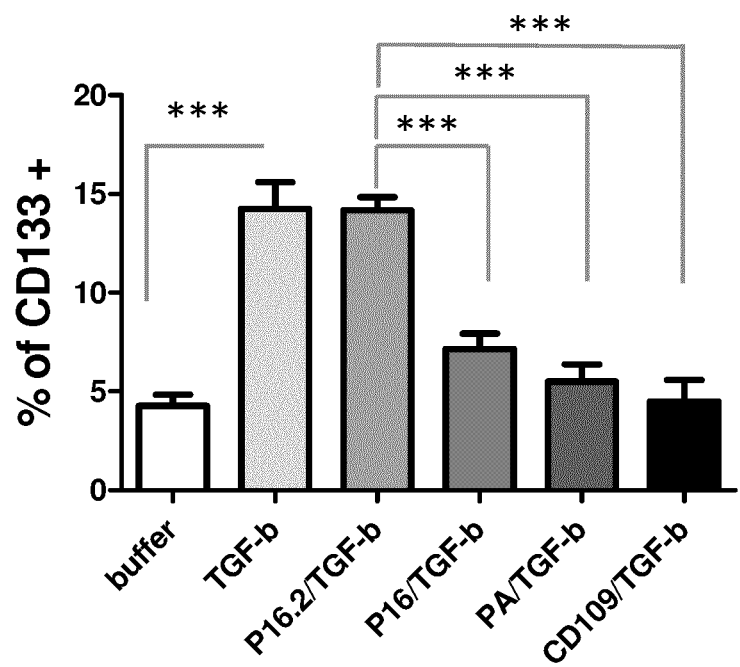

FIGS. 38A and 38B show that CD109 derived peptide P16 and PA significantly inhibit TGF-b induced cellular invasion in vitro in squamous cell carcinoma (A431) cells, as detected by a Matrigel invasion Assay. A431 cancer cells (8000 cells) were seeded on a BioCoat™ Matrigel® Invasion Chamber and treated with 10 nM of P16.2 (negative peptide control), P16 or PA in the absence or presence of 100 pM TGF-b, followed by 24 hrs of incubation. Invasive cells (in the lower chambers) were stained by crystal violet dye, photographed and counted. Representative photos (A) and statistical plots of invasion (B) are shown. The data are shown as mean±SD of the number of invasive cells for three independent experiments. P<0.01 and *P<0.001 as compared with controls. Magnification, ×100

FIGS. 39A-39G show that Recombinant CD109 and CD109-derived peptides inhibit the number of cancer stem cells (CD133 positive cells). Squamous cell carcinoma (epidermoid A431 and head and neck FaDu) cells were stimulated with 100 pM of TGF-b1, then treated with 10 nM of peptide 16.2, P16, PA or CD109 for 24 hours. Cells were analysed by Flow cytometry and CD133 positive cell population, which represent cancer stem cell population, were quantified.

Figure 40A:
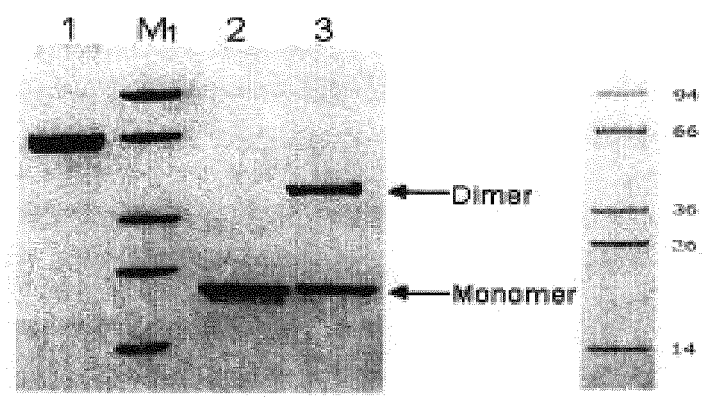
Figure 40B:
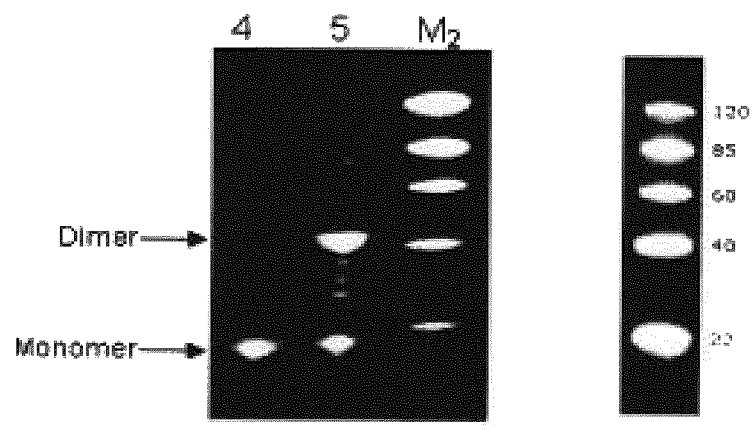

FIGS. 40A and 40B show that peptide A exists as both dimeric and monomeric forms. Peptide A was bacterially expressed and purified by affinity chromatography. Purified peptide A was analyzed by SDS-PAGE under reducing and non-reducing conditions and visualized by Coomassie blue staining (FIG. 40A) or Western blot analysis using an anti-His antibody (FIG. 40B). In FIG. 40A, lane 1 of the SDS-PAGE analysis corresponds to 2.00 μg of BSA, land 2 corresponds to 2.00 μg of CD109-derived peptide A (under reducing conditions), and lane 3 corresponds to peptide 2.00 μg of peptide A under non-reducing conditions. In FIG. 40B, lane 4 of the Western Blot corresponds to peptide A under reducing conditions, and lane 5 corresponds to peptide A under non-reducing conditions. The positions of the dimer and monomer are indicated by arrows. The SDS-PAGE was run on 4%-20% gradient gel. M1 and M2 designate protein markers (GENSCRIPT®).

Figure 41:
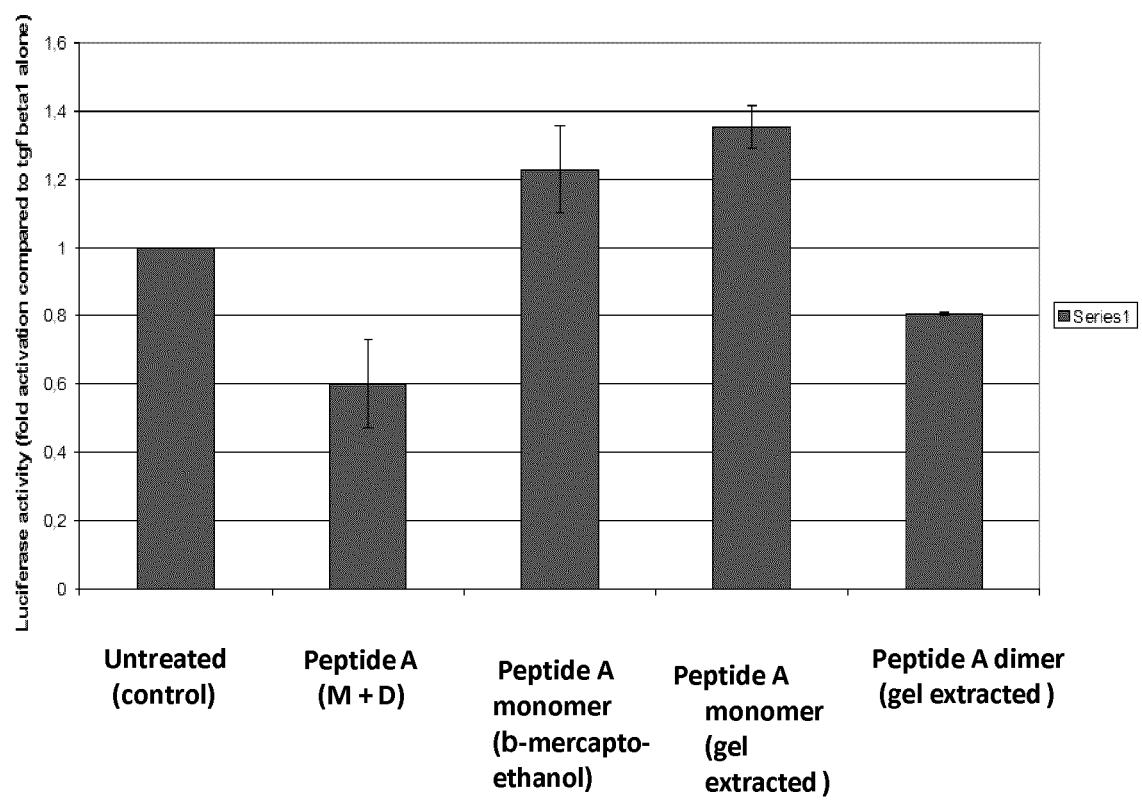

FIG. 41 shows that peptide A dimer inhibits whereas peptide A monomer potentiates TGF-b-dependent Smad3 (CAGA$_{12}$-lux) transcriptional activity in 293 cells. HEK293 cells stably transfected with the Smad3-responsive CAGA$_{12}$-lux luciferase reporter construct were incubated with dimeric or monomeric forms of peptide A as indicated and treated with 100 pM TGF-b overnight. Cell lysates were analyzed for luciferase activity. Data are presented as fold-activation compared to TGF-b1 treatment alone (scaled to 1.0). M+D, mixture of monomer and dimer.

Figure 42:
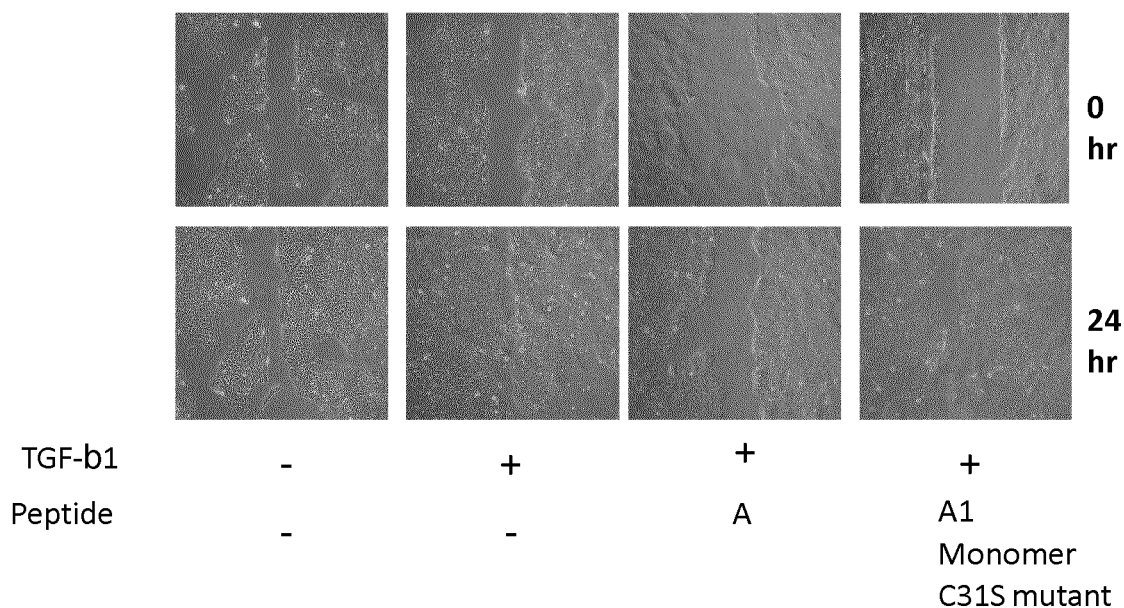

FIG. 42 shows that peptide A inhibits TGF-b1 induced migration in A431 cells. Cells were scratched with a pipette tip and treated without or with 100 pM TGF-b1 alone or in the presence of 10 nM Peptide A or Peptide A1 (C31S mutant). Pictures were taken at 0 and 24 hrs. Peptide A but not Peptide A1 inhibits TGF-b-induced migration in A431 cells. Peptide A contains monomeric and dimeric forms whereas Peptide A1 contains a C31S mutation to prevent intermolecular disulfide bond formation so that it forms monomers only.

DETAILED DESCRIPTION

The invention provides TGF-β antagonists containing a low-molecular weight TGF-β-binding peptide. The TGF-β-binding peptides described herein are derived from CD109, a high-molecular weight protein that binds endogenous TGF-β in an inhibitory fashion so as to attenuate TGF-β signaling. The present invention is based in part on the discovery that various low-molecular weight fragments of CD109 are capable of binding TGF-β in solution without the need for flanking N-terminal and C-terminal domains. A motif within CD109 containing a TGF-β-binding pharmacophore, ETWIWLDTNMG (SEQ ID NO: 4), has presently been discovered that imparts TGF-β inhibitory activity to a low-molecular weight peptide. The presence of this motif renders the peptide capable of binding and inhibiting TGF-β signaling, for instance, as observed in the form of reduced expression of genes under the control of transcription factors activated by TGF-β signal transduction, such as Smad3. TGF-β-binding peptides containing this motif, such as a peptide having the amino acid sequence of any one of SEQ ID NOs: 5, 6, 12-15, and 22-25, may be capable of attenuating the expression of proteins involved in the fibrotic response, such as fibronectin, plasminogen activator inhibitor-1 (PAI-1), and connective tissue growth factor (CTGF). Due to their capacity for inhibiting TGF-β activity, the TGF-β-binding peptides described herein can be used as TGF-β antagonists for the treatment of a variety of pathological conditions, including fibrosis, autoimmune diseases, and cancers, among others. The TGF-β antagonists described herein may include a TGF-β-binding peptide and, for example, one or more additional moieties (e.g., peptides, small molecules, or proteins) that do not interfere with binding of the peptide to TGF-β. Alternatively, a TGF-β antagonist may consist of the TGF-β-binding peptide and not contain any additional elements.

An additional discovery underlying the present invention is that, surprisingly, low-molecular weight peptides containing the amino acid sequence of SEQ ID NO: 4 do not aggregate in solution. A barrier that has hindered the development of high-molecular weight proteins and large (e.g., >10 kDa) fragments thereof has been the propensity of various peptides to aggregate in aqueous solution. In accordance with the present disclosure, there is provided peptides capable of antagonizing at least one TGF-β's biological activity while exhibiting a very low propensity to aggregate during storage. The peptides are derived from the CD109 polypeptide and can be used for the prevention, treatment and/or alleviation of symptoms associated with fibrosis.

Peptidic TGF-β Antagonists

As shown herein, peptide X, a 40-amino acid fragment of the CD109 polypeptide (having the amino acid sequence shown in SEQ ID NO: 1) has the propensity to aggregate during storage. In the conditions described in Example 1, peptide X was shown to aggregate when stored for 2 hours at 4° C. (e.g., when dissolved at a concentration of 50 mM in a Tris-HCl (pH=7.0) solution). The aggregation of peptide X reduced its ability to antagonize at least some of TGF-β's biological activity (e.g., reduction of the transcription induced by Smad3, reduction in the expression of PAI-1, etc.). However, it has presently been discovered that the conversion of aggregated peptide X to an un-aggregated form partially restores its ability to antagonize TGF-β's biological activity.

In addition to peptide X, some TGF-β peptide antagonists, such as high-molecular weight TGF-β antagonists, may have a propensity to aggregate. Peptide aggregation is considered a common and troubling manifestation and is encountered in almost all stages of peptide drug development. Peptide aggregation, along with other physical and/or chemical instabilities of proteins, remains one of the major road blocks hindering rapid commercialization of potential peptide drug candidates. Moreover, peptide aggregation is associated with adverse immunogenic side effects underscoring the importance for the design of peptides with a low propensity to (self) aggregate, particularly at the early stages of peptide (drug) development.

To further understand why peptide X has a propensity to aggregate, its amino acid sequence was further analyzed. As discussed in Example 1, the amino acid motif ETWIWL (SEQ ID NO: 11) associated with binding with TGF-β (and presumably involved in antagonizing TGF-β's biological activity) was identified as favoring aggregation of peptide X. Nevertheless, a series of peptides that contain the ETWIWL motif were designed and tested These included Peptide X1/P28, Peptide X2/P21, peptide X3, Peptide X4, Peptide 16/P16, Peptide 11/P11, Peptide 16.1/P16.1 and Peptide 16.2/P16.2.

As also shown herein, some of the fragments of peptide X (referred to herein as peptidic TGF-β antagonists) lack or have a low propensity to aggregate upon storage and exhibit antagonist activity against TGF-β. Unexpectedly, the peptidic TGF-β antagonists contain the hydrophobic, aggregation-prone amino acid motif ETWIWL (SEQ ID NO: 11) but do not have the propensity to aggregate. As such, the peptidic TGF-β antagonists represent a class of therapeutic peptides which will not aggregate and may have increased stability during storage.

The peptidic TGF-β antagonists may have, for instance, up to 28 amino acids. In some embodiments, the peptidic TGF-β antagonists contain from 12 to 28 amino acids, such as from 12 to 27 amino acids, from 12 to 26 amino acids, from 12 to 25 amino acids, from 12 to 24 amino acids, from 12 to 23 amino acids, from as to 22 amino acids, from as to 21 amino acids, from 12 to 20 amino acids, from 12 to 19 amino acids, from 12 to 18 amino acids, from 12 to 17 amino acids, from 12 to 16 amino acids, from 12 to 15 amino acids, from 12 to 14 amino acids, or 13 amino acids. In some embodiments, the TGF-β antagonist peptides contain between 12 and 16 amino acid residues organized in a linear fashion (e.g., absence of amino acid branching). These peptidic TGF-β antagonists can be, for instance, 12, 13, 14, 15 or 16 amino acid residues in length. Some of the peptidic TGF-β antagonists described herein are not shorter than 12 amino acid residues and are not longer than 16 amino acid residues. The peptidic TGF-β antagonists described herein can be provided as a composition comprising a single length of peptidic TGF-β antagonist (each having the same number in amino acids) or a plurality of lengths of peptidic TGF-β antagonists (comprising at least two different peptides each having a different number of amino acids).

The peptidic TGF-β antagonists described herein may comprise the ETWIWL motif (SEQ ID NO: 11) as well as additional amino acid residues (located either at the NH$_2$ and/or COOH terminus) to have a total of, instance, up to 28 amino acids, such as between 12 and 16 amino acid residues. In an embodiment, the peptidic TGF-β antagonists have a structure of the following formula (III):

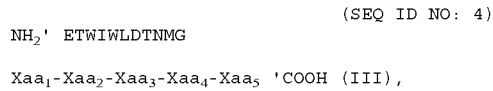

Xaa$_1$-Xaa$_2$-Xaa$_3$-Xaa$_4$-Xaa$_5$ 'COOH (III), wherein
Xaa$_1$ is any naturally-occurring amino acid;
Xaa$_2$ is absent or is any naturally-occurring amino acid;
Xaa$_3$ is absent or is any naturally-occurring amino acid, wherein Xaa$_3$ can only be present when Xaa$_2$ is present;

Xaa$_4$ is absent or is any naturally-occurring amino acid, wherein Xaa$_4$ can only be present only when Xaa$_3$ is present;
Xaa$_5$ is absent or is any naturally-occurring amino acid, wherein Xaa$_5$ can only be present only when Xaa$_4$ is present; and
"-" represents a peptide bond between two adjacent amino acid residues.

In some embodiments of the peptidic TGF-β antagonists of formula (III), Xaa$_2$ can be an arginine residue, Xaa$_3$ can be an isoleucine residue, Xaa$_4$ can be a tyrosine residue and/or Xaa$_5$ can be a glutamine residue. The TGF-β antagonist peptide having the structure of formula (III) are also presented in the generic amino acid sequence of SEQ ID NO: 16.

The peptidic TGF-β antagonists of formula (III) can include at least two amino acid residues bearing a net negative charge (when measuring at physiological pH). In some embodiments, the charge of the peptidic TGF-β antagonist is involved in binding to TGF-β. Such negatively-charged amino acid residues can interact, for example, with Arg25 and Arg94 of TGF-β3. These at least two net negative charge are present in the glutamate (E) and aspartate (D) residues of ETWIWLDTNMG (SEQ ID NO: 4).

In the peptidic TGF-β antagonists of formula (III), Xaa$_1$ can be any naturally-occurring amino acid. In an embodiment, Xaa$_1$ is an amino acid residue having a polar and uncharged side-chain or an amino acid residue having a hydrophobic side-chain. When Xaa$_1$ is an amino acid residue having a polar and uncharged side-chain, Xaa$_1$ can be, for example, a serine residue, a threonine residue, an asparagine residue or a glutamine residue. When Xaa$_1$ is an amino acid residue having an hydrophobic side-chain, Xaa$_1$ can be, for example, a tyrosine residue, an alanine residue, a valine residue, an isoleucine residue, a leucine residue, a methionine residue, a phenylalanine residue or a tryptophan residue. In some embodiments, Xaa$_1$ is a serine residue or a tyrosine residue. When Xaa$_1$ is present, Xaa$_2$, Xaa$_3$, Xaa$_4$ and Xaa$_5$ can be present or absent. In one embodiment, Xaa$_1$ is present and Xaa$_2$, Xaa$_3$, Xaa$_4$ and Xaa$_5$ are absent. In such embodiment, the TGF-β antagonist peptide can have the amino acid sequence of SEQ ID NO: 12.

In the TGF-β antagonist peptide of formula (III), Xaa$_2$ is an optional amino acid residue and can be any naturally-occurring amino acid. In some embodiments, Xaa$_2$ is an amino acid residue having a positively-charged side-chain. In an embodiment, Xaa$_2$ is an arginine residue, a histidine residue or a lysine residue. In yet another embodiment, Xaa$_2$ can be an arginine residue. When Xaa$_2$ is present, Xaa$_3$, Xaa$_4$ and Xaa$_5$ can be present or absent. In one embodiment, Xaa$_2$ is present and Xaa$_3$, Xaa$_4$ and Xaa$_5$ are absent. In such embodiment, the TGF-β antagonist peptide can have the amino acid sequence of SEQ ID NO: 13.

In the TGF-β antagonist peptide of formula (III), Xaa$_3$ is an optional amino acid residue and can be any naturally-occurring amino acid. Xaa$_3$ can only be present when Xaa$_2$ is present. In some embodiments, Xaa$_3$ is an amino acid residue having a hydrophobic side-chain. In an embodiment, Xaa$_3$ can be, for example, an alanine residue, a valine residue, an isoleucine residue, a methionine residue, a phenylalanine residue, a tyrosine residue, or a tryptophan residue. In an embodiment, Xaa$_3$ is an isoleucine residue. When Xaa$_3$ is present, Xaa$_4$ and Xaa$_5$ can be present or absent. In one embodiment, Xaa$_2$ and Xaa$_3$ are present and Xaa$_4$ and Xaa$_5$ are absent. In such embodiment, the TGF-β antagonist peptide can have the amino acid sequence of SEQ ID NO: 14.

In the TGF-β antagonist peptide of formula (III), Xaa₄ is an optional amino acid residue and can be any naturally-occurring amino acid. Xaa₄ can only be present when Xaa₂ and Xaa₃ are present. In some embodiments, Xaa₄ is an amino acid residue having a hydrophobic side-chain. In an embodiment, Xaa₄ can be, for example, an alanine residue, a valine residue, an isoleucine residue, a methionine residue, a phenylalanine residue, a tyrosine residue, or a tryptophan residue. In some embodiments, Xaa₄ is a tyrosine residue. When Xaa₂, Xaa₃ and Xaa₄ are present, Xaa₅ can be present or absent. In some embodiments, Xaa₄ is present and Xaa₅ are absent. In such embodiment, the TGF-β antagonist peptide can have the amino acid sequence of SEQ ID NO: 15.

In the TGF-β antagonist peptide of formula (III), Xaa₅ is an optional amino acid residue and can be any naturally-occurring amino acid. Xaa₅ can only be present when Xaa₂, Xaa₃ and Xaa₄ are present. In an embodiment, Xaa₅ is an amino acid residue having a polar and uncharged side-chain. Xaa₅ can be, for example, a serine residue, a threonine residue, an asparagine residue or a glutamine residue. In an embodiment, Xaa₅ is a glutamine residue. In one embodiment, the TGF-β antagonist peptide can have the amino acid sequence of SEQ ID NO: 5.

In some embodiments, the peptidic TGF-β antagonists have a structure of the following formula (II):

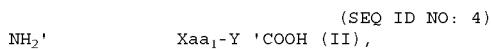

(SEQ ID NO: 4)
NH₂'   Xaa₁-Y 'COOH (II),

Wherein
Xaa₁ is any naturally-occurring amino acid;
Y is a peptide having between 0 and 4 amino acid residue; and
"-" represents a peptide bond between two adjacent amino acids.

In the peptidic TGF-β antagonists of formula (II), Y is a linear peptide having between 0 and 4 amino acid residues. When present, Y can be represented by the formula (IIa), (IIb), (IIc) or (IId).

In some of the embodiments of the peptidic TGF-β antagonists of formula (II), Xaa₁ can be as defined above for formula (III). When Y is absent (e.g., it has no (0) amino acid residues), Xaa₁ can be any naturally-occurring amino acid and in some embodiments, a serine residue. In the latter, the peptidic TGF-β antagonist consists of the amino acid sequence of SEQ ID NO: 12. When Y is present (e.g., it has between 1 and 4 amino acid residues) Xaa₁ can be any naturally-occurring amino acid and in some embodiments, a serine residue. In the latter, the peptidic TGF-β antagonist has the amino acid sequence of SEQ ID NO: 12.

In some embodiments of the peptidic TGF-β antagonists of formula (II), Y comprises a single amino acid residue. In such embodiment, Y can be of the formula (IIa)

-Xaa₂ (IIa)

wherein "-" represents a peptide bond between Xaa₁ and Xaa₂. In such embodiment, Xaa₂ can be any naturally-occurring amino acid or as defined above for formula (III). In some embodiments, Xaa₂ can be an arginine residue. In some embodiments, when Y has a single (1) amino acid residue and Xaa₂ is an arginine residue, the peptidic TGF-β antagonist consists of the amino acid sequence of SEQ ID NO: 13. In some embodiments, when Y has a more than one amino acid residues and Xaa₂ is an arginine residue, the peptidic TGF-β antagonist has the amino acid sequence of SEQ ID NO: 13.

In some embodiments of the peptidic TGF-β antagonists of formula (II), Y comprises two (2) amino acid residues. In such embodiment, Y can be of the formula (IIb):

-Xaa₂-Xaa₃ (IIb)

wherein "-" represents a peptide bond between two adjacent amino acid residues (Xaa₁ and Xaa₂ as well as Xaa₂ and Xaa₃). In such embodiment, Xaa₂ can be any naturally-occurring amino acid and, in some embodiments, Xaa₂ can be an arginine residue. In such embodiments, Xaa₃ can be any naturally-occurring amino acid (such as defined above for formula (III)) and, in some embodiments, Xaa₃ can be an isoleucine residue. In some embodiments, when Y has two (2) amino acid residues, Xaa₂ is an arginine residue and Xaa₃ is an isoleucine residue, the peptidic TGF-β antagonist consists of the amino acid sequence of SEQ ID NO: 14. In some embodiments, when Y has more than two (2) amino acid residues, Xaa₂ is an arginine residue and Xaa₃ is an isoleucine residue, the peptidic TGF-β antagonist comprises the amino acid sequence of SEQ ID NO: 14.

In some embodiments of the peptidic TGF-β antagonists of formula (II), Y comprises three (3) amino acid residues. In such embodiments, Y can of the formula (IIc):

-Xaa₂-Xaa₃-Xaa₄ (IIc)

wherein "-" represents a peptide bond between two adjacent amino acid residues (between Xaa₁ and Xaa₂, between Xaa₂ and Xaa₃ as well as between Xaa₃ and Xaa₄). In such embodiment, Xaa₂ can be any naturally-occurring amino acid and, in some embodiments, Xaa₂ can be an arginine residue. In such embodiments, Xaa₃ can be any naturally-occurring amino acid and, in some embodiments, Xaa₃ can be an isoleucine residue. In such embodiments, Xaa₄ can be any naturally-occurring amino acid (as provided in the definition above for formula (III)) and, in some embodiments, Xaa₄ can be a tyrosine residue. In some embodiments, when Y has three (3) amino acid residues, Xaa₂ is an arginine residue, Xaa₃ is an isoleucine residue and Xaa₄ is a tyrosine residue, the peptidic TGF-β antagonist consists of the amino acid sequence of SEQ ID NO: 15. In some embodiments, when Y has more than three (3) amino acid residues, Xaa₂ is an arginine residue, Xaa₃ is an isoleucine residue and Xaa₄ is a tyrosine residue, the peptidic TGF-β antagonist has the amino acid sequence of SEQ ID NO: 15.

In some embodiments of the peptidic TGF-β antagonists of formula (II), Y comprises four (4) amino acid residues. In such embodiment, Y can be of the formula (IId):

-Xaa₂-Xaa₃-Xaa₄-Xaa₅ (IId)

wherein "-" represents a peptide bond between two adjacent amino acid residues (between Xaa₁ and Xaa₂, between Xaa₂ and Xaa₃, between Xaa₃ and Xaa₄ as well as between Xaa₄ and Xaa₅). In such embodiment, Xaa₂ can be any naturally-occurring amino acid and, in some embodiments, Xaa₂ can be an arginine residue. In such embodiments, Xaa₃ can be any naturally-occurring amino acid and, in some embodiments, Xaa₃ can be an isoleucine residue. In such embodiments, Xaa₄ can be any naturally-occurring amino acid and, in some embodiments, Xaa₄ can be a tyrosine residue. In such embodiments, Xaa₅ can be any naturally-occurring amino acid (as provided above for formula (III)) and, in some embodiments, Xaa₅ can be a glutamine residue. In some embodiments, when Y has four (4) amino acid residues, Xaa₂ is an arginine residue, Xaa₃ is an isoleucine residue, Xaa₄ is a tyrosine residue and Xaa₅ is a glutamine residue, the peptidic TGF-β antagonist consists of the amino acid sequence of SEQ ID NO: 5.

In some of the TGF-β antagonists described herewith, the amino acid sequence of SEQ ID NO: 4 (found in formulae (II) and (III)) can be replaced by the following amino acid sequence (herein referred to as the peptides having the amino acid sequence of SEQ ID NO: 1 or variants of SEQ ID NO: 4):

(SEQ ID NO: 21)
Xaa₁-Xaa₂-Xaa₃-Xaa₄-Xaa₅-Xaa₆-Xaa₇-Xaa₈-Xaa₉-Xaa₁₀-

Xaa₁₁ wherein "-" represents a peptide bond between two adjacent amino acid residues (between $Xaa_1$ and $Xaa_2$, between $Xaa_2$ and $Xaa_3$, between $Xaa_3$ and $Xaa_4$, between $Xaa_4$ and $Xaa_5$, between $Xaa_5$ and $Xaa_6$, between $Xaa_6$ and $Xaa_7$, between $Xaa_7$ and $Xaa_8$, between $Xaa_8$ and $Xaa_9$ as well as between $Xaa_9$ and $Xaa_{10}$). $Xaa_1$ can be any amino acid having a negatively-charged side-chain (aspartic acid or glutamic acid for example) and, in some embodiments, $Xaa_1$ can be a glutamic acid residue. $Xaa_2$ can be any amino acid having a polar uncharged side-chain (serine, threonine, asparagine or glutamine for example) and, in some embodiments, $Xaa_2$ can be a threonine residue. $Xaa_3$ can be any amino acid having a hydrophobic side-chain (alanine, isoleucine, leucine, methionine, phenylalanine, tyrosine or tryptophan for example) and, in some embodiments, $Xaa_3$ can be a tryptophan residue. $Xaa_4$ can be any amino acid having a hydrophobic side-chain (alanine, isoleucine, leucine, methionine, phenylalanine, tyrosine or tryptophan for example) and, in some embodiments, $Xaa_4$ can be an isoleucine residue. $Xaa_5$ can be any amino acid having a hydrophobic side-chain (alanine, isoleucine, leucine, methionine, phenylalanine, tyrosine or tryptophan for example) and, in some embodiments, $Xaa_5$ can be a tryptophan residue. $Xaa_6$ can be any amino acid having a hydrophobic side-chain (alanine, isoleucine, leucine, methionine, phenylalanine, tyrosine or tryptophan for example) and, in some embodiments, $Xaa_6$ can be a leucine residue. $Xaa_7$ can be any amino acid having a negatively-charged side-chain (aspartic acid or glutamic acid for example) and, in some embodiments, $Xaa_7$ can be an aspartic acid residue. $Xaa_8$ can be any amino acid having a polar uncharged side-chain (serine, threonine, asparagine or glutamine for example) and, in some embodiments, $Xaa_8$ can be a threonine residue. $Xaa_9$ can be any amino acid having a polar uncharged side-chain (serine, threonine, asparagine or glutamine for example) and, in some embodiments, $Xaa_9$ can be an asparagine residue. $Xaa_{10}$ can be any amino acid having a hydrophobic side-chain (alanine, isoleucine, leucine, methionine, phenylalanine, tyrosine or tryptophan for example) and, in some embodiments, $Xaa_{10}$ can be a methionine residue. $Xaa_{11}$ can be any amino acid having a neutral non-polar side-chain (alanine, valine or glycine for example) and, in some embodiments, $Xaa_{10}$ can be a glycine residue.

Table A provides various embodiments of the contemplated TGF-β antagonist peptides of formulae (II) and (Ill).

TABLE A

The TGF-β antagonist peptides described herein can possess the common structure shown in formula (III). Some of the contemplated combinations of the $Xaa_1$, $Xaa_2$, $Xaa_3$, $Xaa_4$ and $Xaa_5$ residues are shown below. Amino acid residues are identified using three-letter code. Xaa refers to any naturally-occurring amino acid residue.

| Peptide | $Xaa_1$ | $Xaa_2$ | $Xaa_3$ | $Xaa_4$ | $Xaa_5$ |
|---|---|---|---|---|---|
| 12-A | Xaa | Absent | Absent | Absent | Absent |
| 12-B | Ser | Absent | Absent | Absent | Absent |
| 13-A | Xaa | Xaa | Absent | Absent | Absent |
| 13-B | Ser | Xaa | Absent | Absent | Absent |
| 13-C | Xaa | Arg | Absent | Absent | Absent |
| 13-D | Ser | Arg | Absent | Absent | Absent |
| 14-A | Xaa | Xaa | Xaa | Absent | Absent |
| 14-B | Ser | Xaa | Xaa | Absent | Absent |
| 14-C | Xaa | Arg | Xaa | Absent | Absent |
| 14-D | Xaa | Xaa | Ile | Absent | Absent |
| 14-E | Ser | Arg | Xaa | Absent | Absent |
| 14-F | Ser | Xaa | Ile | Absent | Absent |
| 14-G | Xaa | Arg | Ile | Absent | Absent |
| 14-H | Ser | Arg | Ile | Absent | Absent |
| 15-A | Xaa | Xaa | Xaa | Xaa | Absent |
| 15-B | Xaa | Xaa | Xaa | Tyr | Absent |
| 15-C | Ser | Xaa | Xaa | Xaa | Absent |
| 15-D | Ser | Xaa | Xaa | Tyr | Absent |
| 15-E | Xaa | Arg | Xaa | Xaa | Absent |
| 15-F | Xaa | Arg | Xaa | Tyr | Absent |
| 15-G | Xaa | Xaa | Ile | Xaa | Absent |
| 15-H | Xaa | Xaa | Ile | Tyr | Absent |
| 15-I | Ser | Arg | Xaa | Xaa | Absent |
| 15-J | Ser | Arg | Xaa | Tyr | Absent |
| 15-K | Ser | Xaa | Ile | Xaa | Absent |
| 15-L | Ser | Xaa | Ile | Tyr | Absent |
| 15-M | Xaa | Arg | Ile | Xaa | Absent |
| 15-N | Xaa | Arg | Ile | Tyr | Absent |
| 15-O | Ser | Arg | Ile | Xaa | Absent |
| 15-P | Ser | Arg | Ile | Tyr | Absent |
| 16-A | Xaa | Xaa | Xaa | Xaa | Xaa |
| 16-B | Xaa | Xaa | Xaa | Xaa | Gln |
| 16-C | Xaa | Xaa | Xaa | Tyr | Xaa |
| 16-D | Xaa | Xaa | Xaa | Tyr | Gln |
| 16-E | Ser | Xaa | Xaa | Xaa | Xaa |
| 16-F | Ser | Xaa | Xaa | Xaa | Gln |
| 16-G | Ser | Xaa | Xaa | Tyr | Xaa |
| 16-H | Ser | Xaa | Xaa | Tyr | Gln |
| 16-I | Xaa | Arg | Xaa | Xaa | Xaa |
| 16-J | Xaa | Arg | Xaa | Xaa | Gln |
| 16-K | Xaa | Arg | Xaa | Tyr | Xaa |
| 16-L | Xaa | Arg | Xaa | Tyr | Gln |
| 16-M | Xaa | Xaa | Ile | Xaa | Xaa |
| 16-N | Xaa | Xaa | Ile | Xaa | Gln |
| 16-O | Xaa | Xaa | Ile | Tyr | Xaa |
| 16-P | Xaa | Xaa | Ile | Tyr | Gln |
| 16-Q | Ser | Arg | Xaa | Xaa | Xaa |
| 16-R | Ser | Arg | Xaa | Xaa | Gln |
| 16-S | Ser | Arg | Xaa | Tyr | Xaa |
| 16-T | Ser | Arg | Xaa | Tyr | Gln |
| 16-U | Ser | Xaa | Ile | Xaa | Xaa |
| 16-V | Ser | Xaa | Ile | Xaa | Gln |
| 16-W | Ser | Xaa | Ile | Tyr | Xaa |
| 16-X | Ser | Xaa | Ile | Tyr | Gln |
| 16-Y | Xaa | Arg | Ile | Xaa | Xaa |
| 16-Z | Xaa | Arg | Ile | Xaa | Gln |
| 16-AA | Xaa | Arg | Ile | Tyr | Xaa |
| 16-BB | Xaa | Arg | Ile | Tyr | Gln |
| 16-CC | Ser | Arg | Ile | Xaa | Xaa |
| 16-DD | Ser | Arg | Ile | Xaa | Gln |
| 16-EE | Ser | Arg | Ile | Tyr | Xaa |
| 16-FF | Ser | Arg | Ile | Tyr | Gln |

The peptidic TGF-β antagonists can be provided as a composition. The composition can comprises a single type of peptidic TGF-β antagonists having the same amino acid sequence or a plurality of types of peptidic TGF-β antagonists in which at least two peptides having different amino acid sequences.

The present disclosure also provides peptidic TGF-β antagonists variants, such as cyclic and multimeric variants, for instance, as described below. Exemplary peptides for use with the compositions and methods described herein are summarized in Table B, below. Peptides that can be used with the compositions and methods described herein include those listed in Table B, as well as those having at least 85% sequence identity (e.g., at least 85%, 90%, 95%, 97%, 99%, or greater) relative to each of the listed peptides in Table B.

TABLE B

Summary of select peptides described herein:

| Peptide Name | Amino Acid Sequence |
| --- | --- |
| P11 | ETWIWLDTNMG (SEQ ID NO: 4) |
| P12 | ETWIWLDTNMGS (SEQ ID NO: 12) |
| P13 | ETWIWLDTNMGSR (SEQ ID NO: 13) |
| P14 | ETWIWLDTNMGSRI (SEQ ID NO: 14) |
| P15 | ETWIWLDTNMGSRIY (SEQ ID NO: 15) |
| P16 | ETWIWLDTNMGSRIYQ (SEQ ID NO: 5) |
| P17 | ETWIWLDTNMGSRIYQE (SEQ ID NO: 22) |
| P18 | ETWIWLDTNMGSRIYQEF (SEQ ID NO: 23) |
| P19 | ETWIWLDTNMGSRIYQEFE (SEQ ID NO: 24) |
| P20 | ETWIWLDTNMGSRIYQEFEV (SEQ ID NO: 25) |
| P21 | ETWIWLDTNMGSRIYQEFEVT (SEQ ID NO: 6) |
| P28 | ETWIWLDTNMGSRIYQEFEVTVVPDSITS (SEQ ID NO: 2) |

Peptide Synthesis Techniques

Systems and processes for performing solid phase peptide synthesis are known in the art and have been described, for instance, in U.S. Pat. Nos. 9,169,287; 9,388,212; 9,206,222; 6,028,172; and 5,233,044, among others, the disclosures of each of which are incorporated herein by reference as they pertain to protocols and techniques for the synthesis of peptides on solid support. Solid phase peptide synthesis is a known process in which amino acid residues are added to peptides that have been immobilized on a solid support, such as a polymeric resin (e.g., a hydrophilic resin, such as a polyethylene-glycol-containing resin, or hydrophobic resin, such as a polystyrene-based resin).

Peptides, such as those containing protecting groups at amino, hydroxy, thiol, and carboxy substituents, among others, may be bound to a solid support such that the peptide is effectively immobilized on the solid support. For example, the peptides may be bound to the solid support via their C termini, thereby immobilizing the peptides for subsequent reaction in at a resin-liquid interface.

The process of adding amino acid residues to immobilized peptides can include exposing a deprotection reagent to the immobilized peptides to remove at least a portion of the protection groups from at least a portion of the immobilized peptides. The deprotection reagent exposure step can be configured, e.g., such that side-chain protection groups are preserved, while N-termini protection groups are removed. For instance, an exemplary amino protecting may contain fluorenylmethyloxycarbonyl (Fmoc). A deprotection reagent containing piperidine (e.g., a piperidine solution in an appropriate organic solvent, such as dimethyl formamide (DMF)) may be exposed to the immobilized peptides such that the Fmoc protecting groups are removed from at least a portion of the immobilized peptides. Other protecting groups suitable for the protection of amino substituents include, for instance, the tert-butyloxycarbonyl (Boc) moiety. A deprotection reagent comprising a strong acid, such as trifluoroacetic acid (TFA) may be exposed to immobilized peptides containing a Boc-protected amino substituent so as to remove the Boc protecting group by an ionization process. In this way, peptides can be protected and deprotected at specific sites, such as at one or more side-chains or at the N- or C-terminus of an immobilized peptide so as to append chemical functionality regioselectively at one or more of these positions. This can be used, for instance, to derivatize a side-chain of an immobilized peptide, or to synthesize a peptide, e.g., from the C-terminus to the N-terminus.

The process of adding amino acid residues to immobilized peptides can include, for instance, exposing protected, activated amino acids to the immobilized peptides such that at least a portion of the activated amino acids are bonded to the immobilized peptides to form newly-bonded amino acid residues. For example, the peptides may be exposed to activated amino acids that react with the deprotected N-termini of the peptides so as to elongate the peptide chain by one amino acid. Amino acids can be activated for reaction with the deprotected peptides by reaction of the amino acid with an agent that enhances the electrophilicity of the carbonyl carbon of the amino acid. For example, phosphonium and uronium salts can, in the presence of a tertiary base (e.g., diisopropylethylamine (DIPEA) and triethylamine (TEA), among others), convert protected amino acids into activated species (for example, BOP, PyBOP, HBTU, and TBTU all generate HOBt esters). Other reagents can be used to help prevent racemization that may be induced in the presence of a base. These reagents include carbodiimides (for example, DCC or WSCDI) with an added auxiliary nucleophile (for example, 1-hydroxy-benzotriazole (HOBt), 1-hydroxy-azabenzotriazole (HOAt), or HOSu) or derivatives thereof. Another reagent that can be utilized to prevent racemization is TBTU. The mixed anhydride method, using isobutyl chloroformate, with or without an added auxiliary nucleophile, can also be used, as well as the azide method, due to the low racemization associated with this reagent. These types of compounds can also increase the rate of carbodiimide-mediated couplings, as well as prevent dehydration of Asn and Gln residues. Typical additional reagents include also bases such as N,N-diisopropylethylamine (DIPEA), triethylamine (TEA) or N-methylmorpholine (NMM). These reagents are described in detail, for instance, in U.S. Pat. No. 8,546,350, the disclosure of which is incorporated herein in its entirety.

Cyclic peptides can be synthesized using solid-phase peptide synthesis techniques. For instance, a side-chain substituent, such as an amino, carboxy, hydroxy, or thiol moiety can be covalently bound to a resin, leaving the N-terminus and C-terminus of the amino acid exposed in solution. The N- or C-terminus can be chemically protected, for instance, while reactions are carried out that elongate the peptide chain. The termini of the peptide can then be selectively deprotected and coupled to one another while the peptide is immobilized by way of the side-chain linkage to the resin. Techniques and reagents for the synthesis of head-to-tail cyclic peptides are known in the art and are described, for instance, in U.S. Pat. Nos. 9,388,212 and 7,589,170, the disclosures of which are incorporated herein by reference in their entirety.

Cyclic and Dimeric Variants of TGF-β Antagonist Peptides

In some embodiments, a TGF-β-binding peptide described herein is a linear peptide, for instance, containing amine and carboxyl substituents at the N- and C-termini of the peptide, respectively, or containing acyl (e.g., acetyl) and carboxamide substituents at the N- and C-termini of the peptide, respectively. In some embodiments, the TGF-β-binding peptide is a cyclic peptide. For instance, the TGF-β-binding peptide may be covalently bound to a cysteine residue at each of the N-terminus and the C-terminus of the TGF-β-binding peptide. The cysteine residues can be covalently bound to one another, for example, by a disulfide bond. In some embodiments, the cysteine residues are covalently bound to one another by way of a linker, for instance, through thioether bonds. In some embodiments, the linker contains an alkyl, aryl, heteroaryl, cycloalkyl, or heterocyclolalkyl moiety. In some embodiments, the TGF-β-binding peptide is a head-to-tail cyclic peptide.

In some embodiments, the peptidic TGF-β antagonists or their variants can be provided as multimers, such as dimers (e.g., in a dimeric form). For example, in some embodiments, the peptidic TGF-β antagonist can be modified to bear (e.g., either at their N- or C-terminus) one or more amino acids (such as one or more lysine residues for example) that can be linked with a spacer to form a dimer. In a further embodiment, the dimeric peptidic TGF-β antagonist comprises two identical TGF-β antagonist having the same amino acid sequence. In such embodiment, the each of the peptidic TGF-β antagonist can be covalently associated by a linker. The section that follows provides a description of chemical bond-forming techniques and linkers that can be used for synthesizing dimeric and cyclic TGF-β antagonist peptides.

Linkers for Peptide Cyclization and Dimerization

A variety of linkers can be used to covalently couple reactive residues within peptidic TGF-β antagonist to one another, for instance, so as to form cyclic or dimeric peptide products. Exemplary linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for chemical coupling). Examples of linkers useful for the synthesis of cyclic TGF-β antagonist peptides and dimeric TGF-β antagonist peptides include those that contain electrophiles, such as Michael acceptors (e.g., maleimides), activated esters, electron-deficient carbonyl compounds, and aldehydes, among others, suitable for reaction with nucleophilic substituents present within antibodies, antigen-binding fragments, and ligands, such as amine and thiol moieties. For instance, linkers suitable for the synthesis of cyclic TGF-β antagonist peptides and dimeric TGF-β antagonist peptides include, without limitation, alkyl, cycloalkyl, and heterocycloalkyl linkers, such as open-chain ethyl, propyl, butyl, hexyl, heptyl, octyl, nonyl, or decyl chains, cyclohexyl groups, cyclopentyl groups, cyclobutyl groups, cyclopropyl groups, piperidinyl groups, morpholino groups, or others containing two reactive moieties (e.g., halogen atoms, aldehyde groups, ester groups, acyl chloride groups, acyl anhydride groups, tosyl groups, mesyl groups, or brosyl groups, among others, that can be displaced by reactive nucleophilic atoms present within a TGF-β antagonist peptide), aryl or heteroaryl linkers, such as benzyl, napthyl, or pyridyl groups containing two halomethyl groups that can be displaced by reactive nucleophilic atoms present within a TGF-β antagonist peptide. Exemplary linkers include succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, for instance, Liu et al., 18:690-697, 1979, the disclosure of which is incorporated herein by reference as it pertains to linkers for chemical conjugation. Additional linkers include the non-cleavable maleimidocaproyl linkers, which are described by Doronina et al., Bioconjugate Chem. 17:14-24, 2006, the disclosure of which is incorporated herein by reference as it pertains to linkers for chemical conjugation.

Pharmaceutical Compositions and Routes of Administration

The peptidic TGF-β antagonists described herein, as well as their variants, can be formulated as a pharmaceutical composition. In the pharmaceutical compositions described herein, the peptidic TGF-β antagonists and/or their variants can be formulated to include a pharmaceutically acceptable carrier or vehicle. The peptidic TGF-β antagonists, dimers and/or their variants may be formulated prior to administration to the mammal using available techniques and procedures. The peptidic TGF-β antagonists and/or their variants as well as their corresponding pharmaceutical compositions can be formulated for administration to the skin of the mammal, including the skin of the human. In the context of the present disclosure, the expression "administration to the skin" includes, but is not limited to topical skin administration, subcutaneous (sc) injection or intra-dermal injection. Exemplary formulations suitable for topical skin administration include, but are not limited to, lotions, creams, pastes, gels as well as solids. Topical skin formulations can be administered using a dressing (such as, for example, an impregnated wound dressing), can be applied directly to the skin area to be treated, can be administered transdermally using a patch, surgical suture, or surgical staple. Such compositions include, for example, lotions, creams, solutions, gels and solids. In some embodiments, suitable carriers for topical administration typically remain in place on the skin as a continuous film and resist being removed by perspiration or immersion in water. The carrier can be organic in nature and capable of having dispersed or dissolved therein the antagonists. The carrier may include pharmaceutically acceptable emollients, emulsifiers, thickening agents, solvents and the like. In some embodiments, the peptidic TGF-β antagonists are formulation as a biodegradable sustained-release composition for cutaneous, subcutaneous or intramuscular administration.

In some embodiments, peptidic TGF-β antagonists, dimers, and/or their variants as well as their corresponding pharmaceutical compositions can be formulated for administration in the vicinity of or inside a cancerous tumor. In the context of the present disclosure, the expression "administration in the vicinity of or inside a cancerous tumor" includes, but is not limited to intra-tumoral administration as well as systemic administration (intravenous, oral, intraarterial, perenteral (including subcutaneous, intra-muscular and intravenous), intracranial, intraorbital, ophthalmic, intraventricular, intracapsular, intraspinal, intrathecal, epidural, intracisternal, intraperitoneal, rectal, buccal (including sublingual), pulmonary and intranasal). Exemplary formulations suitable for administration in the vicinity of or inside a cancerous tumor include, but are not limited to, solutions, suspensions and the like.

Therapeutic Uses of the Peptidic TGF-β Antagonists

As shown herein, the peptidic TGF-β antagonists can be used to prevent, limit or, in some instances, treat a pathological condition associated with a pathological increase in TGF-β activity. As used in the context of the present disclosure, a "pathological increase in TGF-β activity" refers to an increase in a subject's level or activity of TGF-β (which can be systemic or local) leading to unwanted biological effects. In some embodiments, a pathological increase in TGF-β activity causes or sustains "a pathological fibrotic condition", e.g., a condition in which excessive and pathological fibrosis occurs. "Fibrosis" refers in general to the formation of excess fibrous connective tissue in an organ or tissue in a reparative or reactive process. "Pathological fibrosis" refers to a fibrotic condition in which the excess fibrous tissue will not resorb to a normal healthy state. In the context of the present disclosure, pathological fibrotic conditions include, but are not limited to, skin fibrotic conditions (e.g., hypertrophic scarring, keloids, delayed scarring, etc.) and auto-immune diseases (e.g., scleroderma, psoriasis). In some embodiments, a pathological increase in TGF-β activity causes or sustains cancer maintenance and/or progression by allowing or facilitating cancerous cellular migration (cancer metastasis).

The expression: "prevention, treatment and alleviation of symptoms refer to the ability of the antagonists to limit the development, progression and/or symptomology of the pathological conditions described herein. When a skin fibrotic condition or an auto-immune disease is the pathological condition, the prevention, treatment and/or alleviation of symptoms can encompass the reduction of proliferation of cells (e.g., fibroblasts), the reduction in extracellular matrix production, the reduction in inflammation, and/or the increase in matrix degradation.

When cancer is the pathological condition, the prevention, treatment and/or alleviation of symptoms can encompass the reduction of epithelial-mesenchymal transition of the cells, the reduction in the migration of the cells (which can include, in an embodiment, the reduction in the metastasis of the cells (number, size and/or location of the metastasis) and/or the reduction in the proliferation of the cells (e.g. by reducing the total number of cells in an hyperproliferative state and/or by reducing the pace of proliferation of cells). Symptoms associated with cancer include, but are not limited to: local symptoms which are associated with the site of the primary cancer (such as lumps or swelling (tumor), hemorrhage, ulceration and pain), metastatic symptoms which are associated to the spread of cancer to other locations in the body (such as enlarged lymph nodes, hepatomegaly, splenomegaly, pain, fracture of affected bones, and neurological symptoms) and systemic symptoms (such as weight loss, fatigue, excessive sweating, anemia and paraneoplastic phenomena). The peptidic TGF-β antagonists and/or their corresponding variants can be used to limit, reduce or inhibit epithelial-mesenchymal transition of cancer cells, invasion of cancer cells outside their tissue of origin, motility of cancer cells, limit/reduce the number and proliferation of cancer stem cells, the expression of fibronectin, and the expression of Slug and/or the migration of cancer cells.

Hypertrophic scarring is a pervasive medical problem which often occurs as a result of burn, trauma, or surgical injury. Hypertrophic scarring is characterized by the formation of rigid scar tissue often resulting in significant functional impairment, leading to joint contractures, deformities, and central nervous system dysfunction. Keloid scars are thick, raised, itchy clusters of scar tissue that grow beyond the edges of a wound; they are more frequent in dark-skinned individuals and tend to recur. Hypertrophic scars are raised, red, thick scars that remains within the boundary of the injury. Keloid and hypertrophic scars result from local skin trauma or inflammatory skin disorders like lacerations, burns, skin piercing, surgery, etc.

Scleroderma (also referred to as systemic sclerosis) is a connective tissue disorder characterized by excessive extracellular matrix (ECM) synthesis and deposition in the skin and internal organs, leading to organ dysfunction and failure. Other features of SSc include autoimmunity and inflammation, widespread vasculopathy (blood vessel damage) affecting multiple vascular beds and progressive interstitial and perivascular fibrosis. Depending on its location and extent, localized scleroderma may cause severe cosmetic problems as well as restricted joint motion secondary to contractures.

Psoriasis is a common, chronic, relapsing/remitting, immune-mediated systemic disease characterized by skin lesions including red, scaly patches, papules, and plaques, which usually itch. The skin lesions seen in psoriasis may vary in severity from minor localized patches to complete body coverage. Psoriasis is also linked to cardiovascular diseases.

Cancer, also referred to as a malignant neoplasm, is a group of diseases involving abnormal cell growth with the potential to invade or spread to other parts of the body. In the context of the present disclosure, the term "cancer" includes, but is not limited to, carcinoma, sarcoma, lymphoma, leukemia, germ cell tumor and blastoma.

The peptidic TGF-β antagonists and their corresponding variants are intended to be administered in a "therapeutically effective amount". The expression "therapeutically effective amount" refers to the amount of peptidic TGF-β antagonists and/or their corresponding variants, when administered to a mammalian subject for treating or preventing the particular disorders, diseases or conditions described above, is sufficient to effect such treatment or prevention of those disorders, diseases or conditions. Dosages and therapeutically effective amounts may vary for example, depending upon a variety of factors including the activity of the specific antagonist employed, the age, body weight, general health, gender, and diet of the mammalian subject, the time of administration, the route of administration, the rate of excretion, and any drug combination, if applicable, the effect which the practitioner desires the compound to have upon the subject and the properties of the compounds (e.g. bioavailability, stability, potency, toxicity, etc.), and the particular disorder(s) the mammalian subject is suffering from. In addition, the therapeutically effective amount may depend on the mammalian subject's skin condition (e.g. lightly or severely burned, presence of other skin injuries, etc.), the mammalian's cancer stage (e.g., I, II, III and IV), the severity of the disease state, or underlying disease or complications.

The therapeutic uses and methods described herein can also include co-formulation and/or co-administration of at least one antagonists together with another therapeutically effective agent for the prevention and/or treatment of a pathological fibrotic disease or cancer. These other therapeutically effective agents can be administered prior to, at the same time or after the antagonists are administered to the mammalian subject. Examples of such therapeutic agents used for the treatment of pathological fibrosis include, but are not limited to, vitamin D analogs, interferon α and γ, methotrexate, penicillin, corticosteroids, immune suppressants, cyclosporine, anti-TNF antibodies, anti-infectives such as silver and iodine composition, ibuprofen and antibiotics. Examples of therapeutic agents used for the treatment of cancer include, but are not limited to, chemotherapeutic agents, radiation therapy, signaling pathway inhibitors, kinase inhibitors, gene expression blockers and modifiers.

The therapeutic uses and methods described can be used before or after surgery (e.g., removal of a scar or tumor). The therapeutic uses and methods described can be used in conjunction with radiotherapy.

The administration of the peptidic TGF-β antagonists and/or their variants can be conducted in a single unit dosage form with continuous therapy, in a single dose therapy ad libitum or as multiple doses.

Methods for the Delivery of Exogenous Nucleic Acids to Cells

Transfection Techniques

Techniques that can be used to introduce a polynucleotide, such as nucleic acid encoding a TGF-β antagonist peptide describe herein, into a cell (e.g., a mammalian cell, such as a human cell) are well known in the art. Exemplary cells include, for instance, cells of a skin graft (such as fibroblasts, keratinocytes, Merkel cells, melanocytes, or Langerhans cells). By inducing expression of a TGF-β antagonist protein described herein in one or more cells of a skin graft, the graft may be administered to a patient, such as a patient suffering from a fibrotic skin condition, cancer, or burn described herein, so as to attenuate TGF-β expression and alleviate the disease or condition (or one or more symptoms associated with the disease or condition).

For instance, electroporation can be used to permeabilize mammalian cells (e.g., human cells) by the application of an electrostatic potential to the cell of interest. Mammalian cells, such as human cells, subjected to an external electric field in this manner are subsequently predisposed to the uptake of exogenous nucleic acids. Electroporation of mammalian cells is described in detail, e.g., in Chu et al., Nucleic Acids Research 15:1311 (1987), the disclosure of which is incorporated herein by reference. A similar technique, Nucleofection™, utilizes an applied electric field in order to stimulate the uptake of exogenous polynucleotides into the nucleus of a eukaryotic cell. Nucleofection™ and protocols useful for performing this technique are described in detail, e.g., in Distler et al., Experimental Dermatology 14:315 (2005), as well as in US 2010/0317114, the disclosures of each of which are incorporated herein by reference.

Additional techniques useful for the transfection of cells of interest include the squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a human cell. Squeeze-poration is described in detail, e.g., in Sharei et al., Journal of Visualized Experiments 81:e50980 (2013), the disclosure of which is incorporated herein by reference.

Lipofection represents another technique useful for transfection of cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, for instance, by direct fusion of the liposome with the cell membrane or by endocytosis of the complex. Lipofection is described in detail, for instance, in U.S. Pat. No. 7,442,386, the disclosure of which is incorporated herein by reference. Similar techniques that exploit ionic interactions with the cell membrane to provoke the uptake of foreign nucleic acids include contacting a cell with a cationic polymer-nucleic acid complex. Exemplary cationic molecules that associate with polynucleotides so as to impart a positive charge favorable for interaction with the cell membrane include activated dendrimers (described, e.g., in Dennig, Topics in Current Chemistry 228:227 (2003), the disclosure of which is incorporated herein by reference) and diethylaminoethyl (DEAE)-dextran, the use of which as a transfection agent is described in detail, for instance, in Gulick et al., Current Protocols in Molecular Biology 40:1:9.2:9.2.1 (1997), the disclosure of which is incorporated herein by reference. Magnetic beads are another tool that can be used to transfect cells in a mild and efficient manner, as this methodology utilizes an applied magnetic field in order to direct the uptake of nucleic acids. This technology is described in detail, for instance, in US 2010/0227406, the disclosure of which is incorporated herein by reference.

Another useful tool for inducing the uptake of exogenous nucleic acids by cells is laserfection, a technique that involves exposing a cell to electromagnetic radiation of a particular wavelength in order to gently permeabilize the cells and allow polynucleotides to penetrate the cell membrane. This technique is described in detail, e.g., in Rhodes et al., Methods in Cell Biology 82:309 (2007), the disclosure of which is incorporated herein by reference.

Microvesicles represent another potential vehicle that can be used to modify the genome of a cell according to the methods described herein. For instance, microvesicles that have been induced by the co-overexpression of the glycoprotein VSV-G with, e.g., a genome-modifying protein, such as a nuclease, can be used to efficiently deliver proteins into a cell that subsequently catalyze the site-specific cleavage of an endogenous polynucleotide sequence so as to prepare the genome of the cell for the covalent incorporation of a polynucleotide of interest, such as a gene or regulatory sequence. The use of such vesicles, also referred to as Gesicles, for the genetic modification of eukaryotic cells is described in detail, e.g., in Quinn et al., Genetic Modification of Target Cells by Direct Delivery of Active Protein [abstract]. In: Methylation changes in early embryonic genes in cancer [abstract], in: Proceedings of the 18th Annual Meeting of the American Society of Gene and Cell Therapy; 2015 May 13, Abstract No. 122.

Incorporation of Genes by Gene Editing Techniques

In addition to the above, a variety of tools have been developed that can be used for the incorporation of exogenous genes, e.g., exogenous genes encoding a TGF-β antagonist peptide described herein, into cells, such as a human cell (e.g., fibroblasts, keratinocytes, Merkel cells, melanocytes, or Langerhans cells of a human skin graft). One such method that can be used for incorporating polynucleotides encoding a TGF-β antagonist described herein into cells involves the use of transposons. Transposons are polynucleotides that encode transposase enzymes and contain a polynucleotide sequence or gene of interest flanked by 5' and 3' excision sites. Once a transposon has been delivered into a cell, expression of the transposase gene commences and results in active enzymes that cleave the gene of interest from the transposon. This activity is mediated by the site-specific recognition of transposon excision sites by the transposase. In some instances, these excision sites may be terminal repeats or inverted terminal repeats. Once excised from the transposon, the gene encoding a TGF-β antagonist peptide can be integrated into the genome of a mammalian cell by transposase-catalyzed cleavage of similar excision sites that exist within the nuclear genome of the cell. This allows the gene of interest to be inserted into the cleaved nuclear DNA at the complementary excision sites, and subsequent covalent ligation of the phosphodiester bonds that join the gene encoding the TGF-β antagonist peptide to the DNA of the mammalian cell genome (e.g., fibroblast, keratinocyte, Merkel cell, melanocyte, or Langerhans cell genome) completes the incorporation process. In some cases, the transposon may be a retrotransposon, such that the gene encoding the TGF-β antagonist peptide is first transcribed to an RNA product and then reverse-transcribed to DNA before incorporation in the mammalian cell genome. Exemplary transposon systems include the piggybac transposon (described in detail in, e.g., WO 2010/085699) and the sleeping beauty transposon (described in detail in, e.g., US 2005/0112764), the disclosures of each of which are incorporated herein by reference as they pertain to transposons for use in gene delivery to a cell of interest, such as a fibroblast, keratinocyte, Merkel cell, melanocyte, or Langerhans cell.

Another tool for the integration of genes encoding TGF-β antagonist peptides into the genome of a cell, such as a fibroblast, keratinocyte, Merkel cell, melanocyte, or Langerhans cell, is the clustered regularly interspaced short palindromic repeats (CRISPR)/Cas system, a system that originally evolved as an adaptive defense mechanism in bacteria and archaea against viral infection. The CRISPR/Cas system includes palindromic repeat sequences within plasmid DNA and an associated Cas9 nuclease. This ensemble of DNA and protein directs site specific DNA cleavage of a sequence of interest by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a particular sequence and localize the Cas9 nuclease to this site. In this manner, highly site-specific cas9-mediated DNA cleavage can be engendered in a foreign polynucleotide because the interaction that brings cas9 within close proximity of the DNA molecule of interest is governed by RNA:DNA hybridization. As a result, one can theoretically design a CRISPR/Cas system to cleave any DNA molecule of interest. This technique has been exploited in order to edit eukaryotic genomes (Hwang et al., Nature Biotechnology 31:227 (2013)) and can be used as an efficient means of site-specifically editing cell genomes in order to cleave DNA prior to the incorporation of a gene encoding a gene. The use of CRISPR/Cas to modulate gene expression has been described in, for instance, U.S. Pat. No. 8,697,359, the disclosure of which is incorporated herein by reference as it pertains to the use of the CRISPR/Cas system for genome editing. Alternative methods for site-specifically cleaving genomic DNA prior to the incorporation of a gene of interest in a cell include the use of zinc finger nucleases (ZFNs) and transcription activator-like effector nucleases (TALENs). Unlike the CRISPR/Cas system, these enzymes do not contain a guiding polynucleotide to localize to a specific sequence. Sequence specificity is instead controlled by DNA binding domains within these enzymes. The use of ZFNs and TALENs in genome editing applications is described, e.g., in Urnov et al., Nature Reviews Genetics 11:636 (2010); and in Joung et al., Nature Reviews Molecular Cell Biology 14:49 (2013), the disclosure of each of which are incorporated herein by reference as they pertain to compositions and methods for genome editing.

Additional genome editing techniques that can be used to incorporate polynucleotides encoding a TGFβ antagonist peptide into the genome of a cell of interest, such as a fibroblast, keratinocyte, Merkel cell, melanocyte, or Langerhans cell, include the use of ARCUS™ meganucleases that can be rationally designed so as to site-specifically cleave genomic DNA. The use of these enzymes for the incorporation of genes encoding a TGF-β antagonist peptide into the genome of a mammalian cell (e.g., a human cell) is advantageous in view of the defined structure-activity relationships that have been established for such enzymes. Single chain meganucleases can be modified at certain amino acid positions in order to create nucleases that selectively cleave DNA at desired locations, enabling the site-specific incorporation of a gene of interest into the nuclear DNA of a cell, such as a fibroblast, keratinocyte, Merkel cell, melanocyte, or Langerhans cell. These single-chain nucleases have been described extensively in, for example, U.S. Pat. Nos. 8,021,867 and 8,445,251, the disclosures of each of which are incorporated herein by reference as they pertain to compositions and methods for genome editing.

Vectors for Delivery of Exogenous Nucleic Acids to Cells
Viral Vectors for Nucleic Acid Delivery Viral genomes provide a rich source of vectors that can be used for the efficient delivery of exogenous genes encoding TGF-β antagonist peptides described herein into the genome of a cell (e.g., a mammalian cell, such as a human cell, e.g., a fibroblast, keratinocyte, Merkel cell, melanocyte, or Langerhans cell). Viral genomes are particularly useful vectors for gene delivery because the polynucleotides contained within such genomes are typically incorporated into the genome of a cell by generalized or specialized transduction. These processes occur as part of the natural viral replication cycle, and do not require added proteins or reagents in order to induce gene integration. Examples of viral vectors include AAV, retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding TGF-β antagonist peptides described herein to a mammalian cell (e.g., a human cell, such as a fibroblast, keratinocyte, Merkel cell, melanocyte, or Langerhans cell) include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in U.S. Pat. No. 5,801,030, the disclosure of which is incorporated herein by reference as it pertains to viral vectors for use in gene delivery.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventor regards as her invention.

Example 1. Characterization of TGF-β Antagonistic Activity

Cell Culture

Cells were grown in Dulbecco's modified Eagle's medium (DMEM) High Glucose with L-Glutamine, 10% fetal bovine serum (FBS), 100 IU/mL penicillin, 100 μg/mL streptomycin. Cells were maintained at 37° C., 95% relative humidity, and 5% $CO_2$.

Aggregation Assay.

Soluble peptides were separated from aggregates and precipitates by filtration. The molecular weight cut-off of the filter was chosen such that soluble protein was allowed to pass through the filter, while aggregate forms were retained. Peptide X and P16 previously dissolved in 50 mM Tris-HCl (pH=7.0) were left untreated or treated with 0.5% dimethyl sulfoxide (DMSO) for 2 hours at 4° C. Soluble protein was then separated from aggregated protein using a Microcon™ concentrator (Millipore), with a molecular weight cut-off of 100 kDa. The Microcon was spun in a desktop centrifuge at 16,000×g for 15 min. Aggregated protein retained on the membrane was resuspended in $H_2O$, pipetting repeatedly across the membrane to ensure that as much protein as possible was removed. Aliquots of soluble protein and aggregated protein were each mixed with 5× sample buffer (250 mM Tris-HCl, 40% glycerol, 140 mM SDS, 0.6 M β-mercaptoethanol, pH 6.8) and heated to 85-90° C. for 10 min prior to Tricine SDS-PAGE. Samples were analyzed by 17% Tricine SDS-PAGE and peptides visualized by silver staining.

Aggrescan Analysis

Aggrescan is a server for the prediction and evaluation of "hot spots" of aggregation in polypeptides [Conchillo-Sole et al. 2007, de Groot et al. 2012]. The website for this program is http://bioinf.uab.es/aggrescan and it is available to the public.

Luciferase Assay

Luciferase reporter assays were performed using a HEK293-$(CAGA)_{12}$ cell line that stably expresses a TGF-β/Smad3-responsive $(CAGA)_{12}$-luciferase reporter gene [Cash et al. 2013]. HEK293-$(CAGA)_{12}$ cells were grown in 24-well plates to 70-80% confluency and serum-starved overnight. Cells were washed with PBS and treated with or without TGF-β1 in presence or absence of various CD109-based peptides as indicated in the figure legends. Cells were then washed twice with cold PBS and solubilized in 100 μl of Passive Lysis Buffer (Promega) for 30 min at 4° C. The cell lysates were assayed for luciferase and β-galactosidase activities using commercially available kits (BD Biosciences).

Western Blotting

A431 cells were grown in 6-well plates to 70-80% confluency and serum-starved overnight. Cells were washed with PBS and treated with or without TGF-β1 in presence or absence of various CD109-based peptides as indicated in the figure legends. Cells were solubilized with 500 μl of lysis buffer (50 mM Tris, pH 7.5, 150 mM NaCl, 50 mM NaF, 50 mM β-glycerophosphate, 1 mM sodium orthovanadate, 1 mM dithiothreitol, 5 mM EDTA, pH 8.0, 1% Nonidet P-40, 10% glycerol, 10 μM phenylmethylsulfonyl fluoride, 200 μg/ml bovine serum albumin, 1 μg/ml leupeptin, 10 μg/ml soybean trypsin inhibitor, 10 μg/ml benzamide, and 2 μg/ml pepstatin) for 30 min at 4° C. with mild agitation. Cell lysates were collected and centrifuged for 10 min at 10,000× g. The supernatants were collected and protein concentrations were determined using the Bio-Rad protein assay kit. Lysates containing equivalent protein concentrations were mixed with 0.2 volume of 5× electrophoresis sample buffer containing 5% β-mercaptoethanol and boiled for 5 min. Samples were resolved on 7.5% SDS-polyacrylamide gels and transferred to nitrocellulose membranes. Membranes were blocked for 3 h in blocking buffer (30 mM Tris, pH 7.5, 150 mM NaCl, and 0.05% (w/v) Tween 20™ (Tris-buffered saline/Tween) containing 5% (w/v) skim milk powder). The blot was incubated overnight at 4° C. with a 1:1000 dilution of anti-PAI-1 antibody (BD Biosciences). Blots were washed with Tris-buffered saline/Tween and incubated for 45 min at room temperature with a 1:5000 dilution of secondary antibody conjugated to horseradish peroxidase (Pierce). Chemiluminescence detection of the immune complexes was performed using the ECL system (Amersham Biosciences) according to the manufacturer's instructions. The membranes were stripped and reprobed with an anti-GAPDH antibody to confirm equal protein loading.

TABLE 1

Characteristics of the peptides used

| Peptide Name | Peptide Number (on FIG. 3) | Aggregation? | Amino Acid Sequence | SEQ ID NO: |
|---|---|---|---|---|
| X | 1 | Aggregated | LGSSPHVRKHFPETWIWLDTNMGRSRIYQEFEVTVPDSITS | 1 |
| X-1 | 2 | Aggregated | ETWIWLDTNMGSRIYQEFEVTVPDSITS | 2 |
| A | 3 | Not aggregated | TMENVVHELELYNTGYYLGMFMNSFAVFQECGLWVLTDANLTKDYIDGVY DNAEYAERFMEENEGHIVDIHDFSLGSSPHVRKHFPETWIWLDTMNGSRI YQEFEVTVPDSITSWVATGFVISEDLGLGLTTTPVELQAFQPFFIFLNLP YSVIRGEEFAL | 3 |

TABLE 1-continued

Characteristics of the peptides used

| Peptide Name | Peptide Number (on FIG. 3) | Aggregation? | Amino Acid Sequence | SEQ ID NO: |
|---|---|---|---|---|
| P11 | 4 | Not aggregated | ETWIWLDTNMG | 4 |
| P16 | 5 | Not aggregated | ETWIWLDTNMGSRIYQ | 5 |
| P21 or X-2 | 6 | Not aggregated | ETWIWLDTNMGSRIYQEFEVT | 6 |
| P16-2 | 7 | Not aggregated | WINMDTGWLIEQRYTS | 7 |
| X-3 | 8 | Aggregated | LDTNMGSRIYQEFEVT | 8 |
| X-4 | 9 | Not aggregated | GSRIYQEFEVT | 9 |
| P16-1 | Not tested | Not aggregated | ILNTWMDSTQIGYRWE | 10 |
| Y | Not tested | Not tested | TMENVVHELELYNTGYYLGMFMNSFAVFQECGLWVLTDANLTKDYIDGVYDNAEYAERFMEENEGHIVDIHDFSLGSSPHVRKHFPETWIWLDTNMGSRIYQEFEVTVPDSITSWVATGFV | 17 |
| Z | Not tested | Not tested | LTKDYIDGVYDNAEYAERFMEENEGHIVDIHDFSLGSSPHVRKHFPETWIWLDTNMGSRIYQEFEVTVPDSITSWVATGFVISEDLGLGLTTTPVELQAFQPFFIFLNLPYSVIRGEEFAL | 18 |
| B | Not tested | Not tested | TMENVVHELELYNTGYYLGMFMNSFAVFQECGLWVLTDANLTKDYIDGVYDNAEYAERFMEENEGHIVDIHDFSLGSSPHVRKHFPETWIWLDTNMGSRIYQEFEVT | 19 |
| E | Not tested | Not tested | LTKDYIDGVYDNAEYAERFMEENEGHIVDIHDFSLGSSPHVRKHFPETWIWLDTNMGSRIYQEFEVTV | 20 |

Peptide X but not Peptide P16 Exhibited Aggregation

Figure 1:
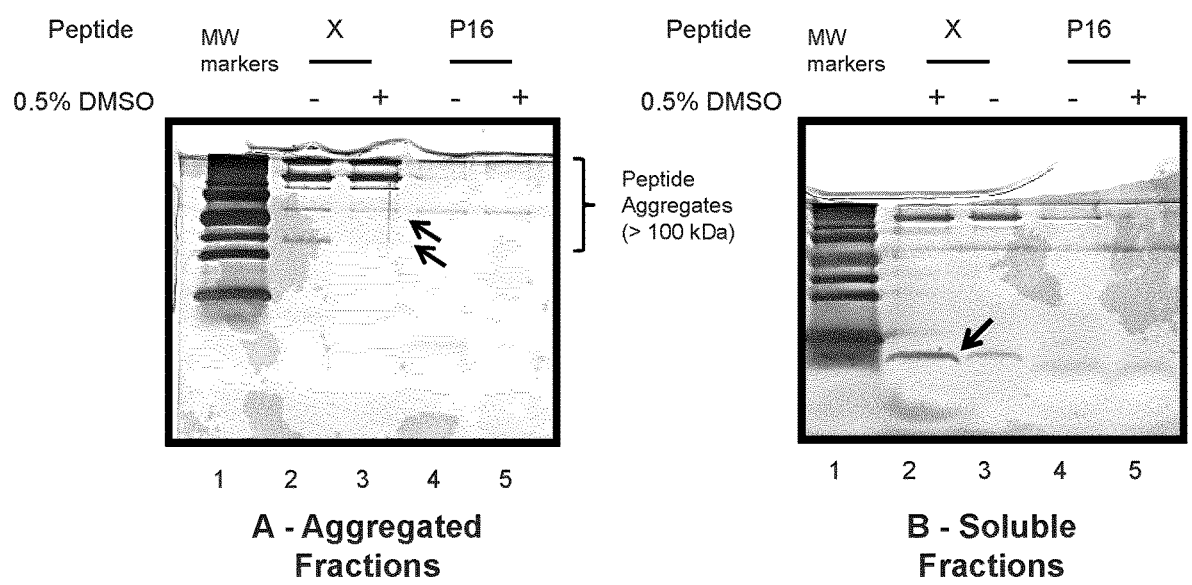
FIGS. 1A and 1B illustrate that peptide X but not peptide P16 exhibits aggregation. Peptide X (X, 40 amino acids) and P16 (16 amino acids) were left untreated (−) or treated with 0.5% DMSO (+) for 2 hrs at 4° C. The aggregated and non-aggregated soluble fractions were then separated using a Microcon™ centrifugal filtration device (Millipore), with a molecular weight cut-off of 100 kDa. This device allows passage of molecules <100 kDa through the filter but retains larger molecules (aggregates). The aggregated (FIG. 1A—left panel) and soluble (FIG. 1B—right panel) fractions were then separated by 17% Tricine-SDS gel electrophoresis and peptides detected by silver staining. In the conditions tested, multiple bands with various staining intensities were detected in peptide X aggregated fraction and two of these bands were decreased with DMSO treatment (A—left panel, arrows) leading to an increase in the amount of soluble peptide X (B—right panel, arrow, lane 2 versus 3). In contrast, P16 displayed only a few bands of low intensity in the aggregation fractions which were not altered by DMSO treatment, and no increase in the soluble peptide was noted (B—right panel, lane 4 versus 5). (A B) Lane 1: Molecular weight marker. Lanes 2-5: samples. As shown in this figure, peptide X existed predominantly in aggregated form and peptide X aggregation was partially reduced by treatment with DMSO, leading to an increase in soluble peptide X.

Peptide X (X, 40 amino acids) and P16 (16 amino acids) were left untreated (−) or treated with 0.5% DMSO (+) for 2 hrs at 4° C. The aggregated and non-aggregated (soluble) fractions were then separated using a Microcon centrifugal filtration device (Millipore), with a molecular weight cut-off of 100 kDa. This device allows passage of molecules less than 100 kDa through the filter but retains larger molecules (aggregates). The aggregated and soluble fractions were then separated by 17% Tricine-SDS gel electrophoresis and peptides visualized by silver staining. As shown in FIG. 1, multiple bands with various staining intensities were detected in the peptide X aggregated fraction and the intensities of two of these bands were decreased by 0.5% DMSO treatment (FIG. 1A, arrows) which was associated with an increase in the amount of soluble peptide X (FIG. 1B, arrow). In contrast, P16 displayed only a few bands of low staining intensity in the aggregation fractions indicating that this peptide aggregated only to a minor extent. The data presented in FIG. 1 suggests that peptide X existed predominantly in aggregated form and that peptide X aggregation was partially decreased by DMSO treatment leading to an increase in soluble peptide X.

In Silico Analysis of Peptide X Aggregation Propensity and the Design of Aggregation-Free Small Molecular Weight CD109-Based Peptides As shown in FIG. 2A, Aggrescan analysis of peptide X identified amino acids at position 13 to 18 (ETWIWL, SEQ ID NO: 11) as an aggregation-prone sequence in the 40 amino acid peptide. Importantly, this sequence was identified as part of the putative TGF-β binding domain. Definition of terms: .#=position of the amino acid in peptide X (i.e. #1-40); 'AA'=identity of the amino acid (single letter nomenclature); 'a4v'=intrinsic aggregation propensity of each amino acid residue; Hot Spot Area (HSA)=the area of the AP graph, above the hot spot threshold (HST), of a given HS calculated with trapezoidal integration (data not shown). Normalized Hot Spot Area (NHSA) value was calculated as the HSA divided by the number of residues in the input amino acid sequence. α4v average in the Hot Spot (a4vAHS)=a4v average in a given HS.

To design a small molecular weight CD109-based peptide containing the TGF-β binding domain and at the same time having a low propensity for self-aggregation, a series of N- and C-terminal deletions of peptide X were tested to determine whether removing any of these amino acids would alter aggregation properties. Deletion of 1-22 amino acids from the C-terminus of peptide X yielded sequences that were predicted to contain the same aggregation prone segment (ETWIWL) whereas deletion of exactly 12 amino acids from the N-terminus of peptide X gave a 28 amino acid sequence (X-1) that contained the ETWIWL segment but was predicted to have a low propensity to aggregate ('aggregation-free'). Using X-1 as a starting point, a series of smaller peptides were designed by further deleting N- and/or C-terminal amino acids of X-1 (X-2, X-3, X-4, P16, P11) to determine the minimum sequence required produce an aggregation-free peptide that inhibited TGF-β-signaling (see FIG. 2B). The peptides were analyzed for aggregation by size-exclusion chromatography (see below, FIGS. 3-4) and tested for TGF-β-inhibitory activity in cell-based assays (see below, FIGS. 5-9).

Figure 3:
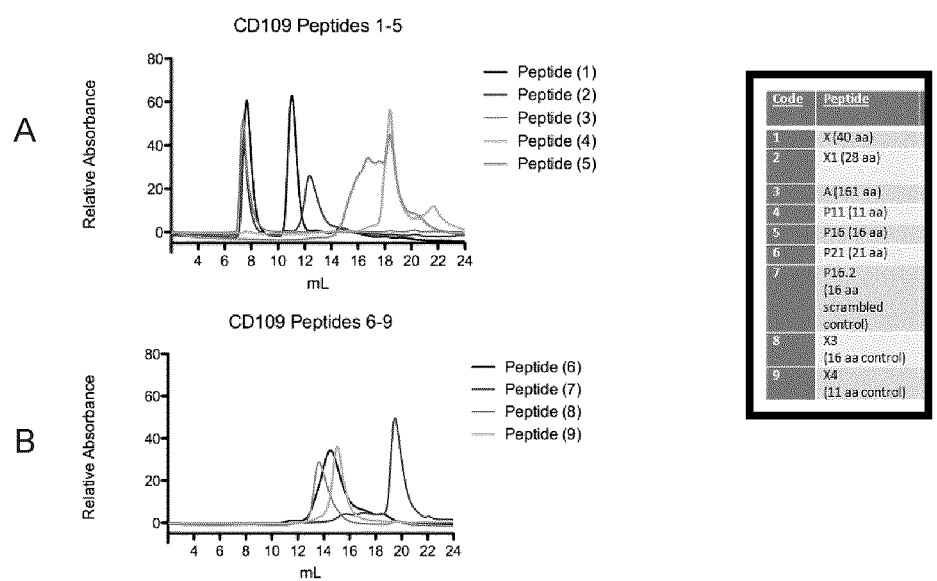
FIGS. 3A and 3B illustrate that, as determined by size-exclusion chromatography, small molecular weight CD109-based peptides X, X-1 and X-3 form aggregates whereas P21, P16, P16-2 (control), P11 and X-4 do not (refer to FIG. 2B for a description of the amino acid sequence of the peptides). Approximately 200 µg of each peptide X (40 amino acids), X-1 (28 amino acids), peptide A (161 amino acids), P11 (11 amino acids), P16 (16 amino acids), P21 (21 amino acids, P16-2 (16 amino acids, scrambled sequence control), X-3 (16 amino acids) and X-4 (11 amino acids) were dissolved in phosphate-buffered saline (PBS) and loaded onto a Superdex Peptide 10/300GL column. The column was eluted with PBS at a flow rate of 0.6 mL/min and eluents were analyzed for peptide content by measuring relative absorbance at a wavelength of 215 nM.

Size-exclusion chromatography of small molecular weight CD109-based peptides indicated that peptide X, X-1 and X-3 formed aggregates whereas P21, P16, P16-2 (control), P11 and X-4 did not (FIG. 3). More specifically, approximately 200 μg of each peptide X (40 amino acids), X-1 (28 amino acids), peptide A (161 amino acids), P11 (11 amino acids), P16 (16 amino acids), P21 (21 amino acids, P16-2 (16 amino acids, scrambled sequence control), X-3 (16 amino acids) and X-4 (11 amino acids) were dissolved in phosphate-buffered saline (PBS) and loaded onto a Superdex Peptide 10/300GL column. The column was eluted with PBS at a flow rate of 0.6 ml/min and eluants were analyzed for peptide content by measuring relative absorbance at a wavelength of 215 nM. The data were plotted with relative absorbance (Y-axis) against elution volume (X-axis). As shown in FIG. 3, peptide X (peptide 1) elution profile indicated two major peaks at approximately 8 mL and 11 mL which correspond to molecular weights greater than 12.4 kDa. The theoretical molecular weight of peptide X is 4.7 kDa which is expected to elute from the column at approximately 15 mL. These results suggest that peptide X existed as high molecular weight aggregates with minimal soluble (monomeric) form under these conditions. P16 (peptide 5) elution profile indicated a peak between 14-22 mL which was expected to contain peptides of between 0.1 and 6 kDa and is consistent with its theoretical molecular weight of 2.01 kDa. A summary of findings for the remaining peptides analyzed in the top and middle panels is provided in Table 1.

Figure 4:
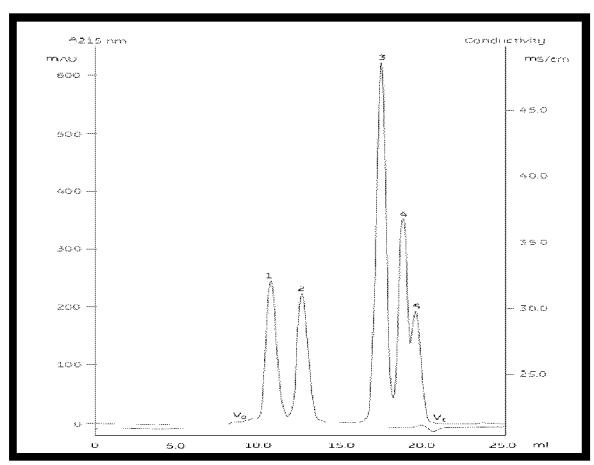
FIG. 4 illustrates the standard curve used for size-exclusion chromatography of standard peptides using the Superdex Peptide 10/300 GL column (results provided in FIG. 3). A pool of standard peptides of various molecular weights (1. cytochrome c ($M_r$ 12.384 kDa) 1 mg/mL; 2. aprotinin ($M_r$ 6.512 kDa) 2 mg/mL; 3. vitamin $B_{12}$ ($M_r$ 1.355 kDa) 0.1 mg/mL; 4. $(Gly)_3$ ($M_r$ 0.189 kDa) 0.1 mg/mL; 5. Gly ($M_r$ 0.075 kDa) 7.8 mg/mL) were subjected to size-exclusion chromatography using the Superdex Peptide 10/300 GL column (flow rate 0.5 ml/min at room temperature, sample volume of 50 µL, eluent 0.05M phosphate, 0.15 M NaCl, ph 7.0). The resulting chromatogram (absorbance at 215 nm (in mAU, left Y axis) and conductivity (in mS/cm, right Y axis, in function of volume of elution (in mL)) indicates the elution profiles of the above peptides with high MW peptides eluting in earlier fractions and lower MW peptides eluting in later fractions as expected. The molecular weights of peptides were plotted against elution volume generating a standard curve (not shown).
Figure 5A:
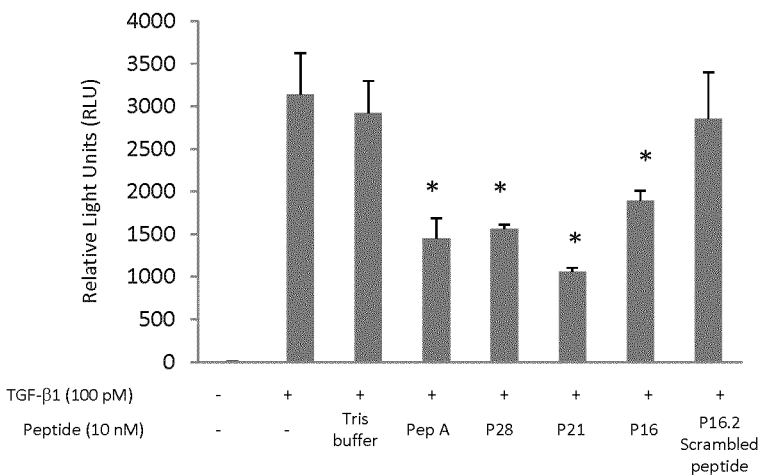
FIGS. 5A and 5B illustrate that some small molecular weight CD109-based peptides (Peptide A, P28, P21 and P6) inhibit TGF-β1-induced Smad3-driven transcriptional activity. HEK293 cells stably transfected with the Smad3-responsive $CAGA_{12}$-lux luciferase reporter were treated for 18 hours without (−) or with (+) 100 pM TGF-β1 in the presence or absence of 10 nM (FIG. 5A) or 5 nM (FIG. 5B) of peptide A (Pep A, 161 aa), P28 (28 aa), P21 (21 aa), P16 (16 aa), P16-2 (16 aa, scrambled P16 sequence) or Tris-buffer (buffer control) as indicated. Cell lysates were analyzed for luciferase activity and data are expressed as mean±standard deviation of relative light units (RLU). Asterisks (*) indicate that the values are significantly different from values obtained using TGF-β1 treatment alone (P<0.05). Under the conditions tested, peptide A, P28, P21 and P16 inhibited TGF-β1-induced transcriptional ($CAGA_{12}$-lux) activity. Tris buffer alone had no effect indicating that the inhibitory activity of Pep A, P21 and P16 are mediated by the peptides themselves and not from the buffer (Tris) in which they were dissolved. Scrambled peptide also had no effect indicating that the inhibitory effect of P16 (and Peptide A, P28 and P21) was mediated in a sequence specific manner and was not due to amino acid composition or charge of the peptides.
Figure 5B:
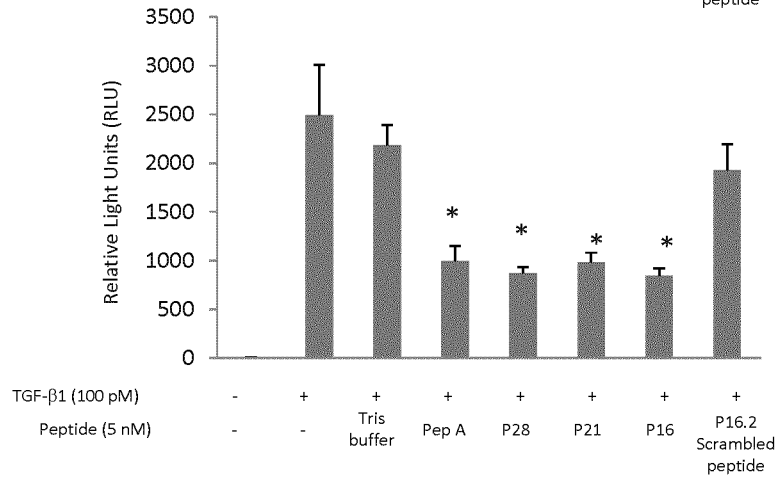

The elution pattern of molecular weight standards in size exclusion chromatography is shown in FIG. 4. More specifically, a pool of standard proteins of various molecular weights were subjected to size-exclusion chromatography using the Superdex Peptide 10/300 GL column. The resulting chromatogram indicated the elution profiles of the peptides with high molecular weight peptides eluting in earlier fractions and lower molecular weight peptides eluting in later fractions as expected. The molecular weights of peptides were plotted against elution volume generating a standard curve (not shown) and was used to calculate molecular weights of the CD109-based peptides. The identity of the peptides, their molecular weights and conditions of the analysis are indicated in the bottom panel.

Small Molecular Weight CD109-Based Peptides with Low Propensity to Aggregate Inhibited TGF-β1-Induced Transcriptional (Smad3-Driven CAGA$_{12}$-Lux) Activity HEK293 cells stably transfected with the Smad3-responsive CAGA$_{12}$-lux luciferase reporter were treated for 18 hours without (−) or with (+) 100 pM TGF-β1 in the presence or absence of 10 nM (FIG. 5A) or 5 nM (FIG. 5B) of peptide A (Pep A, 161 aa), P28 (28 aa peptide), P21 (21 aa peptide), P16 (16 aa peptide), P16.2 scrambled peptide (16 aa, scrambled P16 sequence) or Tris-buffer (negative control for peptides) as indicated. In summary, Peptide A, P28 (X-1), P21 (X-2) and P16 inhibited TGF-β1-induced CAGA$_{12}$-lux activity. Tris buffer alone had no effect indicating that the inhibitory activity of Pep A, P21 and P16 were mediated by the peptides themselves and not from the buffer (Tris) in which they were dissolved. The scrambled peptide (P16.2) also had no inhibitory effect indicating that the inhibitory effect of P16 (and Pep A, P28 and P21) was mediated in a sequence specific manner and was not due to amino acid composition or charge of the peptides.

Figure 6:
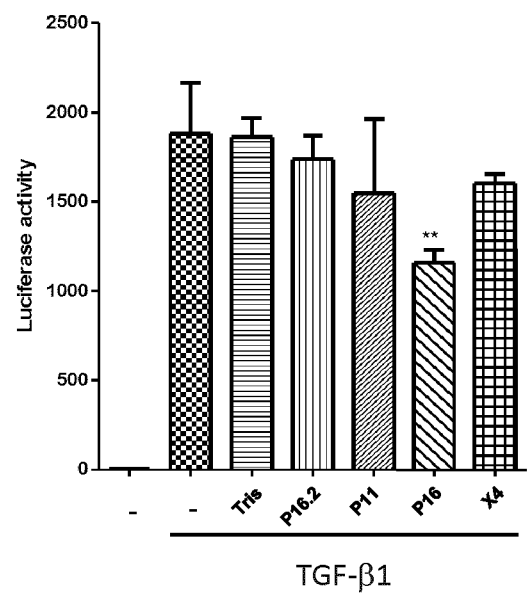
FIG. 6 illustrates that the small molecular weight CD109-based peptide P16 (but not P16-2, P11 or X-4) inhibit TGF-β1-induced Smad3-driven transcriptional activity. HEK293 cells stably transfected with the Smad3-responsive $CAGA_{12}$-lux luciferase reporter were treated for 18 hours without (−) or with (+) 100 pM TGF-β1 in the presence or absence of 10 nM of P16-2 (16 aa scrambled control), P11 (11 aa sequence), P16 (16 aa), X-4 (11 aa) or Tris-buffer (buffer control) as indicated. Cell lysates were analyzed for luciferase activity and data are expressed as mean±standard deviation of luciferase activity. Results are shown as luciferase activity for the peptides used. Asterisks (*) indicate that the values are significantly different from values obtained using TGF-β1 treatment alone (P<0.05). Under the conditions tested, P16 inhibited TGF-β1-induced transcriptional activity whereas P11 and X-4 did not. Tris buffer alone had no effect indicating that the inhibitory activity of P16 is mediated by the peptide itself and not from the buffer (Tris) in which P16 was dissolved. P16-2 (scrambled peptide control) also had no effect indicating that the inhibitory effect of P16 is mediated in a sequence specific manner and is not due to amino acid composition or charge of the peptide.

Small Molecular Weight CD109-Based Peptide P16, but not P11 or X-4, Inhibited TGF-β1-Induced Smad3-Driven (CAGA$_{12}$-Lux) Transcriptional Activity HEK293 cells stably transfected with the Smad3-responsive CAGA$_{12}$-lux luciferase reporter were treated for 18 hours without (−) or with (+) 100 pM TGF-β1 in the presence or absence of 10 nM of P16-2 (16 aa, scrambled P16 sequence), P11 (11 aa peptide), P16 (16 aa peptide), X-4 (11 aa peptide) or Tris-buffer (negative control for peptides) as indicated. As shown in FIG. 6, P16 inhibited TGF-β1-induced CAGA$_{12}$-lux activity and P11 and X-4 did not. Tris buffer alone had no effect indicating that the inhibitory activity of Pep A, P21 and P16 were mediated by the peptides themselves and not from the buffer (Tris) in which they were dissolved. P16-2 (scrambled peptide control) also had no effect indicating that the inhibitory effect of P16 was mediated in a sequence specific manner and was not due to amino acid composition or charge of the peptide.

Figure 7:
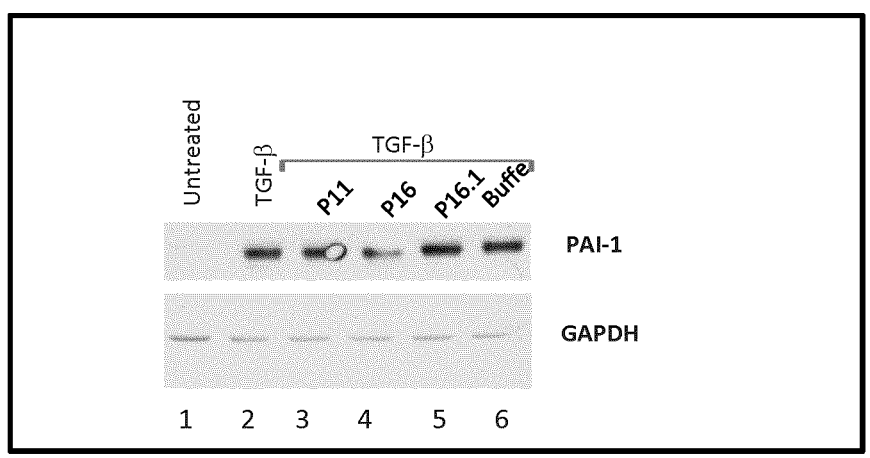
FIG. 7 illustrates that the small molecular weight CD109-based peptide P16 (but not P11 or P16-1) inhibits TGF-β1-induced PAI-protein production. A431 cells were treated without (lane 1) or with 100 pM of TGF-β1 (lanes 2-6) in the absence (lane 2) or presence of 10 nM of P11 (11 aa peptide, lane 3), P16 (16 aa peptide, lane 4), P16-1 (scrambled peptide of 16 aa, lane 5) or Tris buffer (buffer, lane 6) for 24 hrs. Cell lysates were analyzed by Western blot for PAI-1 (protein activator inhibitor-1) protein levels and normalized to GAPDH protein levels (loading control). In the conditions tested, P16 (but not P11) inhibited TGF-β1-induced PAI-1 expression. Buffer alone had no effect indicating that the inhibitory effect of P16 is mediated by the peptide itself and not due to the buffer in which it was dissolved. Scrambled P16-1 control peptide also had no effect indicating that the inhibitory effect of P16 was mediated in a sequence specific manner and was not due to amino acid composition or charge of the peptide. GAPDH levels were similar for all samples indicating that equal amounts of protein were loaded in each lane.
Figure 8:
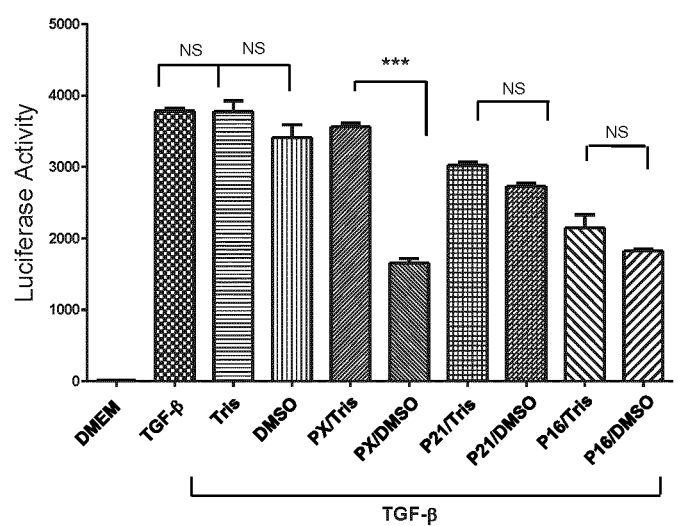
FIG. 8 illustrates that DMSO treatment enhances the TGF-β inhibitory activity of Peptide X but not P21 or P16. HEK293 cells stably transfected with the Smad3-responsive $CAGA_{12}$-lux luciferase reporter were treated for 18 hours without (−) or with (+) 100 pM TGF-β1 in the presence or absence of Peptide X (PX), P21 or P16. The peptides were previously dissolved in Tris buffer and left untreated or treated with DMSO prior to addition to the cells. Addition of Tris buffer or DMSO alone served as additional controls. Cell lysates were analyzed for luciferase activity and data are expressed as mean±standard deviation of luciferase activity. Results are shown as luciferase activity. Asterisks (*) indicate that the values are significantly different from values obtained using TGF-β1 treatment alone (P<0.05), whereas NS indicates that the values are not significantly different. Under the conditions tested, peptide X pre-treated with DMSO inhibited TGF-β1-induced transcriptional activity whereas peptide X left untreated (Tris buffer only) did not. P16 and P21 inhibited TGF-β1-induced $CAGA_{12}$-lux activity and these effects were not enhanced by DMSO treatment. DMSO alone had no effect on TGF-β1-induced $CAGA_{12}$-lux activity indicating that the inhibition of DMSO-treated peptide X is due to the peptide itself and not due to DMSO. Tris buffer alone had no effect on TGF-β1-induced $CAGA_{12}$-lux activity indicating that the inhibitory effect of P21 and P16 were mediated by the peptides themselves and not from the buffer (Tris) in which they were dissolved.

Small Molecular Weight Aggregation-Free CD109-Based Peptide P16 (but not P11 or P16-1 Scrambled Control) Inhibited TGF-β1-Induced PAI-Protein Production A431 cells were treated without (lane 1) or with 100 pM of TGF-β1 (lanes 2-6) in the absence (lane 2) or presence of 10 nM of P11 (11 aa peptide, lane 3), P16 (16 aa peptide, lane 4), P16-1 (scrambled peptide of 16 aa, lane 5) or Tris buffer (buffer, lane 6) for 24 hrs. Cell lysates were analyzed by Western blot for PAI-1 (protein activator inhibitor-1) protein levels and normalized to GAPDH protein levels (loading control). As shown in FIG. 7, P16 (but not P11) inhibited TGF-β1-induced PAI-1 protein production. Tris buffer alone had no effect indicating that the inhibitory effect of P16 was mediated by the peptide itself and not due to the buffer in which it was dissolved. Scrambled P16-1 control peptide also had no effect indicated that the inhibitory effect of P16 was mediated in a sequence specific manner and was not due to amino acid composition or charge of the peptide. GAPDH levels were similar for all samples indicating that equal amounts of protein were loaded in each lane.

DMSO Treatment Enhanced the TGF-β Inhibitory Activity of Peptide X, but not of P21 or P16

HEK293 cells stably transfected with the Smad3-responsive CAGA$_{12}$-lux luciferase reporter were treated for 18 hours without (−) or with (+) 100 pM TGF-β1 in the presence or absence of Peptide X (PX), P21 or P16. The peptides were previously dissolved in Tris buffer and left untreated or treated with 0.5% DMSO prior to their addition to the cells. Tris buffer and 0.5% DMSO alone served as additional controls. As shown on FIG. 8, Peptide X pretreated with 0.5% DMSO inhibited TGF-β1-induced CAGA$_{12}$-lux activity whereas Peptide X left untreated (Tris buffer only) did not. P16 and P21 inhibited TGF-β1-induced CAGA$_{12}$-lux activity and these effects were not enhanced by DMSO treatment. DMSO alone had no effect on TGF-β1-induced CAGA$_{12}$-lux activity indicating that the inhibition of DMSO-treated peptide X is due to the peptide itself and not due to DMSO. Tris buffer alone had no effect on TGF-β1-induced CAGA$_{12}$-lux activity indicating that the inhibitory effect of P21 and P16 were mediated by the peptides themselves and not from the buffer (Tris) in which they were dissolved.

DMSO Treatment Enhanced the TGF-β Inhibitory Activity of Peptide X, but not of P16

Figure 9:
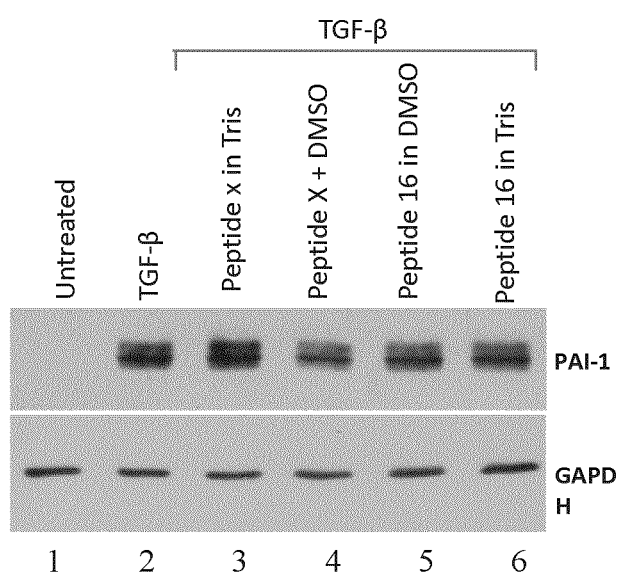
FIG. 9 illustrates that DMSO treatment enhanced the TGF-β inhibitory activity of peptide X, but not P16. A431 cells were treated for 18 hours without (−) or with (+) 100 pM TGF-β1 in the presence or absence of Peptide X or P16. The peptides were previously dissolved in Tris buffer and left untreated or treated with DMSO prior to addition to the cells. Cell lysates were analyzed by Western blot for PAI-1 (plasminogen activator inhibitor-1) protein expression (top panel) and GAPDH served as a loading control (bottom panel). PAI-1 was not detected in untreated cells (lane 1). In the conditions tested, TGF-β1 treatment increased PAI-1 production in A431 cells (lane 2 versus lane 1). Under the conditions tested, peptide X treated with DMSO inhibited TGF-β1-induced PAI-1 protein production whereas peptide X left untreated (in Tris) did not (compare lanes 4, 3 and 2). Furthermore, P16 inhibited TGF-β1-induced PAI-1 protein production and pre-treating the peptide with DMSO did not enhance its inhibitory effect (compare lanes 6, 5 and 2).

A431 squamous cell carcinoma cells were treated for 18 hours without (−) or with (+) 100 pM TGF-β1 in the presence or absence of Peptide X or P16. The peptides were dissolved in Tris buffer and left untreated or treated with 0.5% DMSO prior to addition to the cells. Cell lysates were analyzed by Western blot for PAI-1 (protein activator inhibitor-1) protein expression (top panel) and GAPDH served as a loading control (bottom panel). As shown in FIG. 9, PAI-1 was not detected in untreated cells (lane 1). TGF-β1 treatment increased PAI-1 production in A431 cells (lane 2 versus lane 1). Peptide X treated with DMSO inhibited TGF-β1-induced PAI-1 protein production whereas peptide X left untreated (in Tris) did not (compare lanes 4, 3 and 2). P16 inhibited TGF-β1-induced PAI-1 protein production and pre-treating the peptide with DMSO did not enhance its inhibitory effect (compare lanes 6, 5 and 2).

The results shown in FIG. 9 also showed that the peptides inhibit PAI-1 production in A431 squamous cell carcinoma cells. Upregulation of PAI-1 production is an indicator of cancer cell migration and invasion.

The results presented in this example indicate that the design of a small molecular weight CD109-based peptide (P16, 16 amino acids) that contains the putative TGF-β binding region of CD109 and inhibits TGF-β signaling cannot be deduced solely on the basis of previous knowledge of sequence information for Peptide A (described in U.S. Pat. No. 7,173,002). Further, results showing that peptide X (in the absence of DMSO treatment) could not inhibit TGF-β signaling were unexpected since peptide X was obtained from N- and C-terminal deletion regions from peptide A and retained the putative TGF-β binding region. In the present example, it is shown that peptide X aggregated in solution and failed to inhibit TGF-β signaling in cell-based assays unless its aggregation is decreased by DMSO treatment. Although treatment with DMSO partially reduces peptide X aggregation and confers it with TGF-β-inhibitory activity, a vast majority of peptide X remains in aggregated form. Using a combination of in silico aggregation analysis together with physicochemical and functional analysis, the problem of peptide aggregation was overcome and resulted in the identification of a novel CD109-based peptide of 16 amino acids (P16) that does not aggregate in solution, retains the putative TGF-β binding region and potently inhibits TGF-β signaling in vitro.

Example 2. Cancer Cell Migration Assay

Material and Methods

Squamous cell carcinoma (A431) or breast cancer (MDA-MB-231) cells were grown to 80-90% confluence and serum-starved overnight. The next day, cells were scratched with a plastic pipette tip (time 0 hour) and then left untreated or treated for 24 hours with 100 pM TGF-β1 alone or in the presence of 10 nM peptide B (100 aa), E (67 aa), or X1 (P28, 28 aa). Digital images were captured at 0 h and 24 h (20× magnification) using an EVOS XL Core microscope.

Figure 10:
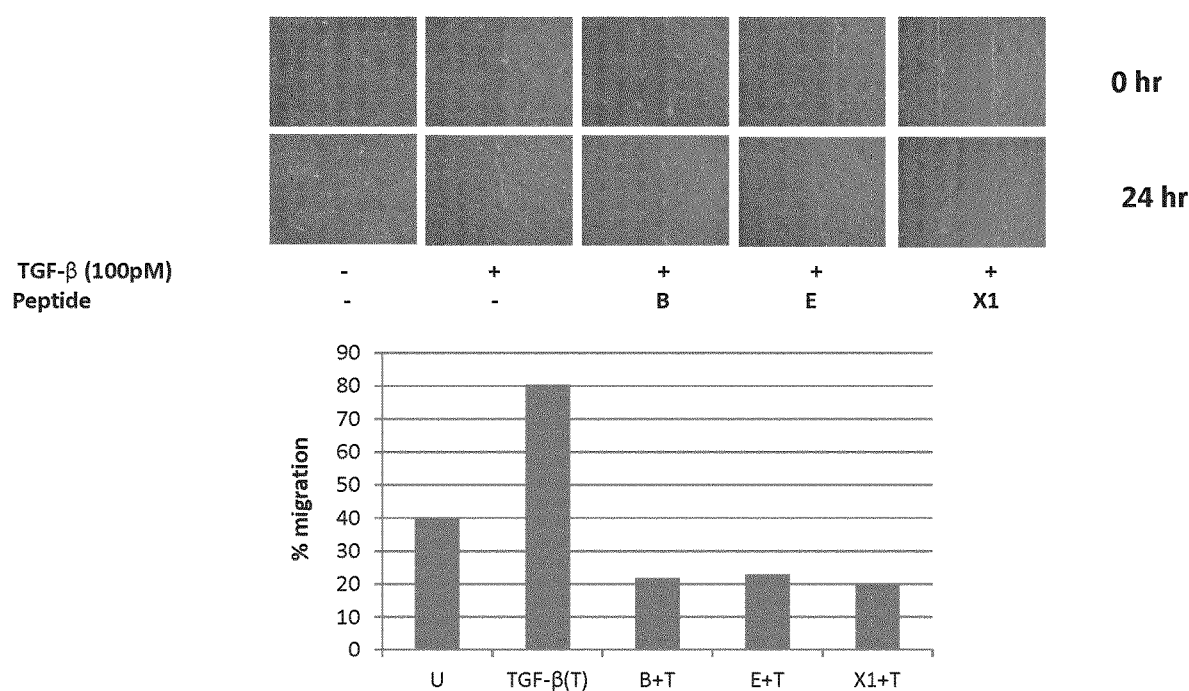
FIG. 10 illustrates that peptides B, E and X-1 inhibit TGF-β-induced cellular migration of A431 cells in vitro. Results are shown prior to treatment (0 hr, top panels) and after treatment (24 hr, bottom panels) for each of the peptides used. (See FIG. 2 and Table 1 for the amino acid sequence identity of the peptides).
Figure 11:
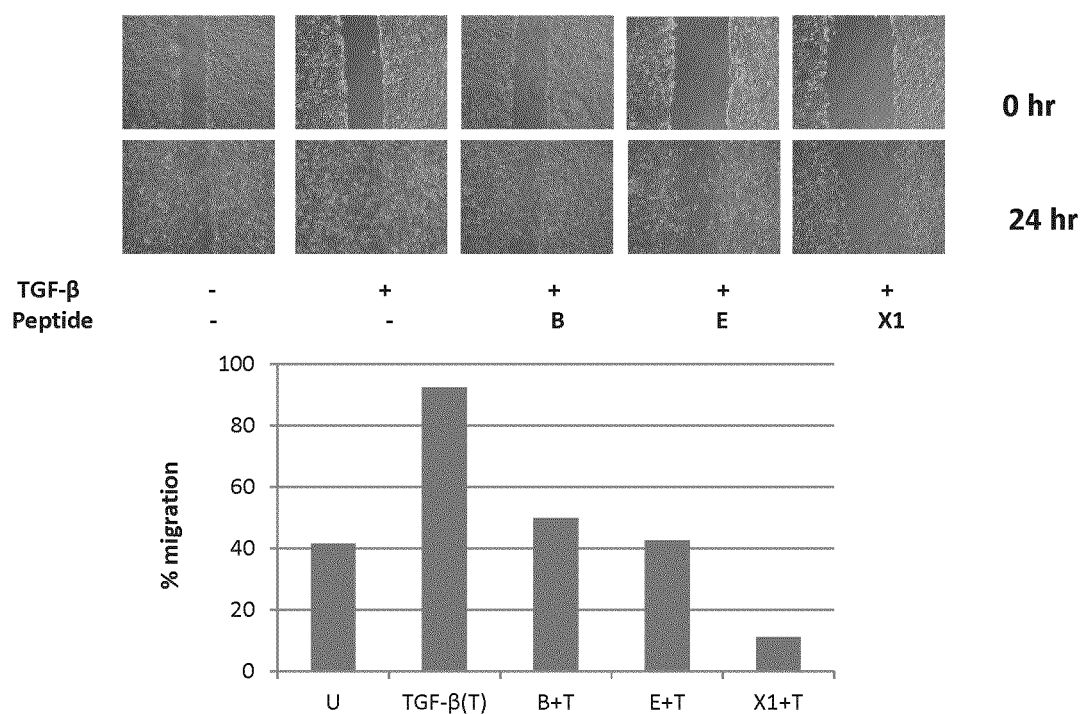
FIG. 11 illustrates that peptides B, E and X-1 inhibit TGF-β-induced cellular migration of MDA-MB-231 cells in vitro. Results are shown prior to treatment (0 hr, top panels) and after treatment (24 hr, bottom panels) for each of the peptides used.

Cell migration is a process central to the development of multicellular structures. It involves the movement of cells from their site of origin to a new cell site in response to physical and biochemical signals. Cell migration is involved in the invasion of cancer cells into surrounding tissue and the vasculature in the initial step in tumor metastasis. We examined the effect of various CD109-based peptides on cell migration in squamous cell carcinoma (A431) and breast cancer (MDA-MB-231) cells using scratch assay. Results presented in FIG. 10 and FIG. 11 indicated that peptides B, E and X1/P28 inhibited TGF-_-induced migration in these cells. These results suggested that small molecular weight CD109-based may have application for the treatment of cancer metastasis.

Example 3. The Role of CD109 in the Epithelial-Mesenchymal Transition

Cancer Profiling Array

The expression of CD109 in vulvar squamous cell carcinoma was determined using a Cancer Profiling Array™ (BD BiosciencesClontech, Mississauga, ON, Canada). The Cancer Profiling Array II was hybridized with a $^{32}$P-labeled CD109 cDNA probe. Prehybridization, hybridization, and detection were performed using BD Express Hyb™ Solution (BD Biosciences/Clontech) according to the manufacturer's instructions.

Cell Lines

HaCaT clones and A431 cells stably expressing CD109 (or its empty vector, EV) were generated as described in Bizet et al., 2011. The highly differentiated and highly tumorigenic epidermal squamous cell carcinoma SCC-1327 were cultured in Keratinocyte Serum-free Media supplemented with 30 μg/ml Bovine Pituitary Extract, 0.1 ng/ml of recombinant EGF (Invitrogen Carlsbad, Calif., USA) and 100 U/ml penicillin and 50 μg/ml streptomycin.

siRNA Transfections.

HaCaT, A431 and SCC-13 cells were transfected with CD109 siRNA (ID#129083) or a negative control siRNA (ID#4611) (Ambion, Austin, Tex., USA) using Lipofectamine 2000™ (Invitrogen) according to the manufacturer's instructions.

Western Blot.

Western blot analyses were conducted with the following antibodies: mouse monoclonal anti-CD109, anti-fibronectin (both from BD Biosciences), and anti-β-actin (C4) antibodies (Santa Cruz Biotechnology), rabbit polyclonal anti-p44/42 MAPK (ERK), anti-p38 MAPK, anti-phospho-p38 MAPK (Thr180/Tyr182) and rabbit monoclonal anti-phospho p44/42 MAPK (Thr202/Tyr204), anti-Slug (C19G7) (all from Cell Signaling Technologies, Danvers, Mass., USA).

Immunofluorescence Microscopy

Cells were treated with 0-100 pM TGF-β1, in the presence or absence of 10 μM U0126 (Cell signaling Technologies), 1 μM SB203580, 0.5 μM SB431542 (both from Ascent) for 36-40 hrs. Cells were fixed with 4% paraformaldehyde for 10 min at 37° C. and non-specific sites were blocked with 10% NGS, 0.1% Triton X-100 in PBS. E-cadherin was detected using a FITC-conjugated anti-E-cadherin antibody (BD Biosciences), followed by an AlexaFluor488™-conjugated anti-FITC antibody (Molecular Probes). F-actin was detected using Rhodamin-conjugated phalloidin (Cytoskeleton, Denver, Colo.) and nuclei were stained with DAPI (Sigma Aldrich). Images were acquired with an Olympus BX60 fluorescent microscope coupled to a QColor3™ camera (Olympus) using Image ProPlus™ 6.0 software.

Scratch Assay

Confluent monolayers of HaCaT or A431 cells were wounded by scrapping the cells with a 200 μl pipette tip. Cells were then incubated with 100 pM TGF-β1, in presence or absence of 10 μM U0126, 1 μM SB203580, 0.5 μM SB431542 in serum free medium for 24-48 hrs. Pictures were taken at the same spot at 0 hr, 24 hrs and 48 hrs. The cell-free area (wound) area was measured using ImageJ™ software and the percentage of original wound area filled with keratinocytes was calculated. At least 3 independents series of experiments were performed in triplicates.

Matrigel™ Invasion Assay

The BD BioCoat Matrigel™ Cell Culture Inserts (BD Biosciences, USA) were used for invasion assays. Briefly, the control inserts or Matrigel™-coated inserts were rehydrated with plain DMEM for 2 hrs before use. These were then filled with cells after transfection and recovery ($5 \times 10^4$ cells in 0.5 ml of DMEM), and placed in a well of a 24-well plate. At 22 hrs after incubation the cells on the upper side of the filters were removed with cotton-tipped swabs. Migrated and/or invaded cells on the lower side of the filters were fixed and stained with 0.05% Crystal Violet. The cells on the underside of the filters were viewed under a microscope and counted.

Statistical Methods

Numerical results are represented as means of n independent experiments±SEM. A two-tailed Student t test was used to determine statistical significance between two groups. Comparisons within more than two groups were made by Holm-Sidak test following one-way ANOVA using SigmaSTAT.

Figure 12:
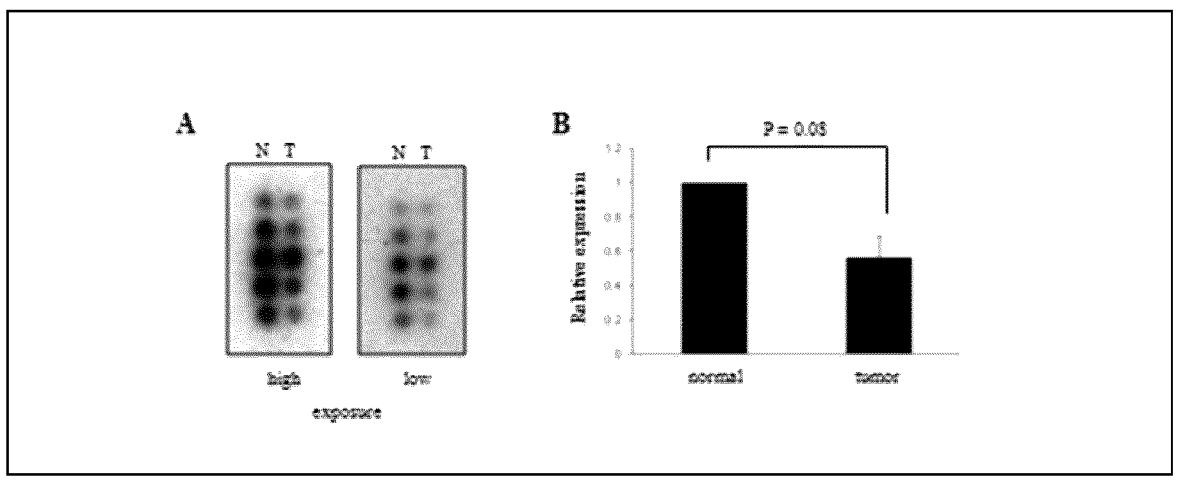
FIGS. 12A and 12B illustrate that CD109 mRNA expression is decreased in late stage vulvar squamous cell carcinoma. The Cancer Profiling Array II™ (BD Biosciences/Clontech, Mississauga, ON) was hybridized with a $^{32}$P-labeled CD109 cDNA probe. Prehybridization, hybridization, and detection were performed using BD Express Hyb™ Solution (BD Biosciences/Clontech) according to the manufacturer's instructions.

CD109 expression is decreased in late stage vulvar squamous cell carcinoma. To assess the expression of CD109 in squamous cell carcinoma, the expression of CD109 mRNA in late stage vulvar squamous cell carcinoma was analyzed using a cancer profiling array. As shown in FIG. 12A, CD109 expression is decreased in 5 out of 5 tumors of vulvar squamous cell carcinoma as compared to the corresponding adjacent normal skin tissue.

CD109 Inhibits TGF-β-Induced Epithelial-Mesenchymal Transition

Figure 13:
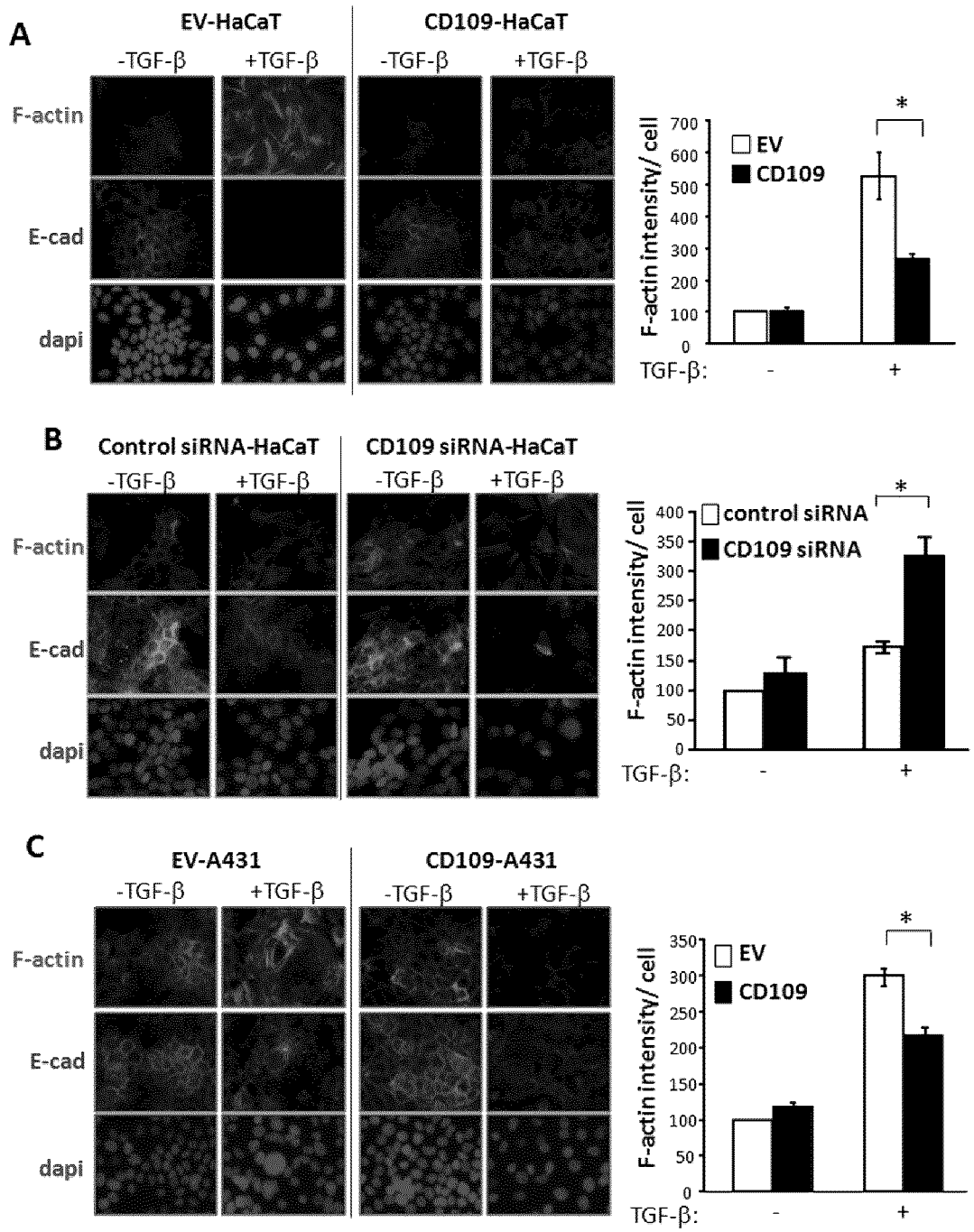
FIGS. 13A-13F illustrate that CD109 inhibits TGF-β-induced EMT.
Figure 13:
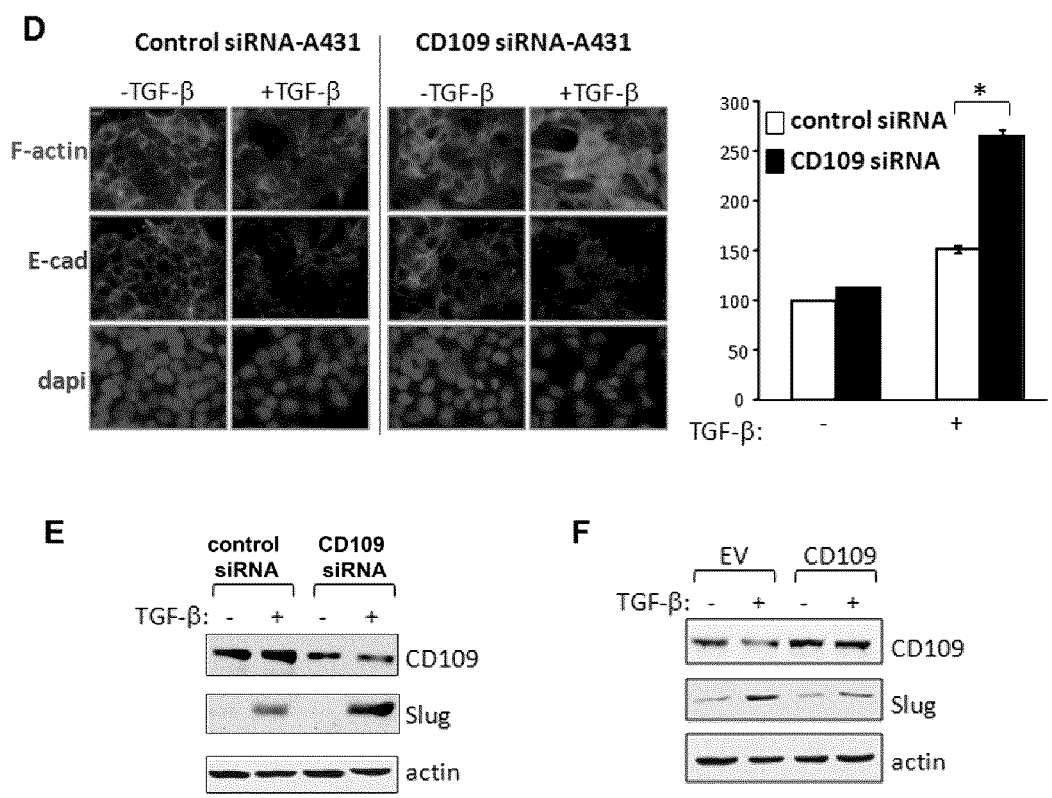

It was previously shown that CD109 is an inhibitor of TGF-β signaling and responses in skin cells, the role of CD109 in regulating TGF-β-induced EMT was investigated, by first looking at two different markers: the appearance of actin stress fibers and the disappearance of E-cadherin from the membrane. HaCaT cells stably overexpressing CD109 show a marked decrease in actin stress fibers formation upon TGF-β treatment (the actin filament appears more cortical) as compared to EV transfected cells (FIG. 13A). Quantification of F-actin staining intensity demonstrates that the effect of CD109 on TGF-β-induced actin stress fibers formation is statistically significant ($p<0.05$). In addition, HaCaT cells overexpressing CD109 also display a decrease in TGF-β-induced loss of membrane E-cadherin, as compared to EV transfected cells (FIG. 13A).

Similarly, knock-down of CD109 expression in HaCaT cells results in a significant ($p<0.05$) increase of actin stress fibers appearance and an increase of membrane E-cadherin delocalization upon TGF-β treatment, as compared to control siRNA transfected cells (FIG. 13B). This result indicates that, in human non-tumorigenic keratinocytes, CD109 can inhibit some of the characteristics of TGF-β-induced EMT.

Figure 19:
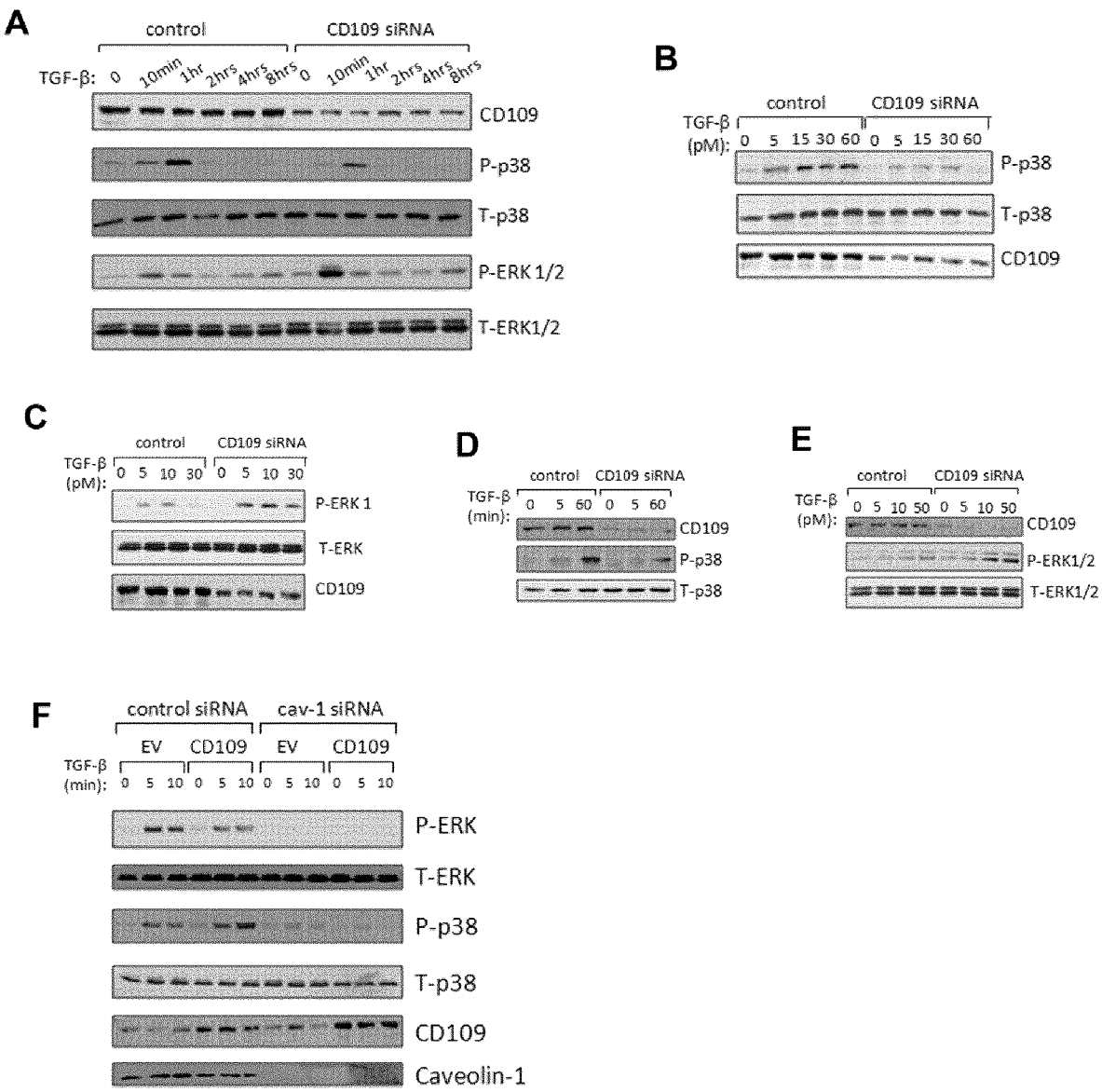

It was then examined whether CD109 inhibits TGF-β-induced EMT in tumorigenic cell lines, the A431 and SCC-13, which both derived from epidermal squamous cell carcinomas (FIGS. 13C-D and 20A). As observed in HaCaT cells, A431 cells stably overexpressing CD109 display less actin stress fibers and reduced loss of membrane E-cadherin after TGF-β treatment as compared to EV transfected cells (FIG. 13C). Moreover, A431 and SCC-13 cells transfected with CD109 siRNA show more actin stress fibers ($p<0.05$) and a more cytoplasmic localization of E-cadherin, than in control siRNA transfected cells after TGF-β treatment (FIGS. 13D and 19A). These results suggest that exogenous and endogenous CD109 is able to inhibit TGF-β-induced EMT in SCC-derived cells.

Figure 20:
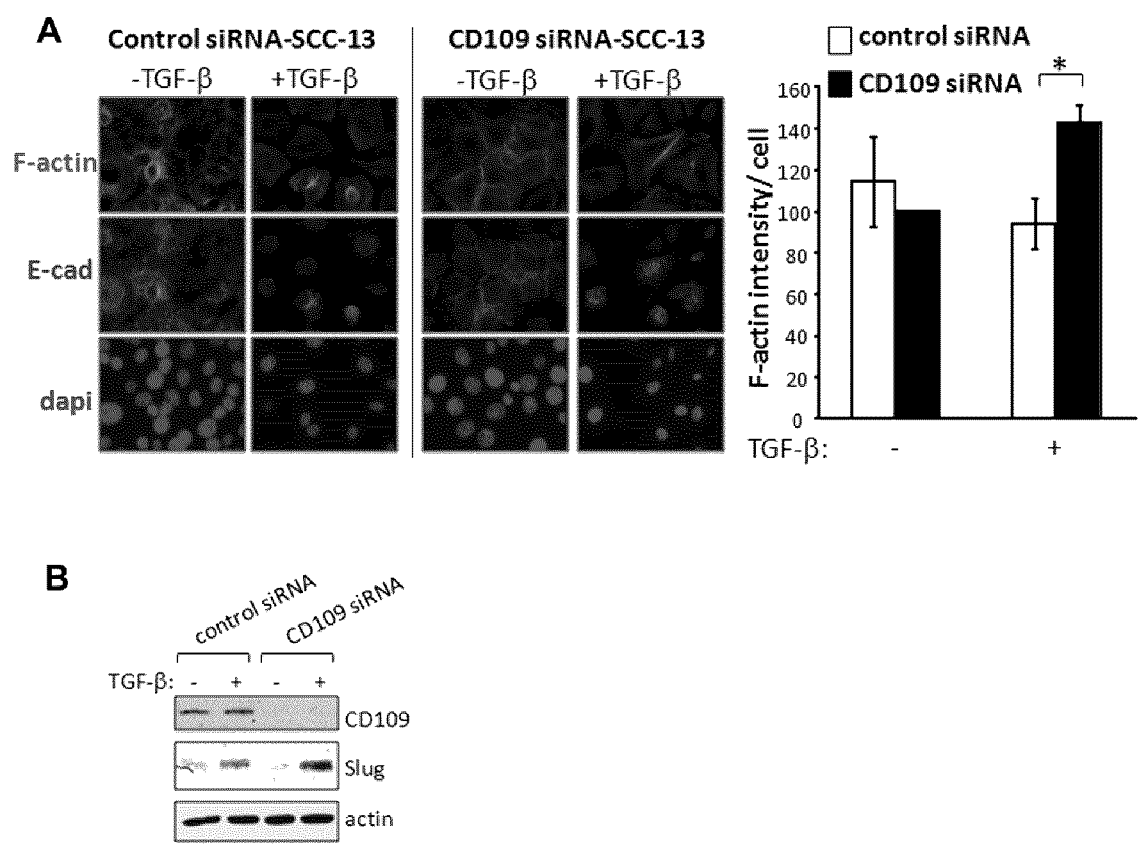

Consistent with CD109's ability to inhibit TGF-β-induced EMT, it was shown that CD109 is also able to decrease TGF-β-induced fibronectin expression, in HaCaT cells as well as in SCC cells (FIG. 20). Collectively, these results indicate that CD109 is able to inhibit several key features of TGF-β-induced EMT, including production of ECM components, such as fibronectin.

CD109 Inhibits TGF-β-Induced Slug Expression.

Because TGF-β can promote the expression of the transcription factor Slug, that initiates EMT and acts as master regulator of the EMT process, it was determined whether CD109 affects TGF-β-induced Slug expression. Transfection of HaCaT and SCC-13 cells with CD109 siRNA increases TGF-β-induced Slug expression, as compared to control siRNA transfected cells (FIGS. 13E and 19B). In addition, overexpression of CD109 in A431 cells reduces the level of Slug expression, as compared to EV transfection (FIG. 13F). Altogether, these results imply that CD109 can reduce TGF-β-induced Slug expression and this may contribute to inhibition of TGF-β-induced EMT by CD109.

CD109 Inhibits Cell Migration in HaCaT and SCC Cell Lines.

Figure 14:
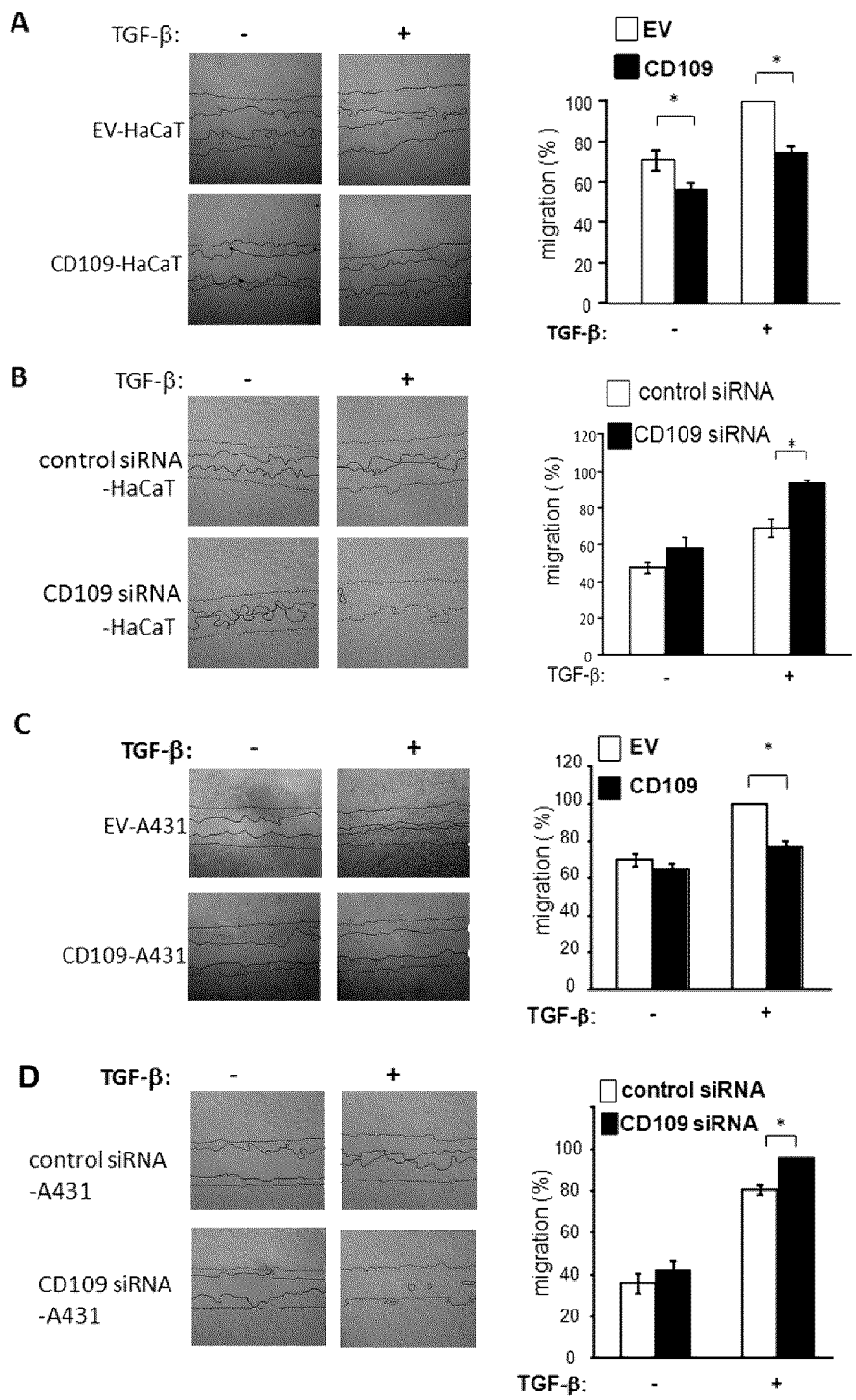
FIGS. 14A-14D illustrate that CD109 inhibits TGF-β-induced cell migration.

Cells undergoing EMT display enhanced migratory capacity. Thus, in vitro wound healing (scratch) assays were performed to evaluate the role of CD109 in regulating TGF-β-induced cell migration. Results shown in FIG. 14 demonstrate that TGF-β treatment in HaCaT and A431 cells decreases the wounded area 24 hrs post wounding, as compared to cells left untreated, which is consistent with TGF-β's ability to promote cell migration. Importantly, HaCaT cells stably overexpressing CD109 display a less migratory phenotype, in the absence and in the presence of TGF-β, as compared to EV transfected cells (FIG. 14A). This result confirms previous observation showing that CD109S, a shorter, placental version of CD109, inhibits migration of HaCaT cells. The effect of CD109 on cell migration in the absence of TGF-β treatment might be due to inhibition of autocrine TGF-β signaling. The reduction in wound gap closure observed in CD109 overexpressing cells is not the result of reduced cell growth, since CD109 enhances cell proliferation.

In addition, knock-down of CD109 expression enhances TGF-β-induced "wound" closure, as compared to control siRNA transfected cells (FIG. 14B), indicating that endogenous CD109 is able to inhibit TGF-β-induced migration.

Moreover, CD109 overexpression inhibits TGF-β-induced migration of A431 cells (FIG. 14C) while knock-down of CD109 increases migration (FIG. 14D). Together, these results suggest that CD109 can decrease the migration rate of SCC cells in response to TGF-13 and is consistent with a decrease in TGF-β-induced EMT.

CD109 Inhibits Cell Invasion in A431 SCC Cells

In the transwell Matrigel™ invasion assay, as shown in FIG. 15A, TGF-β treatment of A431 cells resulted in increased invasion of these cells. However, A431 cells over expressing CD109 when treated with TGF-β show reduced invasion as compared to empty vector transfected cells. In addition, knockdown of CD109 in A431 cells increases TGF-β mediated invasion compared to control siRNA transfected cells as shown in FIG. 15B. These results suggest that CD109 can decrease the invasion of SCC cells in response to TGF-β. CD109's effects on EMT involves both SMAD and MAPK pathways.

Several studies indicate an important role for both SMAD2/3 and p38 and ERK MAPK pathways in TGF-β-induced EMT. To investigate whether CD109's ability to inhibit TGF-β-induced EMT involves the SMAD or the MAPK pathway, three different inhibitors were used: SB431542, an inhibitor of TGFBR1 shown to inhibit the SMAD2/3 pathway; U0126, an inhibitor of the ERK1/2 pathway and SB203580, an inhibitor of p38 MAPK at concentrations that specifically blocks their respective pathways (FIG. 22) and examined the involvement of each pathway in CD109's ability to inhibit EMT. Treatment with SB431542, U0126 and SB203580 had no effect in the absence of TGF-β (data not shown). Importantly, SB431542, U0126 or SB203580 treatment in the presence of TGF-β reduces (but does not abrogate) the effect mediated by CD109 siRNA transfection on actin stress fibers appearance and relocalization of E-cadherin (FIGS. 16A and B). These findings suggest that, when CD109 levels are reduced, TGF-β induces EMT at least via the SMAD2/3, ERK and p38 pathways. In control siRNA transfected cells, SB431542 totally prevents the appearance of actin stress fibers (FIGS. 16A and B), suggesting that the SMAD2/3 pathway is the principal pathway mediating EMT in these cells. Interestingly, the combination of SB431542+U0126, SB431542+SB203580 totally abrogates the TGF-β-induced appearance of actin stress fibers and relocalization of membrane E-cadherin in both CD109 siRNA and control siRNA transfected cells (FIGS. 16A and B), suggesting that the SMAD and MAPK pathways may cooperate to promote TGF-β-induced EMT. Together, these results suggest that, when CD109 expression is reduced, TGF-β mediates its effect on EMT via both SMAD and MAPK pathways.

Next, the role of the SMAD2/3 and MAPK pathways was examined in CD109's effect on fibronectin and Slug expression. Knock-down of CD109 using siRNA in HaCaT cells dramatically increases TGF-β-induced fibronectin expression (FIG. 17A). Fibronectin production is totally abrogated by SB431542 treatment and is reduced by SB203580 and U0126 treatment, suggesting that p38 and ERK participate to a much lesser extent than the SMAD2/3 pathway, in fibronectin production (FIG. 17A).

In contrast, the effect of CD109 knock-down on TGF-β-induced Slug expression is abrogated by SB431542 and U0126 treatment, suggesting that SMAD2/3 and ERK contribute to the elevation of Slug expression mediated by CD109 siRNA (FIG. 17B). Surprisingly, SB203580 treatment in the absence (data not shown) or in the presence of TGF-β(FIG. 17B) increases Slug expression in HaCaT cells transfected with control siRNA and CD109 siRNA transfected cells, suggesting that p38 may inhibit Slug expression in HaCaT cells.

CD109's Effects on Migration Involves Both SMAD and MAPK Pathways

Finally, it was determined whether CD109's effect on migration was also mediated by the SMAD2/3 and MAPK pathways. Knock-down of CD109 increases cell migration, in the presence of TGF-β(FIGS. 18A and B). This increase is partially reversed by SB431542 and U0126 treatment and to a much lesser extent by SB203580 (FIGS. 18A and B). The combination of SMAD2/3 with MAPK inhibitors (SB431542+U0126 or SB431542+SB203580) totally blocks the effect of CD109 siRNA on TGF-β-induced migration (FIGS. 18A and B), suggesting that the MAPK pathways cross-talk with the SMAD2/3 pathway to modulate cell migration. Collectively, these results suggest that CD109 negatively regulates TGF-β-induced cell migration via the SMAD2/3 and MAPK pathways.

CD109 Modulates TGF-β-Induced MAPK Phosphorylation

The results presented so far suggested that CD109 could not only negatively regulate SMAD2/3 signaling in keratinocytes, but also could modulate non-canonical pathways, notably p38 and ERK1/2 MAPK pathways. Thus, CD109's ability to regulate TGF-β-induced p38 and ERK 1/2 phosphorylation was investigated. Treatment of HaCaT cells with 15 pM of TGF-β1 results in rapid phosphorylation of p38 and ERK1/2 (FIG. 19A). Interestingly, knock-down of CD109 leads to a decrease in TGF-β-induced p38 phosphorylation and an increase in TGF-β-induced ERK 1/2 phosphorylation, especially at early (10 min to 1 hr) time points (FIG. 19A). In addition, examination of TGF-β dose response demonstrates that CD109 siRNA transfection decreases p38 phosphorylation (FIG. 19B) and increases ERK phosphorylation (FIG. 19C) at all dose of TGF-β tested, as compared to control siRNA transfection. No change in the levels of total ERK and total p38 were observed. Together, these results indicated that endogenous CD109 is able to promote TGF-β-induced p38 activation while inhibiting TGF-β-induced activation of ERK pathway in HaCaT cells.

Next, CD109's ability to modulate TGF-β-induced MAPK pathways in SCC cell lines was studied. Similar to what was observed in HaCaT cells, CD109 siRNA transfection reduces TGF-β-induced p38 phosphorylation and enhances TGF-β-induced ERK phosphorylation in both A431 (FIGS. 19D and E) and SCC-13 cells (FIGS. 23A and B), as compared to negative control siRNA transfection. Collectively, the results suggested that CD109 is able to inhibit TGF-β-induced SMAD and ERK 1/2 pathways, but promotes TGF-β-induced p38 MAPK pathway in human keratinocytes and in SCC-derived cells.

CD109's Effects on TGF-β-Induced MAPK Activation Involve the Caveolae

Localization of the TGF-β receptors to the caveolar compartment has been implicated in MAPK activation. Because it was previously shown that CD109 promotes the localization of the TGF-β receptors to the caveolae, it was investigated whether CD109's ability to regulate TGF-β-induced p38 and ERK phosphorylation requires the caveolar pathway. Consistent with the above results, overexpression of CD109 in HaCaT cells leads to a reduction in TGF-β-induced ERK phosphorylation and an increase in TGF-β-induced p38 phosphorylation, as compared to EV transfected cells (FIG. 19F). Importantly, the effect of CD109 on ERK and p38 activation is abrogated by caveolin-1 siRNA transfection (FIG. 19F), suggesting that CD109, by promoting TGF-β receptor localization to the caveolae, is able to regulate TGF-β-induced MAPK activation.

CD109 Expression is Deregulated in Many Types of Human Cancers, Particularly in SCCs The expression of CD109 has been found to be significantly higher in cervical SCCs as compared to endometrial adenocarcinomas and normal cervix and endometrium. CD109 is also more frequently expressed in lung SCC compared with other types of lung carcinomas. In addition, CD109 expression was shown to be up regulated in head and neck SCCs (HNSCCs) and pre-malignant lesions of the oral cavity, but not in normal squamous epithelia. CD109 expression was found to be higher in low grade and non-muscle invasive urothelial carcinoma and associated with better prognosis. In oral squamous cell carcinoma, CD109 expression was found to be higher in well differentiated SCCs compared to moderately and poorly differentiated SCCs. In colorectal cancer, CD109 was shown to be mutated at significant frequency and the CD109 promoter showed higher frequency of methylation as compared to normal healthy subjects.

In the present study, it was found that CD109 expression was down regulated in 5 out of 5 tumors of late stage vulvar carcinoma compared to adjacent normal tissues. These results corroborate with previous findings which also observed decreased expression of CD109 in poorly differentiated vulvar tumors compared to well and moderately differentiated tumors.

It was previously shown that CD109 is a TGF-β co-receptor that inhibits SMAD2/3 pathway, promotes the localization of TGF-β receptor in caveolae and enhances their degradation mediated by SMAD7 and Smurf2. Because TGF-β is a potent inducer of EMT, a program leading to the escape of cancer cells from solid tumors to form metastasis, it was sought to determine whether CD109 could regulate TGF-β-induced EMT in SCC-derived cell lines. In the present example, it was demonstrated that CD109 negatively regulates key features of TGF-β-induced EMT: CD109 inhibited the TGF-β-induced appearance of actin stress fibers, the relocalization of cell-cell adhesion molecule E-cadherin, decreased ECM production and the expression of the initiator of EMT Slug and inhibited TGF-β-induced cell migration, in both HaCaT and SCC derived cell lines. Using specific inhibitors, it was shown that CD109 mediated its diverse effects on TGF-β-induced EMT via both the SMAD2/3 and p38 and ERK1/2 MAPK pathways. Finally, the results indicated that CD109 was able to increase TGF-β-induced p38 phosphorylation, while reducing ERK1/2 activation, probably by targeting the receptor localization to the caveolae. CD109 regulated both TGF-β canonical and non-canonical signaling pathways to inhibit TGF-β-induced EMT.

The results presented herein indicated that CD109 reduced TGF-β-induced SMAD2/3 and ERK1/2 phosphorylation, but increased TGF-β-induced p38 phosphorylation levels. CD109-mediated reduction of ERK1/2 activation levels and CD109's ability to inhibit EMT are consistent with ERK's involvement in cytoskeleton remodeling, disassembly of cell adherent junction and cell motility. The function of ERK and p38 MAPK highly depends on the duration, strength of the signal and on their location. Consistent with previous results demonstrating that CD109 promoted the localization of TGF-β receptor into lipid raft/caveolae and that TGF-β-induced MAPK activation occurred in lipid raft, the results suggest that activation of p38 and downregulation of ERK by CD109 likely occurred in caveolae. It is thus possible that the function of these MAPKs in caveolae differs from their function in other cell compartments, as they may not interact with the same partners.

The result suggested that p38 activation decreases Slug expression, thus CD109, by increasing TGF-β-induced p38 activation may further decrease Slug expression and EMT. While inhibition of p38 pathway increased Slug expression, it is not associated with a reduction of E-cadherin expression, as evidence by immunofluorescence. One possible explanation is that p38 pathway inhibited Slug expression in these cells, but differentially affected other transcription factors, such as Snail and Twist, whose function are known to overlap with Slug's. Interestingly, inhibition of the p38 pathway has only a minor effect on actin stress fibers appearance, E-cadherin relocalization, cell migration and fibronectin expression. This suggests that the increased activation of p38 by CD109 is not directly involved in CD109's inhibition of EMT. In contrast, the effect of CD109 is totally abrogated when SB203580 is used in combination with SMAD2/3 inhibitor, indicating the existence of a cross-talk between the different pathways. Indeed, MAPKs can phosphorylate the SMAD on their linker region to regulate their transcriptional activity. MAPK can also activate transcription factors that synergize or antagonize SMADs function.

Our results show that CD109 inhibited several features of EMT induced by TGF-β. The ability of TGF-β to mediate an EMT-like phenotype (or partial EMT) in HaCaT cells has been reported previously. However, it has been shown that, in addition to TGF-β treatment, Ras activation is required in order to obtain a more mesenchymal phenotype, indicating that synergy between different pathways is necessary for the cells to undergo a full EMT. Although in the presence of TGF-β alone, HaCaT cells do not undergo a full EMT but rather a partial EMT, any changes in cell migration are likely to be of importance during cancer invasion and metastasis. Thus, the finding that manipulation of CD109 expression levels lead to changes in migration of SCC cells may be of critical importance in cancer progression. In agreement with this notion, it has recently been reported that CD109 expression is elevated in premalignant lesional and well-differentiated SCCs as compared to normal epithelia, and that its expression levels decreases as the cells become poorly differentiated. Based on the results showing that CD109 reduces TGF-β-induced growth inhibition in HaCaT cells and that CD109 inhibits TGF-β-induced EMT in HaCaT and SCCs cells, a role for CD109 in cancer progression is herewith suggested. Without wishing to be bound to theory, the upregulation of CD109 may contribute to tumor progression by inhibiting TGF-β-induced growth arrest in the early stage of the disease, while the loss of CD109 expression at later stage of the disease may relieve the inhibition of TGF-β-mediated EMT, thus promoting tumor invasion.

The EMT program is not only employed by cancer cells to become invasive, but can occur also in other diseases, such as fibrosis, to trigger the formation of excess fibrous connective tissue. Therefore, it is possible that CD109, by regulating EMT, may play an important role not only in tumor progression but also during tissue fibrosis.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Bizet A A, Liu K, Tran-Khanh N, Saksena A, Vorstenbosch J, Finnson K W, Buschmann M D, Philip A: The TGF-beta co-receptor, CD109, promotes internalization and degradation of TGF-beta receptors. Biochim Biophys Acta: Molecular Cell Research 2011, 1813(5):742-753.

Cash J N, Angerman E B, Kirby R J, Merck L, Seibel W L, Wortman M D, Papoian R, Nelson S, Thompson T B: Development of a Small-Molecule Screening Method for Inhibitors of Cellular Response to Myostatin and Activin A. Journal of biomolecular screening 2013, 18(7):837-844. Conchillo-Sole O, de Groot N S, Aviles F X, Vendrell J, Daura X, Ventura S: AGGRESCAN: a server for the prediction and evaluation of "hot spots" of aggregation in polypeptides. BMC bioinformatics 2007, 8:65.

de Groot N S, Castillo V, Grana-Montes R, Ventura S: AGGRESCAN: method, application, and perspectives for drug design. Methods Mol Biol 2012, 819:199-220.

Wang W: Protein aggregation and its inhibition in biopharmaceutics. International journal of pharmaceutics 2005, 289(1-2):1-30.

Frokjaer S, Otzen D E: Protein drug stability: a formulation challenge. Nature reviews Drug discovery 2005, 4(4): 298-306.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A transforming growth factor-β (TGF-β) antagonist comprising a dimer comprising two copies of a TGF-β-binding peptide, each peptide comprising the amino acid sequence:
ETWIWLDTNMGXaa$_1$RIYQ (SEQ ID NO: 26)
wherein Xaa$_1$ is any naturally-occurring amino acid, and wherein said TGF-β-binding peptide comprises fewer than 125 amino acids.

2. The TGF-β antagonist of claim 1, wherein each TGF-β-binding peptide comprises the amino acid sequence selected from the group consisting of ETWIWLDTNMGSRIYQ (SEQ ID NO: 5), ETWIWLDTNMGSRIYQE (SEQ ID NO: 22, ETWIWLDTNMGSRIYQEF (SEQ ID NO: 23), ETWIWLDTNMGSRIYQEFE (SEQ ID NO: 24), ETWIWLDTNMGSRIYQEFEV (SEQ ID NO: 25), ETWIWLDTNMGSRIYQEFEVT (SEQ ID NO: 6), and ETWIWLDTNMGSRIYQEFEVTVPDSITS (SEQ ID NO: 2).

3. The TGF-β antagonist of claim 1, wherein each TGF-β binding peptide consists of ETWIWLDTNMGSRIYQ (SEQ ID NO: 5).

4. The TGF-β antagonist of claim 1, wherein each of said copies of said TGF-β-binding peptide are covalently bound to one another by a disulfide bond or thioether bond.

5. The TGF-β antagonist of claim 1, wherein the Xaa$_1$ is S or Y.

6. The TGF-β antagonist of claim 1, further comprising one or more peptides, small molecules and/or proteins conjugated to at least one of said TGF-β-binding peptide, optionally by way of one or more linkers.

7. The TGF-β antagonist of claim 1, wherein each of said TGF-β-binding peptide is a linear peptide.

8. The TGF-β antagonist of claim 1, wherein each copy of said TGF-β-binding peptide is covalently bound to a cysteine residue at the N-terminus or the C-terminus of said TGF-β-binding peptide, and wherein said cysteine residues are covalently bound to one another by a disulfide bond.

9. The TGF-β antagonist of claim 1, wherein each copy of said TGF-β-binding peptide is covalently bound to a cysteine residue at the N-terminus or the C-terminus of said TGF-β-binding peptide, and wherein said cysteine residues are covalently bound to one another by way of a linker.

10. The TGF-β antagonist of claim 9, wherein each of said cysteine residues is covalently bound to said linker by a thioether bond.

11. The TGF-β antagonist of claim 9, wherein said linker comprises an alkyl, aryl, heteroaryl, cycloalkyl, or heterocycloalkyl moiety.

12. The TGF-β antagonist of claim 1 further comprising a linker, wherein each copy of said TGF-β-binding peptide is bound to the other via the linker.

13. The TGF-β antagonist of claim 1, wherein each copy of said TGF-β-binding peptide comprises one or more additional amino acids linked to a spacer to form the dimer.

14. The TGF-β antagonist of claim 13, wherein the one or more additional amino acids is a lysine residue or a cysteine residue.

15. A pharmaceutical composition comprising the TGF-β antagonist of claim 1 and a pharmaceutically acceptable carrier.

16. The pharmaceutical composition of claim 15, wherein said TGF-β antagonist is formulated for oral administration, intravenous administration, intraocular administration, administration by inhalation, transdermal administration, sublingual administration or transmucosal administration.

* * * * *